(12) United States Patent
Younger et al.

(10) Patent No.: US 11,474,111 B2
(45) Date of Patent: Oct. 18, 2022

(54) METHODS FOR CHARACTERIZING AND ENGINEERING PROTEIN-PROTEIN INTERACTIONS

(71) Applicants: A-Alpha Bio, Inc., Seattle, WA (US); Olympic Protein Sciences LLC, Seattle, WA (US)

(72) Inventors: David Younger, Seattle, WA (US); David Colby, Seattle, WA (US); Randolph Lopez, Seattle, WA (US); Michael Wittekind, Seattle, WA (US)

(73) Assignee: A-Alpha Bio, Inc. et al, Seattle, WA (US)

( * ) Notice: Subject to any disclaimer, the term of this patent is extended or adjusted under 35 U.S.C. 154(b) by 0 days.

(21) Appl. No.: 17/553,259

(22) Filed: Dec. 16, 2021

(65) Prior Publication Data

US 2022/0107326 A1    Apr. 7, 2022

Related U.S. Application Data

(63) Continuation of application No. 17/619,506, filed as application No. PCT/US2021/035246 on Jun. 1, 2021.

(Continued)

(51) Int. Cl.
    *G01N 33/68*    (2006.01)
    *C12N 15/10*    (2006.01)
    *C12N 15/81*    (2006.01)

(52) U.S. Cl.
    CPC ..... *G01N 33/6845* (2013.01); *C12N 15/1055* (2013.01); *C12N 15/81* (2013.01)

(58) Field of Classification Search
CPC . G01N 33/6845; C12N 15/81; C12N 15/1055
See application file for complete search history.

(56) References Cited

U.S. PATENT DOCUMENTS 5,695,941 A    12/1997   Brent et al.
6,057,101 A    5/2000    Nandabalan et al.
(Continued)

FOREIGN PATENT DOCUMENTS

CA      2666336      5/2008
EP      1292710 B1    8/2007
(Continued)

OTHER PUBLICATIONS

Rothstein R., "Targeting, disruption, replacement, and allele rescue: integrative DNA transformation in yeast," Methods Enzymol. 1991;194:281-301. doi: 10.1016/0076-6879(91)94022-5. PMID: 2005793.

(Continued)

*Primary Examiner* — Robert H Havlin
(74) *Attorney, Agent, or Firm* — Gardella Grace P.A.

(57) ABSTRACT

Characterization of the binding dynamics at the interface between any two proteins that specifically interact plays a role in myriad biomedical applications. The methods disclosed herein provide for the high-throughput characterization of the specific interaction at the interface between two protein binding partners and the identification of functionally significant mutations of one or both protein binding partners. For example, the methods disclosed herein may be useful for epitope and paratope mapping of an antibody-antigen pair, which is useful for the discovery and development of novel therapies, vaccines, diagnostics, among other biomedical applications.

11 Claims, 32 Drawing Sheets

Related U.S. Application Data

(60) Provisional application No. 63/033,176, filed on Jun. 1, 2020.

(56) References Cited

U.S. PATENT DOCUMENTS

| | | | |
|---|---|---|---|
| 6,083,693 | A | 7/2000 | Nandabalan et al. |
| 6,187,535 | B1 | 2/2001 | Legrain et al. |
| 6,395,478 | B1 | 5/2002 | Nandabalan et al. |
| 6,410,239 | B1 | 6/2002 | Nandabalan et al. |
| 6,423,538 | B1 | 7/2002 | Wittrup et al. |
| 6,531,284 | B1 | 3/2003 | Legrain et al. |
| 6,828,112 | B2 | 12/2004 | Manfredi et al. |
| 6,841,352 | B2 | 1/2005 | Ostanin |
| 6,913,886 | B2 | 7/2005 | Legrain et al. |
| 9,005,927 | B2 | 4/2015 | Hufton et al. |
| 9,034,601 | B2 | 5/2015 | Hufton et al. |
| 9,139,637 | B2 | 9/2015 | Wittrup et al. |
| 9,249,410 | B2 | 2/2016 | Hill et al. |
| 10,017,758 | B1 | 7/2018 | Peikon et al. |
| 10,385,332 | B2 | 8/2019 | Hill et al. |
| 10,876,107 | B2 | 12/2020 | Vigneault et al. |
| 10,988,759 | B2 | 4/2021 | Baker et al. |
| 11,002,731 | B2 | 5/2021 | Pfeiffer et al. |
| 11,136,573 | B2 | 10/2021 | Baker et al. |
| 2003/0064477 | A1 | 4/2003 | Band et al. |
| 2003/0119002 | A1 | 6/2003 | Nandabalan et al. |
| 2005/0196743 | A1 | 9/2005 | Ostanin et al. |
| 2005/0251871 | A1 | 11/2005 | Chiaur et al. |
| 2008/0176756 | A1 | 7/2008 | Siegel et al. |
| 2009/0208973 | A1 | 8/2009 | Pagano |
| 2010/0075326 | A1 | 3/2010 | Jin et al. |
| 2011/0071046 | A1 | 3/2011 | Holt et al. |
| 2013/0008507 | A1 | 1/2013 | Ko |
| 2013/0085072 | A1 | 4/2013 | Bradbury et al. |
| 2017/0205421 | A1 | 7/2017 | Baker et al. |
| 2021/0054365 | A1 | 2/2021 | Baker et al. |
| 2021/0147831 | A1 | 5/2021 | Zhang et al. |
| 2022/0025356 | A1 | 1/2022 | Baker et al. |

FOREIGN PATENT DOCUMENTS

| | | |
|---|---|---|
| EP | 1677113 A1 | 7/2008 |
| EP | 2436766 A1 | 4/2012 |
| WO | 2002/086120 | 3/2002 |
| WO | 2007/145661 | 12/2007 |
| WO | 2011/092233 | 8/2011 |
| WO | 2021/231013 | 11/2021 |
| WO | 2021/247572 | 12/2021 |

OTHER PUBLICATIONS

Dura et al., "Spatially and temporally controlled immune cell interactions using microscale tools," Current Opinion in Immunology 35 (2015): 23-29.
Lipke, et al., "Sexual Agglutination in Budding Yeasts: Structure, Function, and Regulation of Adhesion Glycoproteins," Microbiological Reviews (1992): 180-194.
Pettersen et al., "UCSF ChimeraX: Structure visualization for researchers, educators, and developers," Protein Science 30.1 (2021): 70-82.
Maute et al., "Engineering high-affinity PD-1 variants for optimized immunotherapy and immuno-PET imaging," Proceedings of the National Academy of Sciences 112.47 (2015): E6506-E6514.
Atschul et al., "Basic local alignment search tool," Journal of Molecular Biology 215.3: 403-410 (1990).
Amarasinghe et al., "Opportunities and challenges in long-read sequencing data analysis," Genome Biology 21: 1-16 (2020).
Younger et al., "High-throughput characterization of protein-protein interactions by reprogramming yeast mating," Proceedings of the National Academy of Sciences 114: 12166-12171 (2017).
Fields et al., "A novel genetic system to detect protein-protein interactions," Nature 340, 245-246 (1989). https://doi.org/10.1038/340245a0.
Yu et al., "Next-generation sequencing to generate interactome datasets," Nature Methods 8(6): 478-480 (2011).
Hastie et al., "Yeast two-hybrid interaction partner screening through in vivo Cre-mediated Binary Interaction Tag generation," Nucleic Acids Research 35(21): e141 (2007).
Yachie et al., "Pooled-matrix protein interaction screens using Barcode Fusion Genetics," Molecular Systems Biology 12:863 (2016).
Chen et al., "Exhaustive benchmarking of the yeast two-hybrid system," Nat Methods 7, 667-668 (2010). https://doi.org/10.1038/nmeth0910-667.
Braun et al., "An experimentally derived confidence score for binary protein-protein interactions." Nature Methods 6(1): 91-97.
Smith, "Filamentous Fusion Phage: Novel Expression Vectors That Display Cloned Antigens on the Virion Surface," Science 228:1315-1317 (1985). https://doi.org/10.1126/science.4001944.
Boder et al., "Yeast surface display for screening combinatorial polypeptide libraries," Nature Biotechnology 15:553-557 (1997).
Perfetto et al., "Seventeen-colour flow cytometry: unravelling the immune system," Nat. Rev. Immunol. 4:648-655 (2004).
Gu et al., "Multiplex single-molecule interaction profiling of DNA-barcoded proteins," Nature 515:554-557 (2014). https://doi.org/10.1038/nature13761.
Roy et al., "The AGA1 product is involved in cell surface attachment of the *Saccharomyces cerevisiae* cell adhesion glycoprotein a-agglutinin," Molecular and Cellular Biology 11(8): 4196-4206 (1991).
Dranginis et al., "A Biochemical Guide to Yeast Adhesins: Glycoproteins for Social and Antisocial Occasions," Microbiology and Molecular Biology Reviews, 71(2): 282-294 (2007).
Zhao et al., "Interaction of a-Agglutinin and a-Agglutinin, *Saccharomyces cerevisiae* Sexual Cell Adhesion Molecules," Journal of Bacteriology, 183(9):2874-2880 (2001).
Herskowitz, "Life cycle of the budding yeast *Saccharomyces cerevisiae*," Microbiological Reviews 52(4): 536-553 (1988).
Boder et al., "Directed evolution of antibody fragments with monovalent femtomolar antigen-binding affinity," Proceedings of the National Academy of Sciences 97(20): 10701-10705 (2000).
Huang et al., "Secretion and Surface Display of Green Fluorescent Protein Using the Yeast *Saccharomyces cerevisiae*," Biotechnol Progress, 21: 349-357 (2005). https://doi.org/10.1021/bp0497482.
Kim et al., "Directed evolution of the epidermal growth factor receptor extracellular domain for expression in yeast," Proteins 62(4): 1026-1035 (2006).
Adams et al., "The Bcl-2 Protein Family: Arbiters of Cell Survival," Science 281:1322-1326 (1998). https://doi.org/10.1126/science.281.5381.1322.
Chen et al., "Differential Targeting of Prosurvival Bcl-2 Proteins by Their BH3-Only Ligands Allows Complementary Apoptotic Function," Molecular Cell 17: 393-403 (2005).
Procko et al., "A Computationally Designed Inhibitor of an Epstein-Barr Viral Bcl-2 Protein Induces Apoptosis in Infected Cells." Cell, 157:1644-1656 (2014).
Berger et al. "Computationally designed high specificity inhibitors delineate the roles of BCL2 family proteins in cancer," eLife 5:e20352 (2016).
McIsaac et al., "Synthetic gene expression perturbation systems with rapid, tunable, single-gene specificity in yeast," Nucleic Acids Research 41(4): e57 (2013).
Day et al., "Solution structure of prosurvival Mcl-1 and characterization of its binding by proapoptotic BH3-only ligands," Journal of Biological Chemistry 280:4738-4744 (2005).
Sauer et al., "Site-specific DNA recombination in mammalian cells by the Cre recombinase of bacteriophage P1," Proceedings of the National Academy of Sciences 85: 5166-5170 (1988).
Louvion et al., "Fusion of GAL4-VP16 to a steroid-binding domain provides a tool for gratuitous induction of galactose-responsive genes in yeast," Gene, vol. 131, Issue 1, pp. 129-134 (1993). https://doi.org/10.1016/0378-1119(93)90681-R.

(56) References Cited

OTHER PUBLICATIONS

Gibson et al. "Enzymatic assembly of DNA molecules up to several hundred kilobases," Nature Methods 6: 343-345 (2009).
Sanger et al., "DNA sequencing with chain-terminating inhibitors," Proceedings of the National Academy of Sciences 74: 5463-5467 (1977).
Araki et al., "Site-directed integration of the cre gene mediated by Cre recombinase using a combination of mutant lox sites," Nucleic Acids Research 30: e103 (2002).
Bentley et al., "Accurate whole human genome sequencing using reversible terminator chemistry," Nature 456: 53-59 (2008).
Van Delft et al., "How the Bcl-2 family of proteins interact to regulate apoptosis," Cell Research 16:203-213 (2006).
Lee et al., "A highly characterized yeast toolkit for modular, multipart assembly," ACS Synthetic Biology 4: 975-986 (2015).
Wingler et al., "Reiterative recombination for the in vivo assembly of libraries of multigene pathways," Proceedings of the National Academy of Sciences 108: 15135-15140 (2011).
Gai et al., "Yeast surface display for protein engineering and characterization," Current Opinion in Structural Biology 17: 467-473 (2007).
Wadle et al., "Serological identification of breast cancer-related antigens from a *Saccharomyces cerevisiae* surface display library," International Journal of Cancer 117: 104-113 (2005).
van den Beucken et al., "Affinity maturation of Fab antibody fragments by fluorescent-activated cell sorting of yeast-displayed libraries," FEBS Letters 546: 288-294 (2003).
Strauch et al., "Computational design of a pH-sensitive IgG binding protein," Proceedings of the National Academy of Sciences 111: 675-680 (2014).
Lee et al., "Bioengineered protein-based nanocage for drug delivery," Advanced Drug Delivery Reviews 106: 157-171 (2016). https//doi.org/10.1016/j.addr.2016.03.002.
Wells et al., "Reaching for high-hanging fruit in drug discovery at protein-protein interfaces," Nature 450: 1001-1009 (2007).
Xie et al., "Accelerated and adaptive evolution of yeast sexual adhesins," Molecular Biology and Evolution 28: 3127-3137 (2011).
Balagaddé et al., "A synthetic *Escherichia coli* predator-prey ecosystem," Molecular Systems Biology 4: 187, 8 pages (2008).
Gietz, et al., "High-efficiency yeast transformation using the LiAc/SS carrier DNA/PEG method," Nature Protocols 2: 31-34 (2007).
Boeke et al., "A positive selection for mutants lacking orotidine-5'-phosphate decarboxylase activity in yeast: 5-fluoro-orotic acid resistance," Molecular and General Genetics 197: 345-346 (1984).
Tanaka et al., "Recent developments in yeast cell surface display toward extended applications in biotechnology," Applied Microbiology & Biotechnology, vol. 95, No. 3, pp. 577-591 (2012).
Terrance et al., "Sexual agglutination in *Saccharomyces cerevisiae*," Journal of Bacteriology, vol. 148, No. 3, pp. 389-896 (1981).
Thompson et al., "SYNZIP protein interaction toolbox: in vitro and in vivo specifications of heterospecific coiled-coil interaction domains," ACS Synthetic Biology, vol. 1, No. 4, pp. 118-129 (2012).
Vidal, "Interactome modeling," FEBS Letters, vol. 579, No. 8, pp. 1834-1838 (2005).
Wahlbom et al., "Molecular analysis of a *Saccharomyces cerevisiae* mutant with improved ability to utilize xylose shows enhanced expression of proteins involved in transport, initial xylose metabolism, and the pentose phosphate pathway," Applied and Environmental Microbiology, vol. 69, No. 2, pp. 740-746 (2003).
Wang et al., "A modular cell-based biosensor using engineered genetic logic circuits to detect and integrate multiple environmental signals," Biosensors and Bioelectronics, vol. 40, No. 1, pp. 368-376 (2013).
Wang et al., "Three-dimensional reconstruction of protein networks provides insight into human genetic disease," Nature Biotechnology, vol. 30, No. 2, pp. 159-164 (2012).
Weaver-Feldhaus et al., "Yeast mating for combinatorial Fab library generation and surface display," FEBS Letters, vol. 564, pp. 24-34 (2004).
Weber et al., "Emerging biomedical applications of synthetic biology," Nature Reviews Genetics, vol. 13, No. 1, pp. 21-35 (2012).
Wen et al., "Yeast surface display of trifunctional minicellulosomes for simultaneous saccharification and fermentation of cellulose to ethanol," Applied and Environmental Microbiology, vol. 76, No. 4, pp. 1251-1260 (2010).
Wilson et al., "The LoxP/CRE system and genome modification," Gene Knockout Protocols, Humana Press, pp. 83-94 (2001).
Yu et al., "High-quality binary protein interaction map of the yeast interactome network." Science, vol. 322, No. 5898, pp. 104-110 (2008).
Haber, "Bisexual Mating Behavior in a Diploid of *Saccharomyces cerevisiae*: Evidence for Genetically Controlled Non-Random Chromosome Loss During Vegetative Growth," Genetics, vol. 78, pp. 843-858 (1974).
Goossens et al., "Molecular Mechanism of Flocculation Self-Recognition in Yeast and Its Role in Mating and Survival," mBio vol. 6, No. 2, e00427-15, pp. 1-16 (2015).
Suzuki, "Roles of sexual cell agglutination in yeast mass mating," Genes Genet. Syst., vol. 78, pp. 211-219 (2003).
Diener et al., "Yeast mating and image-bsed quantification of spatial pattern formation," PLOS Computational Biology, 10: e1003690, 14 pages (2014).
International Search Report and Written Opinion issued in International Application No. PCT/US2021/027111 dated Jul. 12, 2021.
International Search Report and Written Opinion issued in International Application No. PCT/US2021/035246 dated Nov. 3, 2021.
Hughes, et al., "Molecular recognition of ternary complexes: a new dimension in the structure-guided design of chemical degraders", Essays in Biochemistry, vol. 61, No. 5, pp. 505-516 (2017).
Lööke et al., "Extraction of genomic DNA from yeasts for PCR-based applications," Biotechniques 50: 325-328 (2011).
Banta, "Replacing Antibodies: Engineering New Binding Proteins" Annual Review of Biomedical Engineering, vol. 15, pp. 93-113 (2013).
Barton et al., "Why sex and recombination?" Science 281.5385, pp. 1986-1990 (1998).
Bender et al., "Pheromones and pheromone receptors are the primary determinants of mating specificity in the yeast *Saccharomyces cerevisiae*," Genetics, vol. 121, pp. 463-476 (1989).
Boder et al., "Yeast surface display of a noncovalent MHC class II heterodimer complexed with antigenic peptide," Biotechnology and Bioengineering, vol. 92, No. 4, pp. 485-491 (2005). https://doi.org/10.1002/bit.20616.
Boder et al., "Yeast surface display system for antibody engineering," Immunotechnology, vol. 2.4, p. 283 (1996).
Cappellaro et al., "Mating type-specific cell-cell recognition of *Saccharomyces cerevisiae*: cell wall attachment and active sites of a- and alpha-agglutinin," EMBO Journal, vol. 13, No. 20, pp. 4737-4744 (1994).
Cardinale et al., "Contextualizing context for synthetic biology-identifying causes of failure of synthetic biological systems," Biotechnology Journal, vol. 7, pp. 7, pp. 856-866 (2012).
Casini et al., "R2oDNA designer: computational design of biologically neutral synthetic DNA Sequences." ACS Synthetic Biology, vol. 3, No. 8, pp. 525-528 (2014).
Chan et al., "Isolation and genetic analysis of *Saccharomyces cerevisiae* mutants supersensitive to G1 arrest by a factor and alpha factor pheromones," Molecular and Cellular Biology, vol. 2, No. 1, pp. 11-20 (1982).
Chao et al., "Fine epitope mapping of anti-epidermal growth factor receptor antibodies through random mutagenesis and yeast surface display," Journal of molecular biology, vol. 342, No. 2, pp. 539-550 (2004).
Chee et al., "New and redesigned pRS plasmid shuttle vectors for genetic manipulation of *Saccharomyces cerevisiae*," G3: Genes | Genomes | Genetics, vol. 2, No. 5, pp. 515-526 (2012).
Chen, et al., "Cell-cell fusion," FEBS letters, vol. 581, No. 11, pp. 2181-2193 (2007).
Chenevert et al., "Identification of genes required for normal pheromone-induced cell polarization in *Saccharomyces cerevisiae*," Genetics, vol. 136, No. 4, pp. 1287-1296 (1994).

(56) References Cited

OTHER PUBLICATIONS

Cherf et al., "Applications of yeast surface display for protein engineering", Methods in Molecular Biology, vol. 1319, pp. 155-175 (2015).
Colegrave, "Sex releases the speed limit on evolution," Nature, vol. 420, No. 6916, pp. 664-666 (2002).
Daar et al., "Top ten biotechnologies for improving health in developing countries," Nature Genetics, vol. 32, No. 2, pp. 229-232 (2002).
Daniel et al., "Synthetic analog computation in living cells," Nature, vol. 497, pp. 619-623 (2013).
Daugherty et al., "Antibody affinity maturation using bacterial surface display," Protein Engineering, vol. 11, No. 9, pp. 325-832 (1998).
Dunham, "Synthetic ecology: a model system for cooperation," Proceedings of the National Academy of Sciences, vol. 104, No. 6, pp. 1741-1742 (2007).
Dunn et al., "Natural and sexual selection act on different axes of variation in avian plumage color," Science Advances, vol. 1.2, e1400155, 7 pages (2015).
Eby et al., "Characterization, performance, and applications of a yeast surface display-based biocatalyst", RSC Advances, vol. 5, pp. 19166-19175 (2015).
Fletcher et al., "A basis set of de novo coiled-coil peptide oligomers for rational protein design and synthetic biology," ACS Synthetic Biology, vol. 1, pp. 240-250 (2012).
Gera et al., "Protein selection using yeast surface display," Methods. vol. 60, No. 1, pp. 15-26 (2013).
Greig et al., "Hybrid speciation in experimental populations of yeast," Science, vol. 298, pp. 1773-1775 (2002).
Guo et al., "A *Saccharomyces* gene family involved in invasive growth, cell-cell adhesion, and mating," Proceedings of the National Academy of Sciences, vol. 97, No. 22, pp. 12158-12163 (2000).
Haber, "Mating-type genes and MAT switching in *Saccharomyces cerevisiae*," Genetics, vol. 191, pp. 33-64 (2012).
Head et al., "Female mate preferences for male body size and shape promote sexual isolation in threespine sticklebacks," Ecology and Evolution, vol. 3, pp. 2183-2196 (2013).
Howitt et al., "Technologies for global health," The Lancet, vol. 380, pp. 507-535 (2012).
Huang et al., "Conserved WCPL and CX4C domains mediate several mating adhesin interactions in *Saccharomyces cerevisiae*," Genetics, vol. 182, pp. 173-189 (2009).
Ito et al., "Transformation of intact yeast cells treated with alkali cations,"Journal of Bacteriology, vol. 153, No. 1, pp. 163-168 (1983).
Jackson et al., "Courtship in *Saccharomyces cerevisiae*: an early cell-cell interaction during mating," Molecular and Cellular Biology, vol. 10, No. 5, pp. 2202-2213 (1990).
James et al., "Biophysical mechanism of T-cell receptor triggering in a reconstituted system," Nature, vol. 487, pp. 64-69 (2012).
Kaster et al., "Hygromycin B resistance as dominant selectable marker in yeast," Current Genetics, vol. 8, pp. 1984, pp. 353-358 (1984).
Keddar et al., "Color ornaments and territory position in king penguins," Behavioural Processes, vol. 119, pp. 32-37, (2015).
Khakhar et al., "Cell-Cell Communication in Yeast Using Auxin Biosynthesis and Auxin Responsive CRISPR Transcription Factors," ACS Synthetic Biology (2015).
Malleshaiah et al., "The scaffold protein Ste5 directly controls a switch-like mating decision in yeast," Nature, vol. 465, pp. 101-105 (2010).
Martins et al., "Evolution and stability of ring species," Proceedings of the National Academy of Sciences, vol. 110, No. 13, pp. 5080-5084 (2013).
Miura et al., "Enzyme evolution by yeast cell surface engineering", Methods in Molecular Biology, vol. 1319, pp. 217-232 (2015).
Nasmyth, "Molecular genetics of yeast mating type," Annual Review of Genetics, vol. 16, pp. 439-500 (1982).
Parrish et al., "Yeast two-hybrid contributions to interactome mapping," Current Opinion in Biotechnology, vol. 17, pp. 387-393 (2006).
Put et al., "The heat resistance of ascospores of four *Saccharomyces* spp. isolated from spoiled heat-processed soft drinks and fruit products," Journal of Applied Bacteriology, vol. 52, No. 2, pp. 235-243 (1982).
Richman et al., "Biosensor detection systems: engineering stable, high-affinity bioreceptors by yeast surface display," Methods in Molecular Biology, vol. 504, pp. 323-350 (2009).
Rodriguez et al., "Diversification under sexual selection: the relative roles of mate preference strength and the degree of divergence in mate preferences," Ecology Letters, vol. 16, No. 8, pp. 964-974 (2013).
Safran et al., "Contributions of natural and sexual selection to the evolution of premating reproductive isolation: a research agenda," Trends in Ecology & Evolution, vol. 28, No. 11, pp. 643-650 (2013).
Sauer, "Functional expression of the cre-lox site-specific recombination system in the yeast *Saccharomyces cerevisiae*," Molecular and Cellular Biology, vol. 7, No. 6, pp. 2087-2096 (1987).
Segall, "Polarization of yeast cells in spatial gradients of alpha mating factor," Proceedings of the National Academy of Sciences, vol. 90, No. 18, pp. 8332-8336 (1993).
Shou et al., "Synthetic cooperation in engineered yeast populations," Proceedings of the National Academy of Sciences, vol. 104, No. 6, pp. 1877-1882 (2007).
Sreekrishna et al., "Construction of strains of *Saccharomyces cerevisiae* that grow on lactose," Proceedings of the National Academy of Sciences, vol. 82, No. 23, pp. 7909-7913 (1985).
Sundstrom, "Adhesins in Candida albicans," Current Opinion in Microbiology, vol. 2, No. 4, pp. 353-357 (1999).

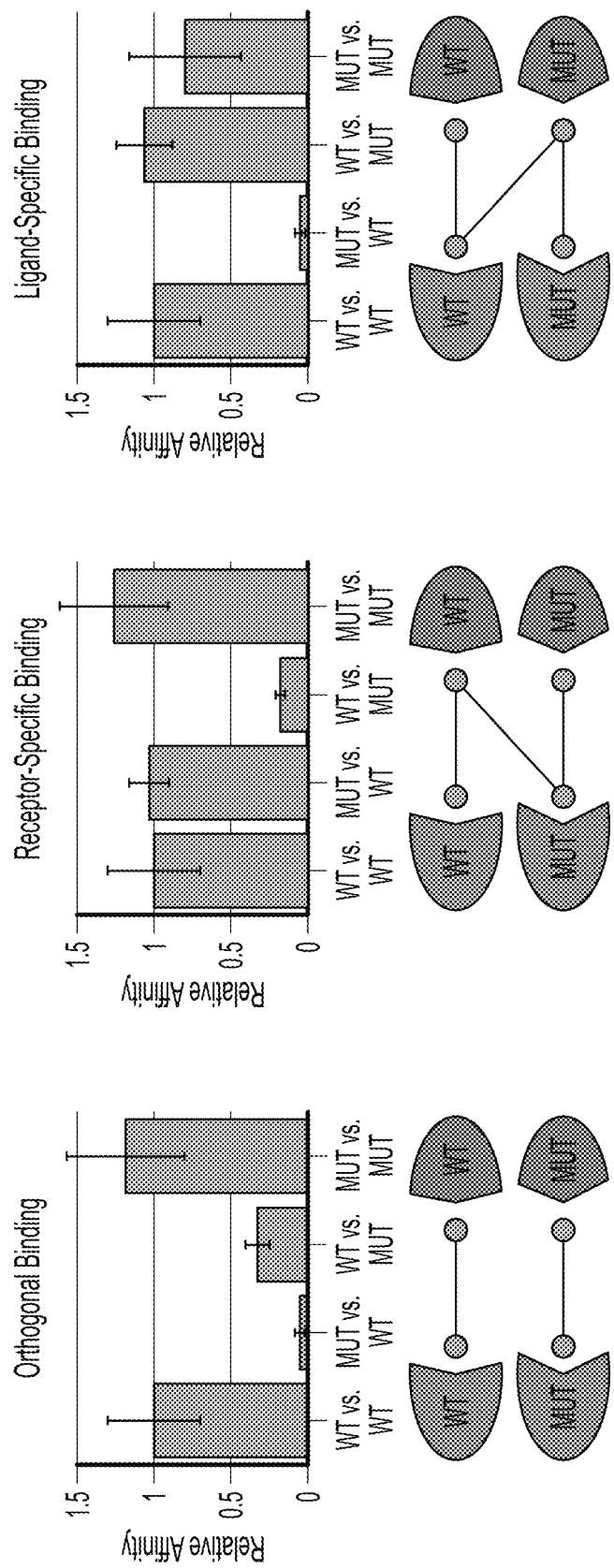

| 1300 pd1mutant | 1302 pembromutant | 1304 min_distance | pembrowt_RelAffinity | pembrowt_RelAffinity_cv | pembrowt_RelAffinity_sd | pd1wt_RelAffinity |
|---|---|---|---|---|---|---|
| 54_K_F | 33_Y_P | 2.989 | 0.050277848 | 0.679422876 | 0.03415992 | 0.326242632 |
| 54_K_F | 101_Y_K | 3.891 | 0.050277848 | 0.679422876 | 0.03415992 | 1.06203686 |
| 54_K_F | 101_Y_A | 3.891 | 0.050277848 | 0.679422876 | 0.03415992 | 1.163136226 |
| 63_S_G | 235_L_F | 3.969 | 0.877988116 | 0.143936012 | 0.126374108 | 0.196788621 |
| 42_N_F | 101_Y_W | 5.358 | 1.030942691 | 0.125815366 | 0.129708433 | 0.179094539 |
| 53_D_R | 52_N_D | 6.596 | 0.221540931 | 0.25969223 | 0.057532459 | 1.043986476 |
| 54_K_T | 101_Y_A | 3.891 | 0.111329258 | 0.512250528 | 0.057028471 | 1.163136226 |
| 54_K_T | 101_Y_H | 3.891 | 0.111329258 | 0.512250528 | 0.057028471 | 0.842878305 |
| 54_K_L | 101_Y_K | 3.891 | 0.144259856 | 0.319145646 | 0.046039905 | 1.06203686 |
| 54_K_T | 101_Y_K | 3.891 | 0.111329258 | 0.512250528 | 0.057028471 | 1.06203686 |
| 54_K_M | 33_Y_P | 2.989 | 0.488963818 | 0.204828599 | 0.100153774 | 0.326242632 |
| 42_N_Y | 101_Y_W | 5.358 | 0.914765793 | 0.062431653 | 0.057110341 | 0.179094539 |
| 54_K_I | 101_Y_K | 3.891 | 0.403507074 | 0.556774162 | 0.224662313 | 1.06203686 |
| 42_N_S | 102_R_N | 3.161 | 0.598580424 | 0.253487983 | 0.151732944 | 0.393170954 |
| 53_D_H | 52_N_D | 6.596 | 0.647231962 | 0.1994037 | 0.129060448 | 1.043986476 |
| 53_D_A | 52_N_D | 6.596 | 0.486744553 | 0.184617662 | 0.089861641 | 1.043986476 |
| 53_D_A | 55_N_D | 6.033 | 0.486744553 | 0.184617662 | 0.089861641 | 0.622861289 |
| 54_K_I | 101_Y_A | 3.891 | 0.403507074 | 0.556774162 | 0.224662313 | 1.163136226 |
| 63_S_I | 235_L_V | 3.969 | 0.759391785 | 0.189134444 | 0.143627143 | 0.509330448 |
| 53_D_Q | 52_N_D | 6.596 | 0.566224805 | 0.263671264 | 0.14929721 | 1.043986476 |
| 63_S_L | 235_L_V | 3.969 | 0.653664534 | 0.146093105 | 0.095495881 | 0.509330448 |
| 63_S_Y | 55_N_D | 6.033 | 0.61142629 | 0.144681335 | 0.084461972 | 0.622861289 |
| 53_D_W | 52_N_D | 6.596 | 0.808666161 | 0.199595892 | 0.161406443 | 1.043986476 |
| 53_D_T | 52_N_D | 6.596 | 0.681228304 | 0.36806923 | 0.250739177 | 1.043986476 |

FIG. 13

| pd1wt_RelAffinity_cv | pd1wt_RelAffinity_sd | expected | expected_cv | RelativeAffinity | cv | sd |
|---|---|---|---|---|---|---|
| 0.243474363 | 0.079431717 | 0.016402778 | 0.721730704 | 1.185509641 | 0.321172703 | 0.380753336 |
| 0.171615023 | 0.18226148 | 0.053396928 | 0.700761843 | 0.798894442 | 0.454746789 | 0.363294682 |
| 0.057943902 | 0.067396652 | 0.058479987 | 0.681889243 | 0.606955466 | 0.361034876 | 0.219132091 |
| 0.16225945 | 0.031930813 | 0.172778071 | 0.216900218 | 1.346998398 | 0.27860899 | 0.375285863 |
| 0.160287563 | 0.028706627 | 0.184636206 | 0.203768519 | 1.259604233 | 0.279578106 | 0.352157766 |
| 0.08853763 | 0.092432088 | 0.231285736 | 0.274370127 | 1.414814508 | 0.301801068 | 0.42699253 |
| 0.057943902 | 0.067396652 | 0.129491093 | 0.515517312 | 0.704763212 | 0.358712701 | 0.252807515 |
| 0.090915615 | 0.076630799 | 0.093837016 | 0.520255949 | 0.506745263 | 0.311711231 | 0.15795819 |
| 0.171615023 | 0.18226148 | 0.153209285 | 0.362361227 | 0.807476026 | 0.184408488 | 0.148905433 |
| 0.171615023 | 0.18226148 | 0.118235776 | 0.540233578 | 0.622144294 | 0.180939386 | 0.112570406 |
| 0.243474363 | 0.079431717 | 0.159520843 | 0.318173727 | 0.813614816 | 0.418292677 | 0.34032912 |
| 0.160287563 | 0.028706627 | 0.163829558 | 0.172016901 | 0.79219244 | 0.403043663 | 0.319288143 |
| 0.171615023 | 0.18226148 | 0.428539385 | 0.582622677 | 1.871340093 | 0.185023865 | 0.34624577 |
| 0.290621623 | 0.114263981 | 0.235344436 | 0.385638542 | 0.940999175 | 0.270183375 | 0.254242332 |
| 0.08853763 | 0.092432088 | 0.675701415 | 0.218175955 | 2.387134891 | 0.322909232 | 0.770827895 |
| 0.08853763 | 0.092432088 | 0.50815473 | 0.204750075 | 1.756660225 | 0.203497318 | 0.357475644 |
| 0.173114034 | 0.10782603 | 0.30317434 | 0.253085262 | 1.019179092 | 0.362876722 | 0.369836369 |
| 0.057943902 | 0.067396652 | 0.469333695 | 0.559781175 | 1.561733334 | 0.464401875 | 0.725271888 |
| 0.392954737 | 0.200143812 | 0.386781358 | 0.436102354 | 1.223283851 | 0.446510981 | 0.546209673 |
| 0.08853763 | 0.092432088 | 0.591131039 | 0.278139259 | 1.832802859 | 0.043183996 | 0.079147751 |
| 0.392954737 | 0.200143812 | 0.33293125 | 0.419233372 | 1.008524666 | 0.374988793 | 0.378185448 |
| 0.173114034 | 0.10782603 | 0.380833767 | 0.225612849 | 1.140537814 | 0.135927787 | 0.155030781 |
| 0.08853763 | 0.092432088 | 0.844236536 | 0.218351624 | 2.48334669 | 0.303669274 | 0.754116087 |
| 0.08853763 | 0.092432088 | 0.711193137 | 0.378568184 | 2.052038975 | 0.283505021 | 0.581763352 |

FIG. 13 (Cont.)

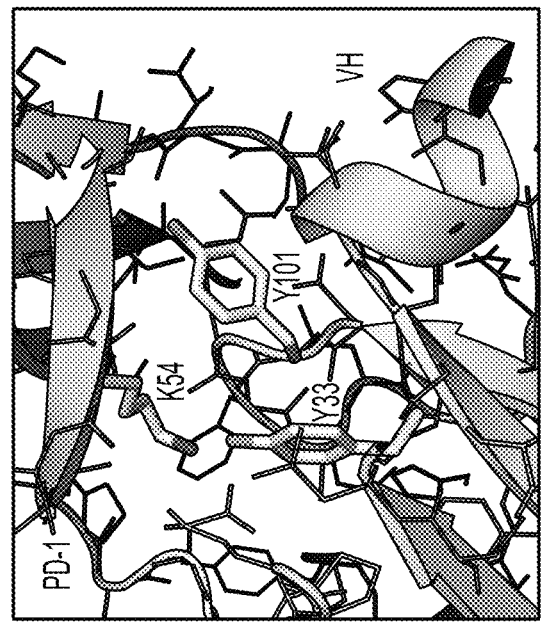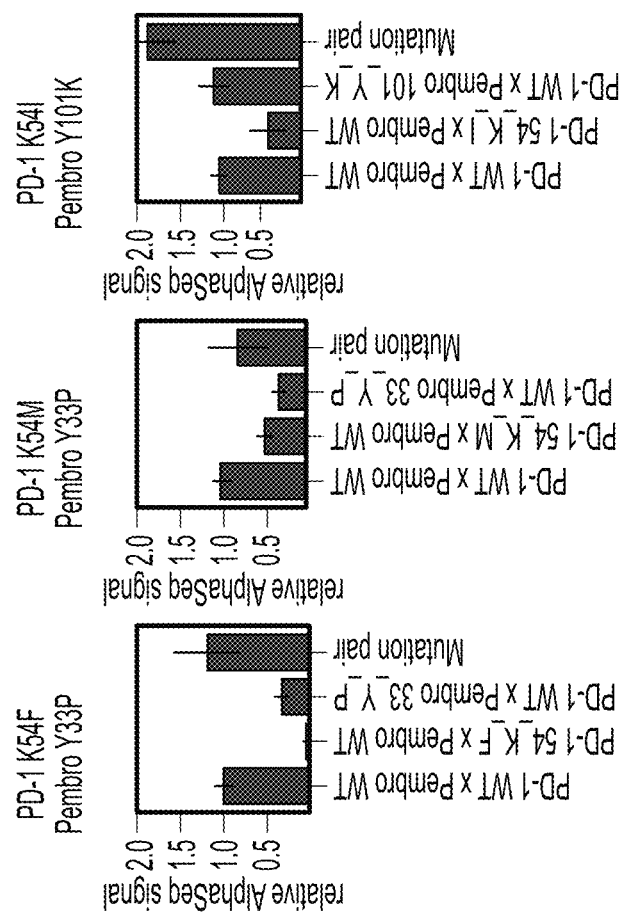
FIG. 16

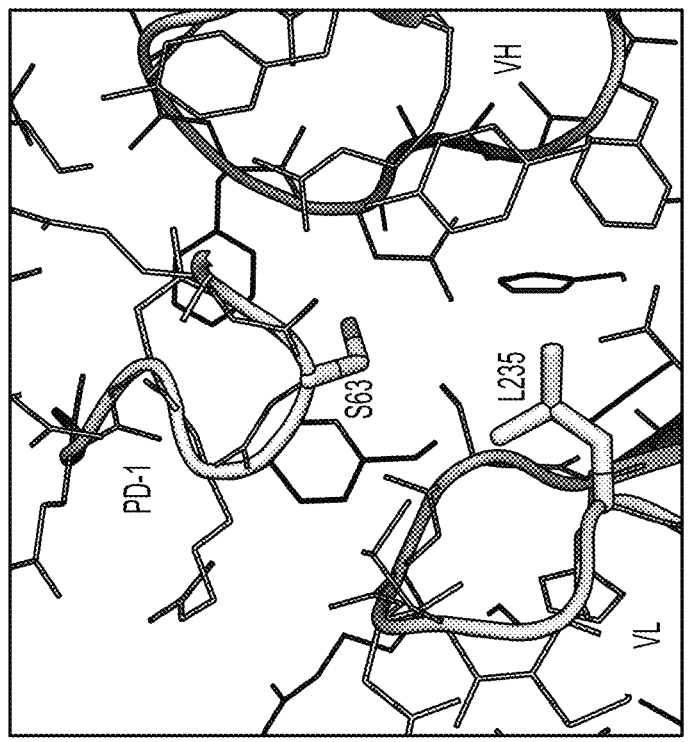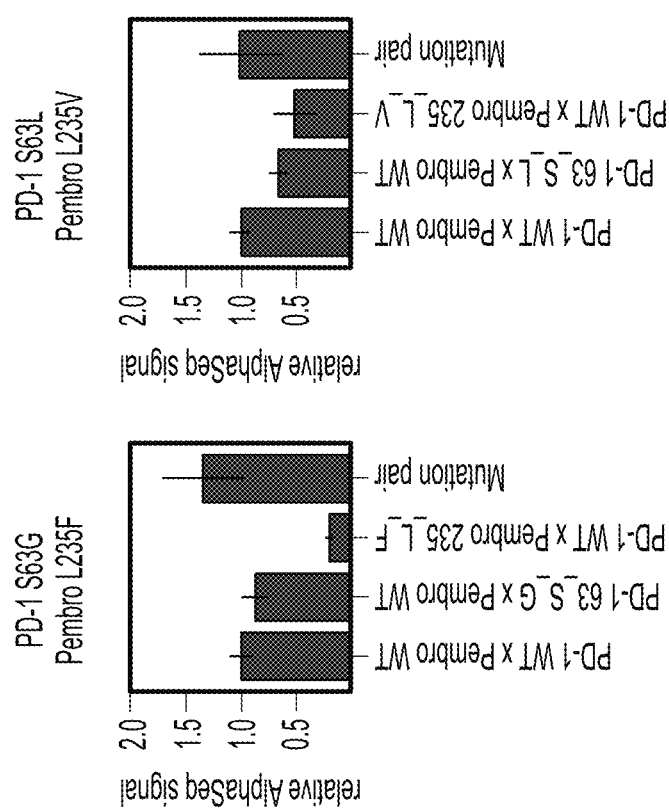
FIG. 17

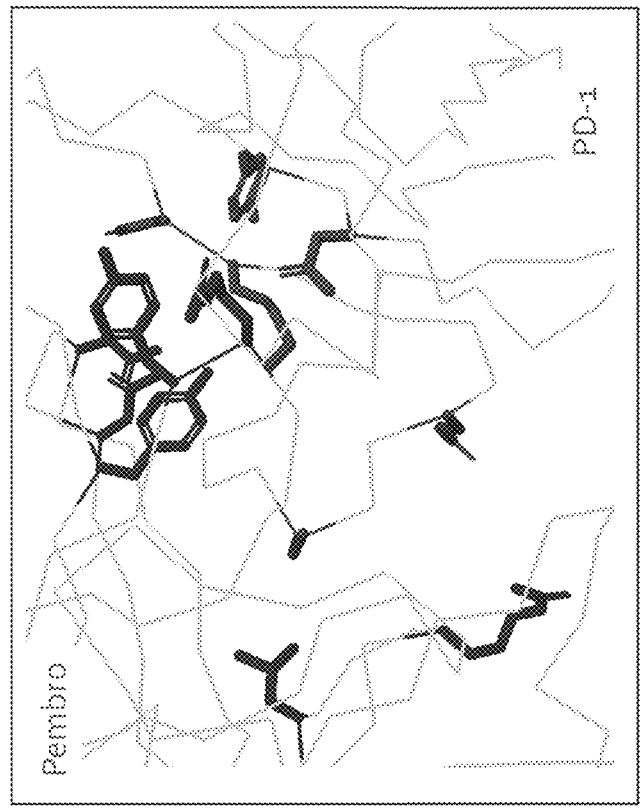
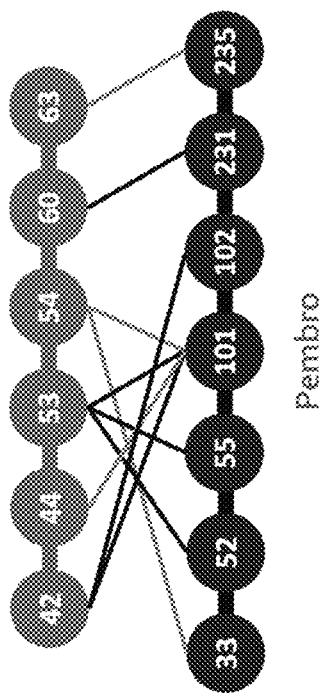
- Yield unique information about the protein-protein interface not available when using one-sided binding-based methods
- Indicator of structural proximity
  - useful as distance constraints to aid modeling efforts
FIG. 18

METHODS FOR CHARACTERIZING AND ENGINEERING PROTEIN-PROTEIN INTERACTIONS

RELATED APPLICATIONS

This application is a continuation of and claims priority to U.S. patent application Ser. No. 17/619,506, entitled "METHODS FOR CHARACTERIZING AND ENGINEERING PROTEIN-PROTEIN INTERACTIONS," filed Dec. 15, 2021, which is a U.S. National Stage Entry of International Application No. PCT/US2021/035246, entitled "METHODS FOR CHARACTERIZING AND ENGINEERING PROTEIN-PROTEIN INTERACTIONS," filed Jun. 1, 2021, which claims priority to U.S. Provisional Patent Application Ser. No. 63/033,176 filed Jun. 1, 2020. All above-identified applications are hereby incorporated by reference in their entireties.

BACKGROUND

Epitope mapping is the experimental process of characterizing the identity, amino acid composition, and conformational structure of the binding site of an antibody on its target antigen. Epitope mapping may be useful in the discovery and development of novel therapies, vaccines, diagnostics, among other biomedical applications. Epitope mapping can also be useful for securing intellectual property (IP) protection of, for example, novel therapeutic antibodies. Exhaustive characterization of the amino acid identity and conformational structure of a novel antibody's epitope helps define the novelty of the antibody, the non-obviousness of the antibody, and enables providing the required written descriptive support for disclosure of the novel antibody. Crowded IP spaces, for example, a therapeutic target for which multiple drugs already exist, require the ability to differentiate between a novel antibody and previously disclosed antibodies for the same target.

Likewise, paratope mapping is the characterization of the properties of an antibody that confer specificity to its antigen, for example amino acid compositions, charge, and three-dimensional conformation. Thorough characterization of the antibody-antigen interaction by both epitope and paratope mapping are useful for understanding the mechanisms and dynamics of specific binding between the antibody and antigen and can be used to gain structural insights into the binding interface. Methods for epitope and paratope mapping include array-based oligo-peptide scanning, site-directed mutagenesis mapping, high-throughput shotgun mutagenesis mapping, cross-linking-coupled mass spectrometry, among others.

More broadly, characterization of the binding dynamics at the interface between any two proteins that specifically interact plays a role in myriad biomedical applications. The methods disclosed herein may provide for the high-throughput characterization of the specific interaction at the interface between two protein binding partners. The methods disclosed herein utilize, in certain embodiments, a combination of exhaustive site saturation mutagenesis and high-throughput screening to comprehensively characterize the interactive surface of two protein binding partners simultaneously in a rapid cost-effective assay. The methods disclosed herein may be utilized for the characterization of any two protein binding partners, e.g., for simultaneous epitope and paratope mapping of an antibody and its antigen.

SUMMARY OF ILLUSTRATIVE EMBODIMENTS

The forgoing general description of the illustrative implementations and the following detailed description thereof are merely exemplary aspects of the teachings of this disclosure and are not restrictive.

In some implementations, the present invention provides a novel method for identifying compensatory mutations between two protein binding partners, the method, comprising:
providing a first library of protein binding partners, the first library of protein binding partners, comprising: a first wild-type polypeptide and a first plurality of mutant polypeptides;
providing a second library of protein binding partners, the second library of protein binding partners, comprising: a second wild-type polypeptide and a second plurality of mutant polypeptides;
measuring an observed affinity value between each protein binding partner of the first library of protein binding partners and each protein binding partner of the second library of protein binding partners;
identifying, based on the observed affinity value between each protein binding partner of the first library of protein binding partners and each protein binding partner of the second library of protein binding partners, one or more pairs of protein binding partners that have a respective observed affinity value that is substantially different than the observed affinity value between the first wild-type polypeptide and the second wild-type polypeptide.

In some implementations, the present invention provides a novel method for identifying compensatory mutations between two protein binding partners, the method comprising:
providing a library of first protein binding partners, the library of first protein binding partners, comprising: a first wild-type polypeptide and a first plurality of mutant polypeptides;
providing a library of second protein binding partners, the library of second protein binding partners, comprising: a second wild-type polypeptide and a second plurality of mutant polypeptides;
measuring an observed affinity value between each protein binding partner of the library of first protein binding partners and each protein binding partner of the library of second protein binding partners; and
identifying, based on the respective observed affinity value between each protein binding partner of the library of first protein binding partners and each protein binding partner of the library of second protein binding partners, one or more pairs of protein binding partners, comprising:
(i) one polypeptide of the first plurality of mutant polypeptides, and
(ii) one polypeptide of the second plurality of mutant polypeptides,
wherein the observed affinity value of each pair of the one or more pairs of protein binding partners is substantially different than a respective expected affinity value between the respective pair of protein binding partners,
wherein the expected affinity value, for a given pair of protein binding partners is calculated based on
a) the observed affinity value between the first wild-type polypeptide of the given pair and the one polypeptide of the second plurality of mutant polypeptides of the given pair, and b) the observed affinity value between the one polypeptide of the first plurality of mutant polypeptides of the given pair and the second wild-type polypeptide of the given pair.

BRIEF DESCRIPTION OF THE DRAWINGS

The accompanying drawings, which are incorporated in and constitute a part of the specification, illustrate one or more embodiments and, together with the description, explain these embodiments. The accompanying drawings have not necessarily been drawn to scale. Any values dimensions illustrated in the accompanying graphs and figures are for illustration purposes only and may or may not represent actual or preferred values or dimensions. Where applicable, some or all features may not be illustrated to assist in the description of underlying features. In the drawings:

FIG. 3A is a graphical representation of the interaction between two protein binding partners that exhibit orthogonal binding.

FIG. 3B is a graphical representation of the interaction between two protein binding partners that exhibit receptor-specific binding.

FIG. 3C is a graphical representation of the interaction between two protein binding partners that exhibit ligand-specific binding.

DETAILED DESCRIPTION OF ILLUSTRATIVE EMBODIMENTS

Figure 1:
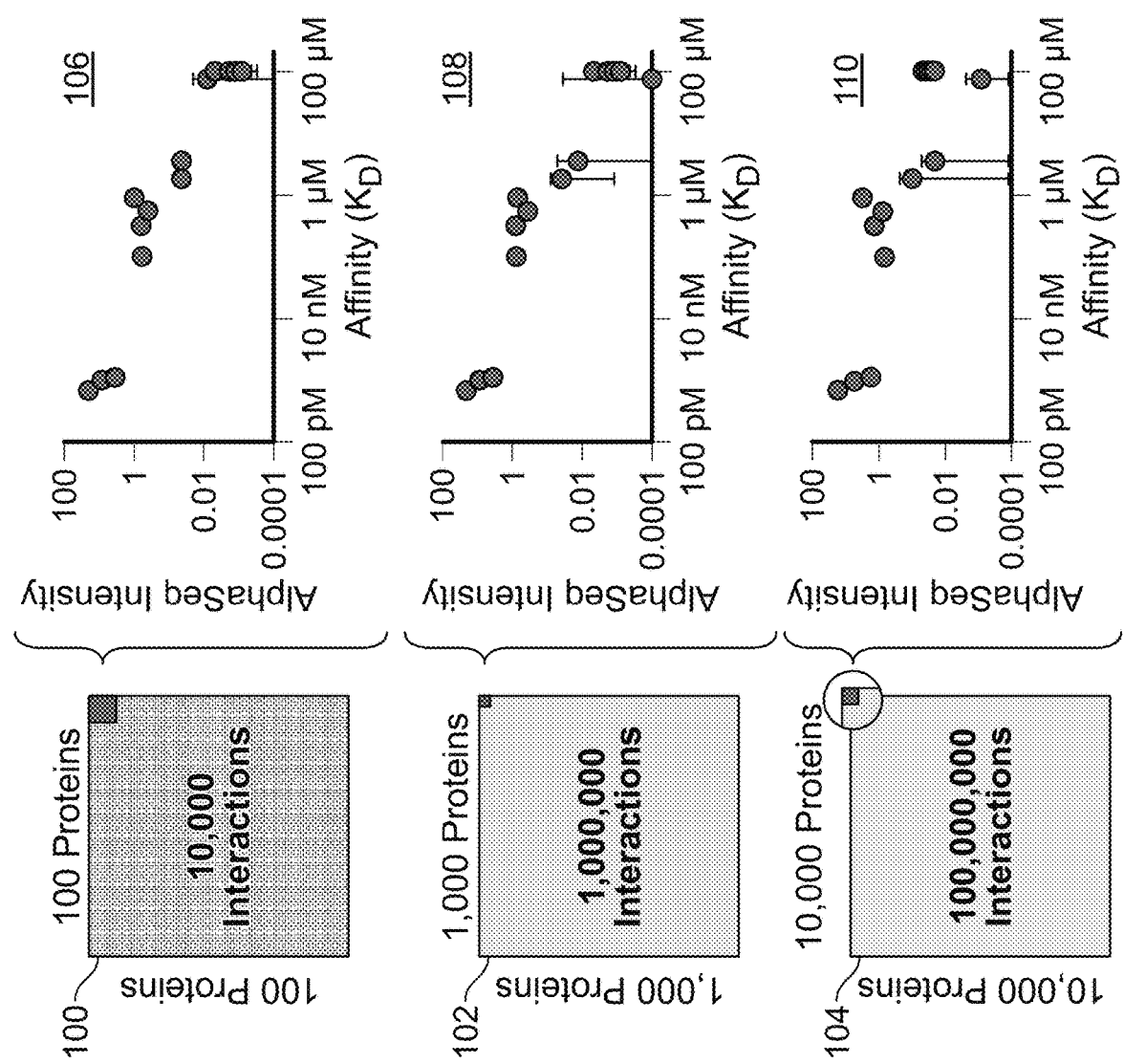
FIG. 1 is a series of charts showing the library-by-library screening capacity of the AlphaSeq® method.

The description set forth below in connection with the appended drawings is intended to be a description of various, illustrative embodiments of the disclosed subject matter. Specific features and functionalities are described in connection with each illustrative embodiment; however, it will be apparent to those skilled in the art that the disclosed embodiments may be practiced without each of those specific features and functionalities.

Reference throughout the specification to "one embodiment" or "an embodiment" or "one implementation" or "an implementation" means that a particular feature, structure, or characteristic described in connection with an embodiment or implementation is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments. Further, it is intended that embodiments of the disclosed subject matter cover modifications and variations thereof.

It must be noted that, as used in the specification and the appended claims, the singular forms "a," "an," and "the" include plural referents unless the context expressly dictates otherwise. That is, unless expressly specified otherwise, as used herein the words "a," "an," "the," and the like carry the meaning of "one or more." Additionally, it is to be understood that terms such as "left," "right," "top," "bottom," "front," "rear," "side," "height," "length," "width," "upper," "lower," "interior," "exterior," "inner," "outer," and the like that may be used herein merely describe points of reference and do not necessarily limit embodiments of the present disclosure to any particular orientation or configuration. Furthermore, terms such as "first," "second," "third," etc., merely identify one of a number of portions, components, steps, operations, functions, and/or points of reference as disclosed herein, and likewise do not necessarily limit embodiments of the present disclosure to any particular configuration or orientation.

Furthermore, the terms "approximately," "about," "proximate," "minor variation," and similar terms generally refer to ranges that include the identified value within a margin of 20%, 10% or preferably 5% in certain embodiments, and any values therebetween.

All of the functionalities described in connection with one embodiment are intended to be applicable to the additional embodiments described below except where expressly stated or where the feature or function is incompatible with the additional embodiments. For example, where a given feature or function is expressly described in connection with one embodiment but not expressly mentioned in connection with an alternative embodiment, it should be understood that the inventors intend that that feature or function may be deployed, utilized or implemented in connection with the alternative embodiment unless the feature or function is incompatible with the alternative embodiment.

The practice of the techniques described herein may employ, unless otherwise indicated, conventional techniques and descriptions of organic chemistry, polymer technology, molecular biology (including recombinant techniques), cell biology, cell culture, biochemistry, protein engineering, and sequencing technology, which are within the skill of those who practice in the art. Such conventional techniques include bacterial, fungal, and mammalian cell culture techniques and screening assays. Specific illustrations of suitable techniques can be had by reference to the examples herein. However, other equivalent conventional procedures can, of course, also be used. Such conventional techniques and descriptions can be found in standard laboratory manuals such as Green, et al., Eds. (1999), *Genome Analysis: A Laboratory Manual Series* (Vols. I-IV); Weiner, Gabriel, Stephens, Eds. (2007), *Genetic Variation: A Laboratory Manual*; Dieffenbach, Dveksler, Eds. (2003), PCR Primer: *A Laboratory Manual*; Bowtell and Sambrook (2003), *DNA Microarrays: A Molecular Cloning Manual*; Mount (2004), *Bioinformatics: Sequence and Genome Analysis*; Sambrook and Russell (2006), *Condensed Protocols from Molecular Cloning: A Laboratory Manual*; and Sambrook and Russell (2002), *Molecular Cloning: A Laboratory Manual* (all from Cold Spring Harbor Laboratory Press); Stryer, L. (1995) *Biochemistry* ($4^{th}$ Ed.) W.H. Freeman, New York N.Y.; Gait, "*Oligonucleotide Synthesis: A Practical Approach*" 1984, IRL Press, London; Nelson and Cox (2000), *Lehninger, Principles of Biochemistry* ($3^{rd}$ Ed.) W.H. Freeman Pub., New York, N.Y.; Berg et al. (2002) *Biochemistry* ($5^{th}$ Ed.) W.H. Freeman Pub., New York, N.Y.; all of which are herein incorporated in their entirety by reference for all purposes.

Unless defined otherwise, all technical and scientific terms used herein have the same meaning as commonly understood by one of ordinary skill in the art to which this invention belongs. All publications mentioned herein are incorporated by reference for the purpose of describing and disclosing devices, methods and cell populations that may be used in connection with the presently described invention.

The term "complementary nucleotides" as used herein refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" or "percent homology" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'; and the nucleotide sequence 3'-TCGA-5' is 100% complementary to a region of the nucleotide sequence 5'-TTAGCTGG-3'.

"Homology" or "identity" or "similarity" refers to sequence similarity between two peptides or, more often in the context of the present disclosure, between two nucleic acid molecules. The term "homologous region" or "homology arm" refers to a region on the donor DNA with a certain degree of homology with the target genomic DNA sequence. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences.

"Operably linked" refers to an arrangement of elements, e.g., barcode sequences, gene expression cassettes, coding sequences, promoters, enhancers, transcription factor binding sites, where the components so described are configured so as to perform their usual function. Thus, control sequences operably linked to a coding sequence are capable of effecting the transcription, and in some cases, the translation, of a coding sequence. The control sequences need not be contiguous with the coding sequence so long as they function to direct the expression of the coding sequence. Thus, for example, intervening untranslated yet transcribed sequences can be present between a promoter sequence and the coding sequence and the promoter sequence can still be considered "operably linked" to the coding sequence. In fact, such sequences need not reside on the same contiguous DNA molecule (i.e. chromosome) and may still have interactions resulting in altered regulation.

As used herein the term "selectable marker" refers to a gene introduced into a cell, which confers a trait suitable for artificial selection. General use selectable markers are well-known to those of ordinary skill in the art. Drug selectable markers such as ampicillin/carbenicillin, kanamycin, chloramphenicol, erythromycin, tetracycline, gentamicin, bleomycin, streptomycin, puromycin, hygromycin, blasticidin, and G418 may be employed. A selectable marker may also be an auxotrophy selectable marker, wherein the cell strain to be selected for carries a mutation that renders it unable to synthesize an essential nutrient. Such a strain will only grow if the lacking essential nutrient is supplied in the growth medium. Essential amino acid auxotrophic selection of, for example, yeast mutant strains, is common and well-known in the art. "Selective medium" as used herein refers to cell growth medium to which has been added a chemical compound or biological moiety that selects for or against selectable markers or a medium that is lacking essential nutrients and selects against auxotrophic strains.

As used herein, the term "vector" is any of a variety of nucleic acids that comprise a desired sequence or sequences to be delivered to and/or expressed in a cell. Vectors are typically composed of DNA, although RNA vectors are also available. Vectors include, but are not limited to, plasmids, fosmids, phagemids, virus genomes, BACs, YACs, PACs, synthetic chromosomes, among others.

As used herein, "affinity" is the strength of the binding interaction between a single biomolecule to its ligand or binding partner Affinity is usually measured and described using the equilibrium dissociation constant, $K_D$. The lower the $K_D$ value, the greater the affinity between the protein and its binding partner Affinity may be affected by hydrogen bonding, electrostatic interactions, hydrophobic and Van der Waals forces between the binding partners, or by the presence of other molecules, e.g., binding agonists or antagonists.

In some implementations, affinity may be described using arbitrary units, wherein a certain binding affinity within an assay, for example the binding affinity between two wild-type protein binding partners or the wild-type species of a first protein binding partner and the wild-type species of a second protein binding partner, is set to an arbitrary unit of 1.0 and binding affinities for other pairs of protein binding partners, for example the mutant species of a first protein binding partner and the mutant species of a second protein binding partner, are measured relative proportionally to that certain binding affinity.

As used herein, "site saturation mutagenesis" (SSM), refers to a mutagenesis technique used in protein engineering and molecular biology, wherein a codon or set of codons is substituted with all possible amino acids at the position in the polypeptide. Alternatively, SSM may describe changing an amino acid residue at a given position to one of a subset of possible amino acid substitutions at the position, for example, substitution to all possible amino acids except for cysteine. SSM may be performed for one codon, several codons, or for every position in the protein. The result is a library of mutant proteins representing the full complement of possible amino acids at one, several, or every amino acid position in a polypeptide.

As used herein, "user-directed mutagenesis" refers to any process wherein a user modifies the amino acid sequence of polypeptide by any technique well known to those of skill in the art. A polypeptide may be modified at one or more amino acid residues in a defined way, e.g. an alanine residue may be changed to an arginine residue, or a polypeptide sequence may be modified in a randomized way, i.e., by using degenerate primers and randomized PCR amplification. A polypeptide may be modified by user-directed mutagenesis at one amino acid residue or many amino acid residues. A polypeptide may be modified by user-directed mutagenesis to include insertion and/or deletions of one or more amino acid residues, or a polypeptide sequence may be truncated by user-direction mutagenesis. A polypeptide may be modified by user-directed mutagenesis to include insertions or substitutions with natural or unnatural amino acids.

As used herein, a "paratope" is a part of an antibody which specifically recognizes and binds to the antibody's corresponding antigen. A paratope may also be known as an antigen-binding site. A paratope may comprise as many as approximately 15 amino acid residues of the antibody polypeptides, of which approximately 5 amino acid residues typically contribute most of the binding energy to a paratope. The amino acids comprising a paratope may be a continuous sequence of amino acid residues within the polypeptide chain of the antibody protein structure or may be discontinuous amino acid residues that confer conformational specificity upon the three-dimensional structure of the antibody protein structure. As used herein, "paratope mapping" is the process of experimentally identifying and characterizing the composition of a paratope within an antibody protein structure. Paratope mapping may define the amino acid sequence of the paratope, the three-dimensional structure of the paratope, and may provide information on the mechanisms of action defining the interaction of an antibody and its antigen.

As used herein, an "epitope" is a part of an antigen which is specifically recognized and bound by an antibody. An epitope may comprise as many as approximately 15 amino acid residues of the antigen polypeptides, of which approximately 5 amino acid residues typically contribute most of the binding energy to an epitope. The amino acids comprising an epitope may be a continuous sequence of amino acid residues within the polypeptide chain of the antigen protein or may be discontinuous amino acid residues that confer conformational specificity upon the three-dimensional structure of the folded antigen protein.

As used herein, "epitope mapping" is the process of experimentally identifying and characterizing the composition of an epitope within an antigen protein. Epitope mapping may define the amino acid sequence of the epitope, the three-dimensional structure of the epitope, and may provide information on the mechanisms of action defining the interaction of an antigen and its antibody.

As used herein, a "receptor" is a chemical structure comprising a polypeptide sequence that in its native physiological context receives and transduces signals relating to biological systems. Receptors are a diverse class of proteins and may include transmembrane receptors, intracellular receptors, cytoplasmic receptors, nuclear receptors, and the like. Transmembrane receptors are located in the plasma membrane such that a portion of the receptor is located extracellularly to receive signals from outside the cell. Receptors receive and transduce signals through diverse mechanisms, including but not limited signals transduced by ligand-gated ion channels, G-protein-coupled receptors, kinase-linked receptors, or by migration of a receptor across the nuclear envelope. Receptors usually bind a specific ligand and a ligand may be an agonist, partial agonist, antagonist, inverse agonist, or allosteric modulator of its corresponding receptor.

As used herein, a "ligand" is a molecule that produces a signal by binding to a receptor. A ligand molecule may be a polypeptide, an inorganic molecule, or an organic molecule. In some cases, ligand binding to a receptor protein alters the conformation of the protein to produce and transduce a signal across or within a cell. Ligands may include substrates, inhibitors, activators, signaling lipids, neurotransmitters, among other molecules. In many cases, the binding of a ligand to its corresponding receptor is specific with a high binding affinity.

As used herein, a "wild-type protein binding partner" is one of two polypeptides that specifically interact with each other within a biological context. As used herein, a "wild-type protein binding interaction" is the interaction between two wild-type protein binding partners. A wild-type protein binding partner may include a full-length human protein; a full-length protein of any other animal species; a truncated protein of any animal species; a portion of a protein of any animal species; a plant protein, a fungal protein, a viral protein, a viral protein, a de novo protein, or a truncated species of a protein of any source. A wild-type protein binding partner may be a synthetic peptide, a glycosylated polypeptide, or a polypeptide with other synthetic or naturally occurring post-translational modifications. A wild-type protein binding partner may be an engineered polypeptide, for example, a portion of an antibody that has been engineered to produce a therapeutic effect. As used herein, a wild-type protein binding partner may include naturally occurring variation of an animal polypeptide sequence, including naturally occurring variants due to SNPs or indels in the encoding nucleotide sequence.

As used herein, a "mutant protein binding partner" is one of two modified polypeptides whose unmodified species specifically interact with each other in a biological context. One or both protein binding partners in a wild-type protein binding interaction may be modified to produce a mutant protein binding partner. A mutant protein binding partner may or may not interact with the wild-type species of its corresponding protein binding partner. A mutant protein binding partner may or may not interact when both protein binding partners of a wild-type protein binding interaction have been modified to produce a first mutant protein binding partner and a second mutant protein binding partner. A wild-type protein binding partner may be modified by user-directed mutagenesis or site-saturation mutagenesis to produce a mutant protein binding partner.

In some implementations, the method comprises a first protein binding partner and a library of second protein binding partners. The library of second protein binding partners comprises a plurality of user-designated or randomly added mutants of a protein and the wild-type protein. The plurality of user-designated or randomly added mutants of the protein may comprise variants of the protein with 1, 2, 3, 4, 5, 6, 7, 8, 9, 10, or more amino acid substitutions. The amino acid substitutions may be chosen to introduce changes in charge to the protein or changes in conformational structure to the protein and wild-type amino acids may be substituted with natural or non-natural amino acids. In some implementations, the amino acid substitutions may be generated by site saturation mutagenesis (SSM) to produce an SSM library of protein binding partners. In some implementations, the library of second protein binding partners may be generated by alanine scanning. In some implementations, the library of second protein binding partners may be generated by random mutagenesis, such as with error prone PCR, or another method to introduce variation into the amino acid sequence of the expressed protein. The first protein binding partner and the library of second protein binding partners are assayed for binding affinity, such that affinity is measured for interaction between the first protein binding partner and each of the plurality of user-designated mutants individually, in a parallelized high-throughput manner. Members of the library of second protein binding partners that are found to have a binding affinity with the first protein binding partner that is higher or lower than the binding affinity of the wild-type target protein and the first protein binding partner are identified and selected for further study.

In some implementations wherein a first protein binding partner and a library of second protein binding partners are assayed for binding affinity, the assay may be phage display, yeast surface display, or another parallelized high-throughput method.

In other implementations, the method comprises a library of first protein binding partners and a library of second protein binding partners. The library of first protein binding partners comprises a plurality of user-designated or randomly added mutants of a protein and the wild-type protein. The plurality of user-designated or randomly added mutants of the protein may comprise variants of the targeting protein with 1, 2, 3, 4, 5, 6, 7, 8, 9, 10, or more amino acid substitutions. The amino acid substitutions may be chosen to introduce changes in charge to the protein or changes in conformational structure to the protein and wild-type amino acids may be substituted with natural or non-natural amino acids. In some implementations, the amino acid substitutions may be generated by site saturation mutagenesis (SSM) to produce an SSM library of protein binding partners. In some implementations, the library of second protein binding partners may be generated by alanine scanning. The library of second protein binding partners comprises a plurality of user-designated or randomly added mutants of a protein and the wild-type protein. The plurality of user-designated or randomly added mutants of the protein may comprise variants of the target protein with 1, 2, 3, 4, 5, 6, 7, 8, 9, 10, or more amino acid substitutions. The amino acid substitutions may be chosen to introduce changes in charge to the protein or changes in conformational structure to the protein and wild-type amino acids may be substituted with natural or non-natural amino acids. In some implementations, the amino acid substitutions may be generated by site saturation mutagenesis (SSM) to produce an SSM library of protein binding partners. In some implementations, the library of second protein binding partners may be generated by alanine scanning. The library of first protein binding partners and the library of second protein binding partners are assayed for binding affinity, such that affinity is measured for interaction between each of the plurality of mutant first protein binding partners and each of the plurality of mutant second protein binding partners pair-wise individually in a parallelized high-throughput manner. Pairs comprising a member chosen from the library of first protein binding partners and a member chosen from the library of second protein binding partners that are found to have a binding affinity that is higher or lower than the binding affinity of the wild-type first protein binding partner and the wild-type second protein binding partner are identified and selected for further study.

In some implementations wherein a library of first protein binding partners is assayed against a library of second protein binding partners for binding affinity, the assay may be the yeast two-hybrid system, the AlphaSeq system, or another parallelized high-throughput library-by-library screening method. Binding affinities for the interaction between mutant protein binding partners relative to the binding affinity between wild-type protein binding partners may be measured by any number of methods for quantifying protein binding affinity, including yeast two-hybrid screening, biolayer interferometry, ELISA, quantitative ELISA, surface plasmon resonance, FACS-based enrichment methods, synthetic yeast agglutination, the AlphaSeq platform, or any other measurement of protein interaction strength. The AlphaSeq method is described in U.S. patent application Ser. No. 15/407,215 (US 2017-0205421 A1), hereby incorporated herein in its entirety for all purposes.

In some implementations, pairs of protein binding partners identified by the methods disclosed herein are further characterized by, e.g., crystallography, cryo-electron microscopy, micro-electron diffraction, mass spectrometry, computational modeling, among other methods for characterizing protein-protein complexes that are well known in the art. Pairs of protein binding partners or mutant protein binding partners may be further characterized individually or in the context of a protein-protein complex between the two partners.

In some implementations, the first binding partner and second protein binding partner are full-length proteins. In other implementations, the first binding partner and second protein binding partner are truncated proteins. In other implementations, the first binding partner and second protein binding partner are fusion proteins. In other implementations, the first binding partner and second protein binding partner are tagged proteins. Tagged proteins include proteins that are epitope tagged, e.g., FLAG-tagged, HA-tagged, His-tagged, Myc-tagged, among others known in the art. In some implementations, the first protein binding partner is a full-length protein and the second protein binding partner is a truncated protein. The first protein binding partner and second protein binding partner may each be any of the following: a full-length protein, truncated protein, fusion protein, tagged protein, or combinations thereof.

In some implementations, the first binding partner is an antibody or truncated portion of an antibody polypeptide. In other implementations the library of first binding partners is a library of antibodies, truncated antibody polypeptides, or a library of antibody mutants generated by site saturation mutagenesis, alanine scanning, or other methods well known in the art. Antibodies, also known as immunoglobulins, are relatively large multi-unit protein structures that specifically recognize and bind a unique molecule or molecules. For most antibodies, two heavy chain polypeptides of approximately 50 kDA and two light chain polypeptides of approximately 25 kDA are linked by disulfide bonds to form the larger Y-shaped multi-unit structure. Variable and hypervariable regions representing amino-acid sequence variability at the tips of the Y-shaped structure confer specificity for a given antibody to recognize its target.

In some implementations, the first binding partner is a single-chain variable fragment (scFv), a fusion protein of the variable regions of the heavy ($V_H$) and light chains ($V_L$) of an immunoglobulin connected by short linker peptides. In some implementations, the library of first protein binding partners is a library of scFvs or a library of scFvs mutants generated by site saturation mutagenesis, alanine scanning, or other methods well known in the art.

In some implementations, the first binding partner is an antigen-binding fragment (Fab), a region of an antibody that binds to an antigen. A Fab may comprise one constant and one variable domain of each of the heavy and the light chain, and includes the paratope region of the antibody. In some implementations, the library of first protein binding partners is a library of Fabs or a library of Fab mutants generated by site saturation mutagenesis, alanine scanning, or other methods well known in the art.

In some implementations, the first binding partner may be a portion of a single domain antibody, or VHH, the antigen-binding fragment of a heavy chain only antibody. A VHH comprises one variable domain of a heavy-chain antibody. In some implementations, the library of first protein binding partners is a library of VHHs or a library of VHH mutants generated by site saturation mutagenesis, alanine scanning, or other methods well known in the art.

In some implementations, the second binding partner is an antigen. In other implementations the library of second binding partners is a library of antigens or a library of antigens generated by site saturation mutagenesis, among other methods. An antigen is a molecule or molecular structure that is targeted by an antibody. Antigens are typically proteins, polypeptides, or polysaccharides that are targeted by a specific corresponding antibody. An antigen comprises an epitope, the portion of the antigen that is recognized by, and confers specificity to, the antigen's corresponding antibody.

In some implementations, for pairs of protein binding partners wherein the first protein binding partner is an antibody, scFv, Fab, or FHH and the second protein binding partner is an antigen, a wild-type antibody scFv, Fab, or FHH may be screened against a library of mutant antigens to determine the effect of antigen mutants on affinity between the antibody and the antigen. In other implementations, a wild-type antibody, scFv, Fab, or FHH may be screened against a library of mutant antigens for the purpose of epitope mapping, i.e., to define the amino acid sequence of the epitope, the three-dimensional structure of the epitope, and may provide information on the mechanisms of action defining the interaction between the epitope and the antibody.

In some implementations, for pairs of protein binding partners wherein the first protein binding partner is an antibody, scFv, Fab, or FHH and the second protein binding partner is an antigen, a library of mutant antibodies, scFvs, Fabs, or FHHs may be screened against a wild-type antigen to determine the effect of antibody, scFv, Fab, or FHH mutants on affinity between the antibody, scFv, Fab, or FHH and the antigen. In other implementations, a library of mutant antibodies, scFvs, Fabs, or FHHs may be screened against a wild-type antigen for the purpose of paratope mapping, i.e., to define the amino acid sequence of the paratope, the three-dimensional structure of the paratope, and may provide information on the mechanisms of action defining the interaction between the paratope and the antigen.

In some implementations, for pairs of protein binding partners wherein the first protein binding partner is an antibody, scFv, Fab, or FHH and the second protein binding partner is an antigen, a library of mutant antibodies, scFvs, Fabs, or FHHs may be screened against a library of mutant antigens to simultaneously interrogate the effects of antibody, scFv, Fab, or FHH mutants and antigen mutants on affinity between the antibody, scFv, Fab, or FHH and the antigen. In other implementations, a library of mutant antibodies, scFvs, Fabs, or FHHs may be screened against a library of mutant antigens for the purpose of epitope and paratope mapping, i.e., to define the amino acid sequences of the epitope and paratope, the three-dimensional structures of the epitope and paratope, and may provide information on the mechanisms of action defining the interaction between the antibody and the antigen.

As used herein, "substantially different than" refers to two quantitative binding affinity values that are from about 5%, 10%, 20%, 15%, 20%, 25%, 30%, 35%, 40%, 45%, 50%, 60%, 70%, 80%, 90%, 100%, 200%, 300%, to about 500% or more different from each other in magnitude. The quantitative binding affinity values may be measured in $K_D$ units or may be quantified by normalizing the binding affinity of a certain pair of protein binding partners to an arbitrary unit of 1.0 and measuring the binding affinity of a plurality of other protein binding partners in arbitrary units relative to that certain pair of protein binding partners that are normalized to an arbitrary unit of 1.0.

As used herein, "substantially the same as" refers to two quantitative binding affinity values that are within from about 20%, 15%, 10%, 9%, 8%, 7%, 6%, 5%, 4%, 3%, 2%, 1%, to about 0.1% in value. The quantitative binding affinity values may be measured in $K_D$ units or may be quantified by normalizing the binding affinity of a certain pair of protein binding partners to an arbitrary unit of 1.0 and measuring the binding affinity of a plurality of other protein binding partners in arbitrary units relative to that certain pair of protein binding partners that are normalized to an arbitrary unit of 1.0.

As used herein, "substantially higher than" refers to one quantitative binding affinity value that is from about 5%, 10%, 20%, 15%, 20%, 25%, 30%, 35%, 40%, 45%, 50%, 60%, 70%, 80%, 90%, 100%, 200%, 300%, to about 500% or more higher than another quantitative binding affinity value. The quantitative binding affinity values may be measured in $K_D$ units or may be quantified by normalizing the binding affinity of a certain pair of protein binding partners to an arbitrary unit of 1.0 and measuring the binding affinity of a plurality of other protein binding partners in arbitrary units relative to that certain pair of protein binding partners that are normalized to an arbitrary unit of 1.0.

As used herein, "substantially lower than" refers to one quantitative binding affinity value that is from about 95%, 90%, 85%, 80%, 75%, 70%, 65%, 60%, 55%, 50%, 45%, 40%, 35%, 30%, 25%, 20%, 15%, 10%, to about 5% or less of another quantitative binding affinity value. The quantitative binding affinity values may be measured in $K_D$ units or may be quantified by normalizing the binding affinity of a certain pair of protein binding partners to an arbitrary unit of 1.0 and measuring the binding affinity of a plurality of other protein binding partners in arbitrary units relative to that certain pair of protein binding partners that are normalized to an arbitrary unit of 1.0.

Figure 15:
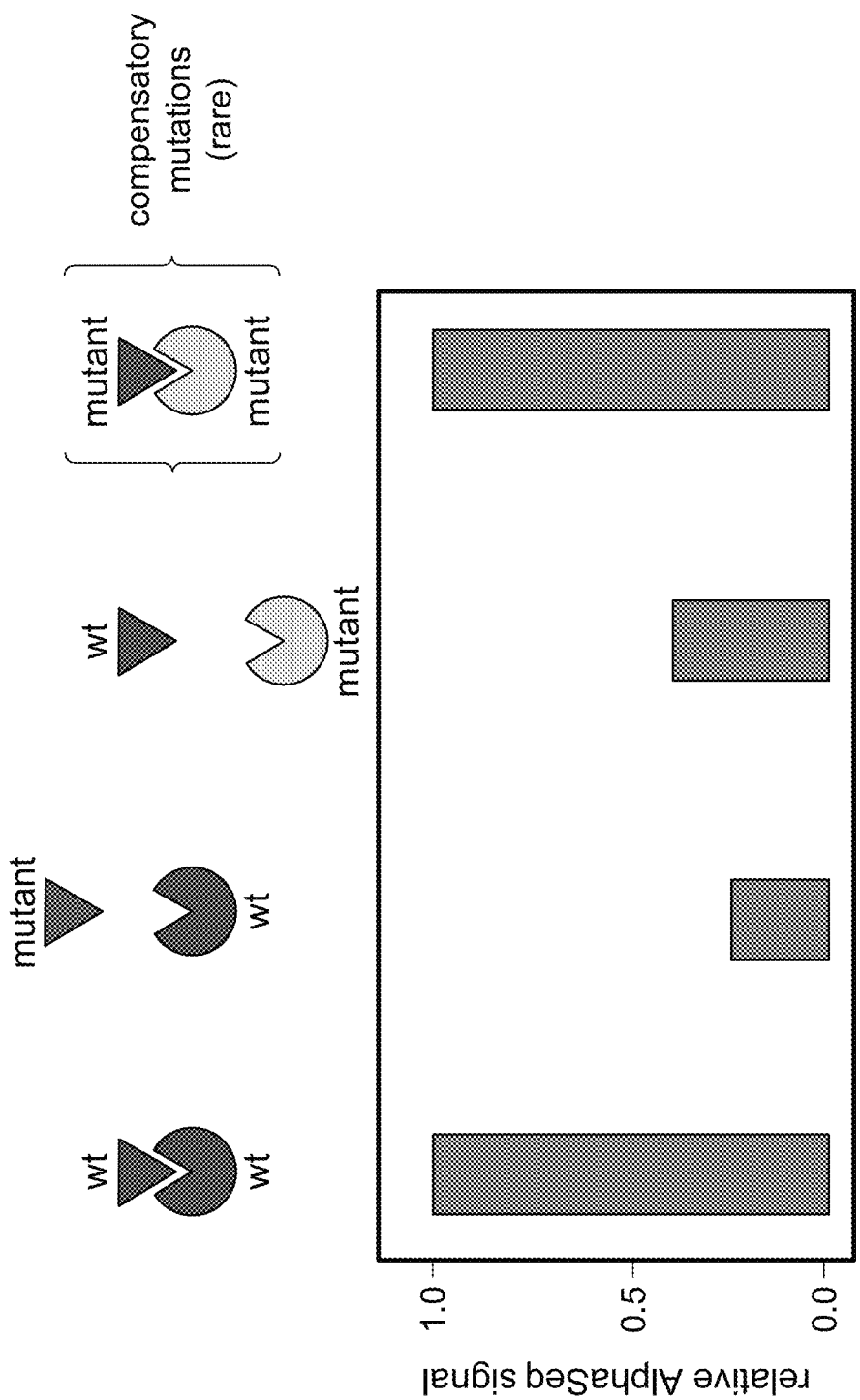

In some implementations, the methods disclosed herein may be used to identify compensatory mutations of the protein binding partners. As discussed above, a library of first protein binding partners may be screened against a library of second protein binding partners using the methods disclosed herein, such that affinity is measured for interactions between each of the plurality of first protein binding partners and each of second protein binding partners in a parallelized high-throughput manner. For a given interaction between two individual species of protein binding partners, there may occur instances wherein the following affinity relationships are detected simultaneously: (a) a mutant species of the first protein binding partner and the wild-type species of the second protein binding partner have a lower binding affinity as detected by the methods disclosed herein than that of between the wild-type species of the first protein binding partner and the wild-type species of the second protein binding partner; (b) the wild-type species of the first protein binding partner and a mutant species of the second protein binding partner have a lower binding affinity as detected by the methods disclosed herein than that of between the wild-type species of the first protein binding partner and the wild-type species of the second protein binding partner; and (c) the mutant species of the first protein binding partner described in (a) and the mutant species of the second protein binding partner described in (b) have a binding affinity as detected by the methods disclosed herein that is stronger, equivalent or about equivalent to that of between the wild-type species of the first protein binding partner and the wild-type species of the second protein binding partner. Two mutations of a pair of protein binding partners that exhibit the relationship described above may be referred to as compensatory mutations, wherein the mutation of the second protein binding partner compensates for the affinity-reducing impact of the mutation of the first protein binding partner when the two mutations co-occur, thereby restoring wild-type affinity levels between the two protein binding partners, as illustrated in FIG. 15. This scenario would indicate proximity between the two mutant residues and be useful for structural determination and/or protein engineering.

In another implementation, for a given interaction between two individual species of protein binding partners, there may occur instances wherein the following alternative affinity relationships are detected simultaneously: (a) a mutant species of the first protein binding partner and the wild-type species of the second protein binding partner have a lower binding affinity as detected by the methods disclosed herein than that of between the wild-type species of the first protein binding partner and the wild-type species of the second protein binding partner; (b) the wild-type species of the first protein binding partner and a mutant species of the second protein binding partner have a binding affinity as detected by the methods disclosed herein that is stronger, equivalent or about equivalent to that of between the wild-type species of the first protein binding partner and the wild-type species of the second protein binding partner; and (c) the mutant species of the first protein binding partner described in (a) and the mutant species of the second protein binding partner described in (b) have a binding affinity as detected by the methods disclosed herein that is stronger or significantly stronger than that of between the wild-type species of the first protein binding partner and the wild-type species of the second protein binding partner. Two mutations of a pair of protein binding partners that exhibit the relationship described above may also be referred to as compensatory mutations, wherein the mutation of the protein binding partners together confer additional binding affinity, more so than either of the two compensatory mutations occurring on its own. This scenario is shown between the K54I mutation of the antigen PD-1 and the Y101K mutation of the short-chain variable fragment (scFv) of the monoclonal antibody pembrolizumab (pembro) in FIG. 16. This scenario would indicate proximity between the two mutant residues and be useful for structural determination, protein engineering, or IP protection purposes.

In another implementation, for a given interaction between two individual species of protein binding partners, there may occur instances wherein the following alternative affinity relationships are detected simultaneously: (a) a mutant species of the first protein binding partner and the wild-type species of the second protein binding partner have a binding affinity that is stronger, equivalent or about equivalent to that of between the wild-type species of the first protein binding partner and the wild-type species of the second protein binding partner; (b) the wild-type species of the first protein binding partner and a mutant species of the second protein binding partner have a binding affinity that is lower than that of between the wild-type species of the first protein binding partner and the wild-type species of the second protein binding partner; and (c) the mutant species of the first protein binding partner described in (a) and the mutant species of the second protein binding partner described in (b) have a binding affinity as detected by the methods disclosed herein that is equivalent or about equivalent to that of between the wild-type species of the first protein binding partner and the wild-type species of the second protein binding partner. Two mutations of a pair of protein binding partners that exhibit the relationship described above may be referred to as compensatory mutations, wherein the mutation of the second protein binding partner compensates for the affinity-reducing impact of the mutation of the first protein binding partner when the two mutations co-occur, thereby restoring wild-type affinity levels between the two protein binding partners.

In another implementation, for a given interaction between two individual species of protein binding partners, there may occur instances wherein the following alternative affinity relationships are detected simultaneously: (a) a mutant species of the first protein binding partner and the wild-type species of the second protein binding partner have a binding affinity that is stronger, equivalent or about equivalent to that of between the wild-type species of the first protein binding partner and the wild-type species of the second protein binding partner; (b) the wild-type species of the first protein binding partner and a mutant species of the second protein binding partner have a binding affinity that is stronger, equivalent or about equivalent than that of between the wild-type species of the first protein binding partner and the wild-type species of the second protein binding partner; and (c) the mutant species of the first protein binding partner described in (a) and the mutant species of the second protein binding partner described in (b) have a binding affinity as detected by the methods disclosed herein that is lower than that of between wild-type species of the first protein binding partner and the wild-type species of the second protein binding partner. Two mutations of a pair of protein binding partners that exhibit the relationship described above may be useful for identifying amino acids that are in close proximity to each other at the protein-protein interface and particularly useful for mediating the binding affinity between the two protein binding partners.

In some implementations, an "expected binding affinity" or "expected interaction strength" may be defined and predicted for a pair of mutated protein binding partners. In some implementations, an expected binding affinity may be defined for a pairing of an antibody mutant species and an antigen mutant species. As used herein, the expected binding affinity is defined as the affinity that one would expect to observe between two mutant protein binding partners based on the observed impact of each mutant on binding to the corresponding wild-type protein binding partner. Expected binding affinity is calculated by (1) normalizing wild-type-by-wild-type binding affinity to 1.0, (2) calculating relative binding affinity for each of the mutant protein binding species interaction with its wild-type protein binding partner to yield a first mutant protein binding affinity and a second mutant protein binding affinity, (3) multiplying the first mutant protein binding affinity and the second mutant protein binding affinity to yield an expected binding affinity for the interaction of the two protein binding partners with each other.

For example, the observed binding affinity of the interaction of the wild-type species of a first protein binding partner and the wild-type species of a second protein binding partner is normalized to an arbitrary unit of 1.0; the observed binding affinity of the interaction of the wild-type species of the first protein binding partner and a mutant species of the second protein binding partner is 0.5 relative to the affinity of the wild-type protein binding interaction; the observed binding affinity of the interaction of the mutant species of the first protein binding partner and the wild-type species of the second protein binding partner is 0.5 relative to the wild-type protein binding interaction; the expected binding affinity of the interaction of the mutant species of the first protein binding partner and the mutant species of the second protein binding partner is calculated to be 0.25.

In some implementations, an "observed binding affinity" may be determined for each of many interactions between mutant protein binding partners according to the methods disclosed herein. In an implementation, the observed affinity value of the interaction between the wild-type species of the first protein binding partner and the wild-type species of the second protein binding partner is normalized to an arbitrary unit of 1.0. The observed binding affinity of other pairs of protein binding partners, e.g., the binding affinity between a mutant species of the first protein binding partner and a mutant species of the second protein binding partner, are measured and quantified proportionally relative to the 1.0 value assigned to the interaction between the wild-type species of the first protein binding partner and the wild-type species of the second protein binding partner. Observed binding affinity for a pair of mutant protein binding partners may be compared to expected binding affinity to determine the ratio of observed binding affinity to expected binding affinity. In some implementations and for some pairs of protein binding partners, the ratio of observed binding affinity to expected binding affinity may be from about 1:1, 2:1, 3:1, 4:1, 5:1, 6:1, 7:1, 8:1, 9:1, to about 10:1, or greater than 10:1. In some implementations and for some pairs of protein binding partners, the ratio of observed binding affinity to expected binding affinity may be from about 1:1, 1:2, 1:3, 1:4, 1:5, 1:6, 1:7, 1:8, 1:9, to 1:10, or less than about 1:10.

For pairs of protein binding partners wherein the first protein binding partner is an antibody and the second protein binding partner is an antigen, and wherein compensatory mutations of the antibody and antigen have been identified by the methods disclosed herein, the amino acid residues involved in these pairs of compensatory mutations are spatially close at the antigen/antibody interface, yielding unique information about the protein-protein interface that is not available when using one-sided protein binding-based methods. Examples of compensatory mutations between protein binding partners as detected by the methods disclosed herein are indicators of structural proximity. In the absence of other structural data, pairs of compensatory mutations may be useful as distance constraints in building computational models of protein-protein interactions. Identifying compensatory mutations for pairs of protein binding partners yields unique information about proximity of interacting residues at the protein-protein interface. These distance constraints may also be useful for protein engineering and structural determination, or for informing intellectual property protection efforts for novel antibodies or antigens in the pharmaceutical and biotechnology industries.

In some implementations, the methods disclosed herein may be used to identify compensatory mutations between protein binding partners wherein the first protein binding partner is a receptor and the second protein binding partner is a ligand. The amino acid residues involved in these pairs of compensatory mutations are spatially close at the receptor/ligand interface, yielding unique information about the protein-protein interface that is not available when using one-sided protein binding-based methods. Examples of compensatory mutations between protein binding partners as detected by the methods disclosed herein are indicators of structural proximity. In the absence of other structural data, pairs of compensatory mutations may be useful as distance constrains in building computational models of protein-protein interactions. Identifying compensatory mutations for pairs of protein binding partners yields unique information about proximity of interacting residues at the protein-protein interface. These distance constraints may also be useful for protein engineering, structural determination, or for informing rational design efforts for novel receptors and ligands in the pharmaceutical and biotechnology industries. Compensatory mutations identified for receptor-ligand protein binding partners may be used to custom engineer specific behaviors between the receptor-ligand interaction that are useful for biomedical applications, for example, cell therapies, cancer treatments, immunological therapies. In some implementations, compensatory mutations may be identified between receptor-ligand protein binding partners wherein the receptor-ligand protein binding partners comprising compensatory mutations exhibit higher affinity than that of between wild-type species of the protein binding partners.

The methods disclosed herein are uniquely advantageous for identifying such synergistic interactions, i.e., for identifying mutations that enhance binding affinity between two protein binding partners, e.g., between a receptor and its ligand. Identifying such synergistic compensatory mutations between protein binding partners using previously available methods, e.g., conventional one-sided screening methods, was very difficult or impossible.

Further, the methods disclosed herein may be useful for identifying and engineering orthogonal protein interactions, for example, between a cell-surface receptor and its ligand, wherein the interaction between the engineered receptor, engineered ligand, and endogenous wild-type ligand (e.g., soluble growth factor or cytokine) is uniquely tunable for desired outcomes in a therapeutic context. For example, the protein interactions illustrated by FIG. 3B represent a one-side orthogonal binding relationship wherein the wild-type receptor binds and is activated by the wild-type ligand but not the mutant ligand, while the mutant ligand binds and is activated by both the wild-type ligand and the mutant ligand. The methods disclosed herein allow the identification of mutations of both the receptor and ligand that will confer such properties to the receptor-ligand interaction, possibly by the introduction of only a small number of highly impactful mutations to the receptor and the ligand.

The one-side orthogonal binding relationship illustrated by FIG. 3B may be particularly useful in the context of cell therapies, for example CAR-T cell therapy, where regulating the number and abundance of CAR-T cells within the patient may be important to the efficacy of the therapy. Using the methods disclosed herein, compensatory mutations to receptors may be identified allowing for the engineering of the CAR-T cells to express the customized cell-surface receptor bearing compensatory mutations identified by the methods disclosed herein. Likewise, a soluble growth factor or cytokine may be engineered to express compensatory mutations identified by the methods disclosed herein, such that the CAR-T cell surface receptor and soluble growth factor or cytokine exhibit a one-sided orthogonal affinity relationship like that depicted in FIG. 3B. By introducing possibly only a small number of highly impactful compensatory mutations to each of the cell-surface receptor and the soluble growth factor or cytokine, the CAR-T cell surface receptor may bind and be activated by both the engineered growth factor or cytokine and the wild-type growth factors or cytokines native to the patient's physiological milieu. Conversely, the engineered soluble growth factor or cytokine bearing compensatory mutations identified by the methods disclosed herein will bind and activate only the engineered CAR-T cell surface receptor and not affect the plurality or wild-type cell-surface receptors native to the patient's physiology. This pattern of customized orthogonal protein-protein interactions utilizing the methods disclosed herein will be useful for engineering cell therapies, immunotherapies, and biologics to treat a multitude of diseases and disorders.

FIG. 1 is a series of charts showing the library-by-library screening capacity of the AlphaSeq method. In each chart, a subset of protein interactions with affinities measured by biolayer interferometry spanning a wide affinity range are compared to AlphaSeq intensity to show the sensitivity and quantitative accuracy of the AlphaSeq method at a given network size. Chart 100 illustrates screening the interaction of a first library of 100 binding partners against a second library of 100 binding partners and measuring 10,000 interactions. Chart 102 illustrates screening the interaction of a first library of 1,000 binding partners against a second library of 1,000 binding partners and measuring 1,000,000 interactions. Chart 104 illustrates screening the interaction of a first library of 10,000 binding partners against a second library of 10,000 binding partners and measuring 100,000,000 interactions. Chart 106 demonstrates the correlation between protein-protein affinity ($K_D$) with AlphaSeq intensity for 10,000 interactions. Chart 108 demonstrates the correlation between protein-protein affinity ($K_D$) with AlphaSeq intensity for 1,000,000 interactions. Chart 110 demonstrates the correlation between protein-protein affinity (4) with AlphaSeq intensity for 100,000,000 interactions.

Figure 2A:
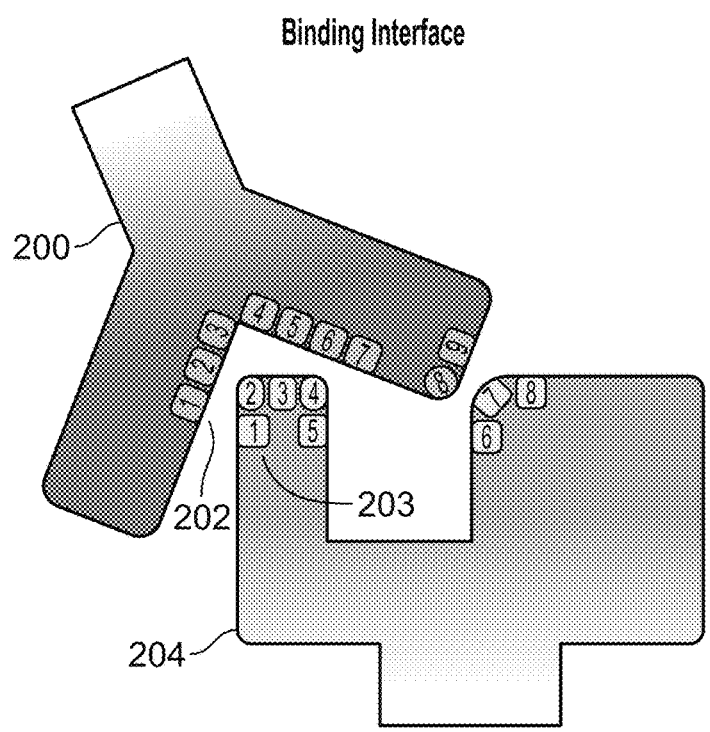
FIG. 2A is a schematic of two protein binding partners interacting in complex, wherein the first protein binding partner may be an antibody and the second protein binding partner may be an antigen. Residues on both protein binding partners at the protein-protein interface have been numbered.

FIG. 2A is a schematic of two protein binding partners interacting in complex, wherein the first protein binding partner 200 is an antibody and the second protein binding partner 204 is an antigen, emphasizing the interface between the two protein binding partners and a site saturation mutagenesis (SSM) screen of the two protein binding partners 200 and 204. Amino acid residue 202 of protein binding partner 200 corresponds to amino acid residue 203 of protein binding partner 204. Amino acid residue 202 of protein binding partner 200 may be substituted by one of any of the additional amino acid residues available, naturally occurring or artificial, and screened for interaction against a similar library of substitutions of amino acid residue 203 of protein binding partner 204.

Figure 2B:
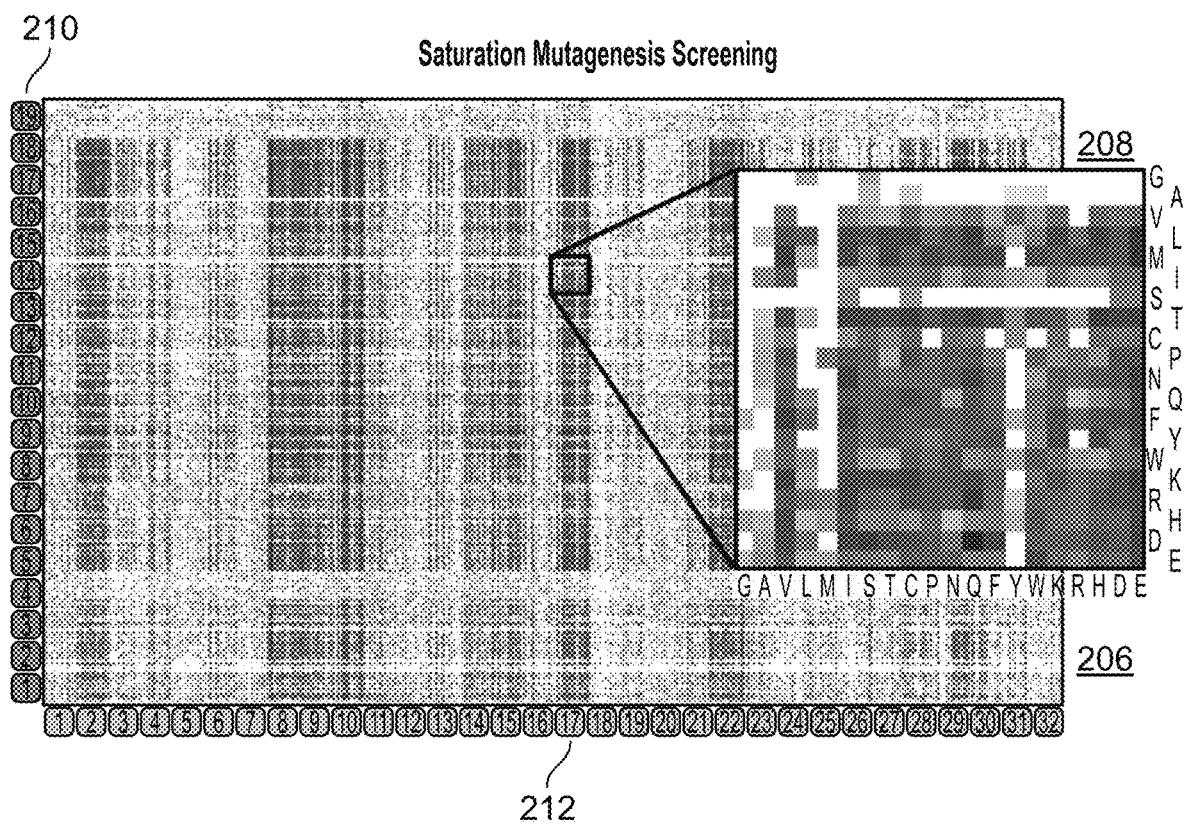
FIG. 2B illustrates the library-by-library intensity measurements by AlphaSeq of the interactions between protein binding partners. At 19 positions for one protein binding partner and 32 positions at the other protein binding partner, site saturation mutagenesis was performed. An inlay shows the measured interactions between all single amino acid mutations at two positions.

The results of such a library-by-library SSM screen are shown in FIG. 2B. Heatmap 206 illustrates the library-by-library intensity measurements by AlphaSeq of the interactions between protein binding partners carrying SSM mutations at every amino acid residue defining the protein-protein interface. Darker shades represent higher AlphaSeq intensity and lighter shades represent lower AlphaSeq intensity. For example, inset 208 highlights the library-by-library AlphaSeq intensities for an SSM library of substitutions of amino acid 210 measured against an SSM library of substitutions of amino acid 212. For the library-by-library screen whose data is represented by heatmap 206, amino acid residue 210 has been mutated to every one of the available naturally occurring amino acid residues (G, A, V, L, M, I, S, T C, P, N, Q, F, Y, W, K, R, H, D, E). Corresponding to amino acid residue 210, amino acid residue 212 has similarly been mutated to every one the available naturally occurring amino acid residues (G, A, V, L, M, I, S, T C, P, N, Q, F, Y, W, K, R, H, D, E). The intensity data for pair-wise interactions of variants of amino acid residue 210 and amino acid residue 212 are represented by heatmap inset 208. A color version of the heat map(s) included in, e.g., FIG. 2B is available via the United State Patent and Trademark Office (USPTO) Patent Application Information Retrieval system (PAIR, accessible via the following link: https://portal.uspto.gov/pair/PublcPair, U.S. Application No. 63/033,176, Supplemental Content tab).

FIGS. 3A-3C are graphical representations of a subset of protein-protein interactions detected by the data presented in FIGS. 2A-2B and illustrate the capability of the methods disclosed herein to detect relative affinity between wild-type and mutant protein binding partners and the effect of single amino acid substitutions on affinity between two protein binding partners. FIG. 3A illustrates a scenario wherein wild-type protein binding partners interact with high affinity, mutant protein binding partners interact with high affinity, but a mutant of either the first or second protein binding partner does not interact with the wild-type form of the other protein binding partner. The result is a pair of mutants, each with a single amino acid change from wild-type, that bind orthogonally to wild-type. FIG. 3B illustrates a scenario wherein both the wild-type and mutant form of the first protein binding partner interact with the wild-type form of the second protein binding partner, but the wild-type first protein binding partner does not interact with the mutant second protein binding partner, i.e., mutation of the second protein binding partner abolishes interaction with the wild-type first protein binding partner. FIG. 3C illustrates a scenario wherein both the wild-type and mutant form of the first protein binding partner interact with the mutant form of the second protein binding partner, but the mutant first protein binding partner does not interact with the wild-type second protein binding partner, i.e., mutation of the first protein binding partner abolishes interaction with the wild-type second protein binding partner.

Figure 4:
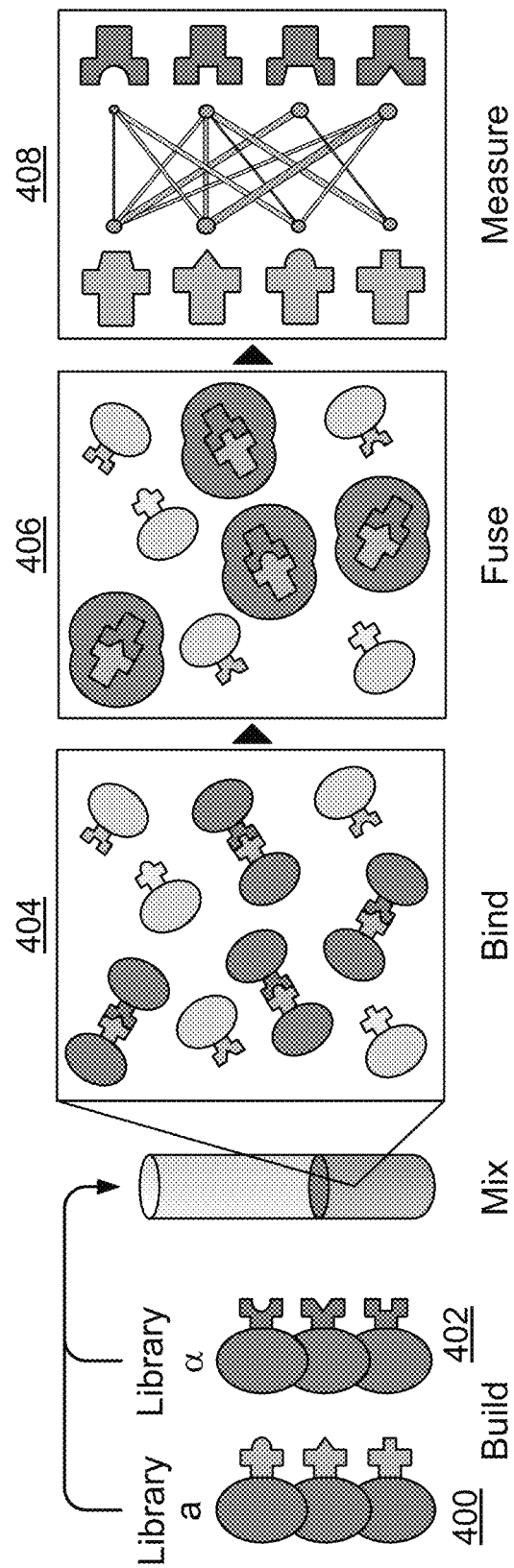
FIG. 4 illustrates the workflow of a library-by-library protein-protein interaction screen using the AlphaSeq platform.

FIG. 4 illustrates the workflow of a library-by-library protein-protein interaction screen using AlphaSeq. A first library 400 of protein binding partners and second library 402 of protein binding partners are generated by site-saturation mutagenesis and expressed in yeast. The two library populations are mixed and protein binding partners bind in interaction step 404. Cells expressing protein binding partners that have interacted mate in fusing step 406. Protein-protein interactions between the first and second libraries are detected and quantified in measuring step 408.

Figure 5:
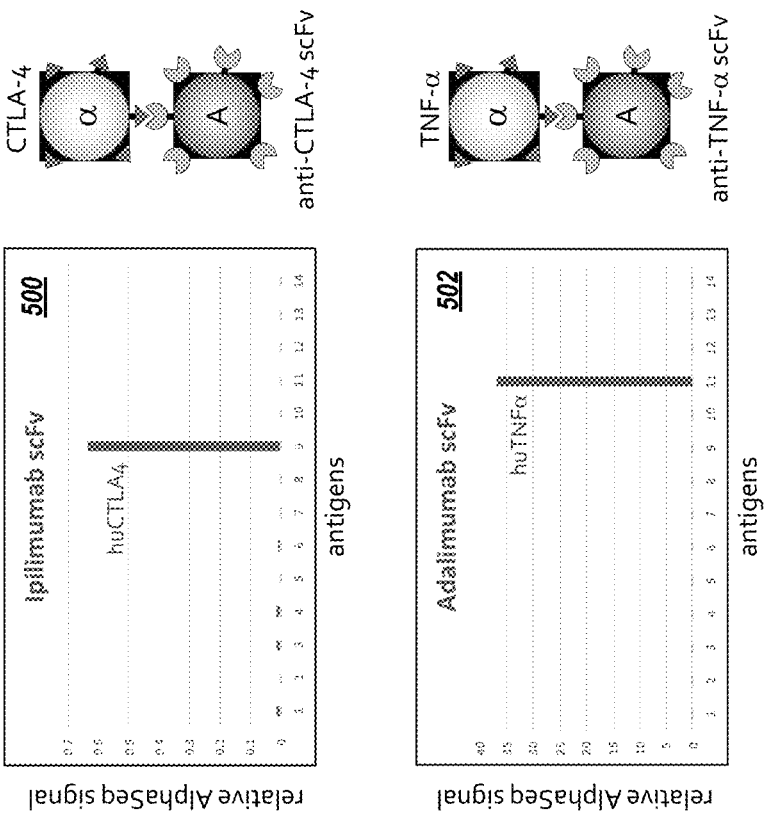
FIG. 5 is a plot of AlphaSeq protein interaction data representing antibody-antigen interactions measured with the AlphaSeq platform.

FIG. 5 illustrates that antibody-antigen interactions can be measured with the AlphaSeq platform. Well-characterized antibody-antigen pairs that are well known in the art were subjected to the AlphaSeq workflow. The system correctly identified pairs of cells having cognate binding partners and did not detect cross-reaction among non-cognate pairs. Plot 500 shows the detected interaction of huCTLA-4 and ipilimumab scFv and relative AlphaSeq signal. Plot 502 shows the detected interaction of huTNFα and adalimumab scFv.

Figure 6:
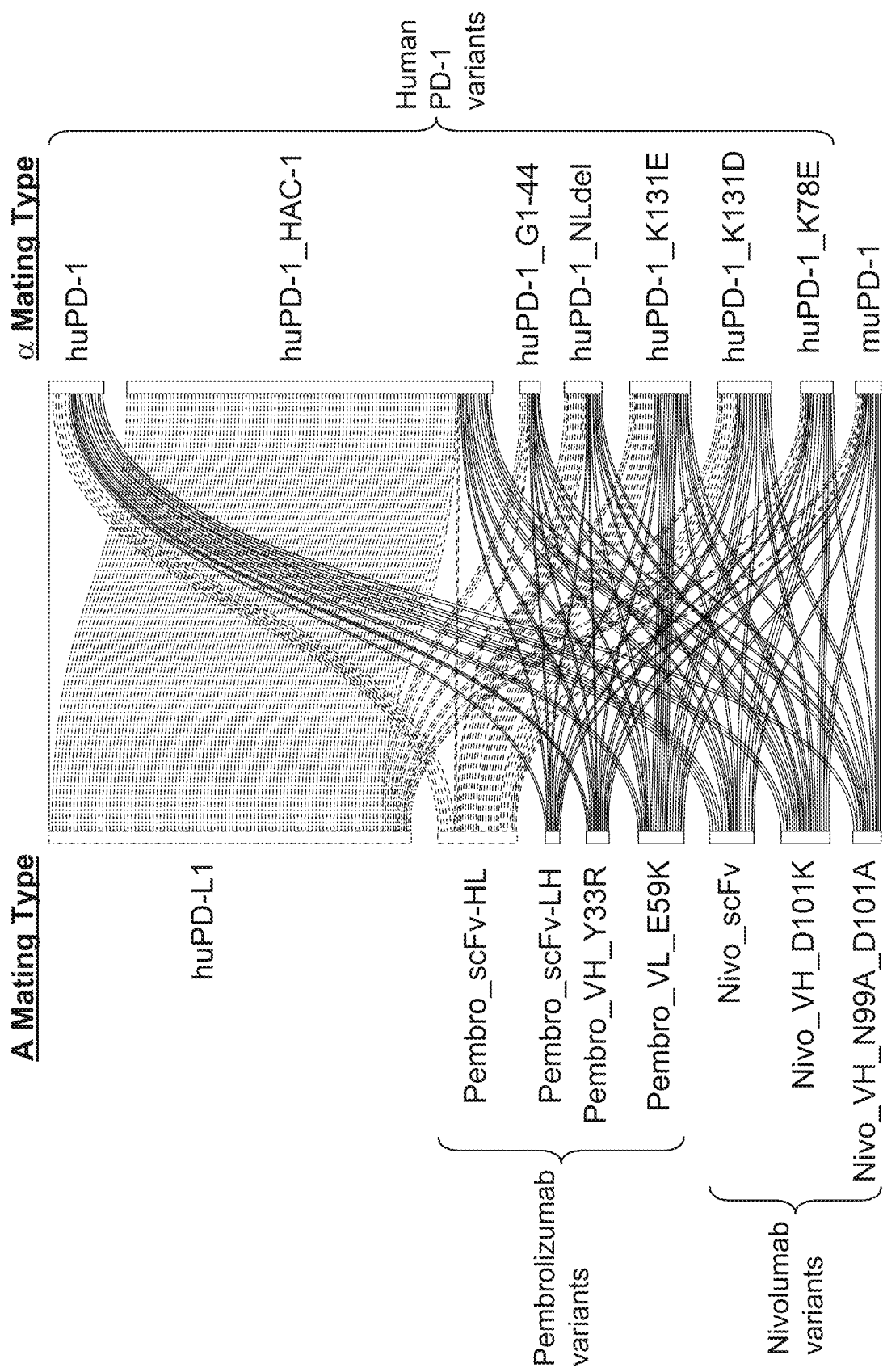
FIG. 6 illustrates results of an AlphaSeq experiment screening eight antigen variants against eight antibody variants, yielding detection and quantification of 64 interactions.

FIG. 6 illustrates results of an AlphaSeq experiment screening eight antigen variants against eight antibody variants, yielding detection and quantification of 64 interactions. The thickness of the connecting line indicates the magnitude of the mating frequency signal. The significant line 600 represents the interaction between the human programmed cell death ligand-1 (huPD-L1) and an engineered programmed cell death protein-1 (PD-1) ectodomain which had been previously reported and characterized by Maute et al. (Maute R L, Gordon S R, Mayer A T, McCracken M N, Natarajan A, Ring N G, Kimura R, Tsai J M, Manglik A, Kruse A C, Gambhir S S, Weissman I L, Ring A M. Engineering high-affinity PD-1 variants for optimized immunotherapy and immuno-PET imaging. Proc Natl Acad Sci USA. 2015 Nov. 24; 112(47):E6506-14. doi: 10.1073/pnas.1519623112. Epub 2015 Nov. 10. PMID: 26604307; PMCID: PMC4664306.), the entirety of which is incorporated by reference for all purposes. The significance of this interaction as detected by the AlphaSeq platform confirms that the methods disclosed herein are able to detect interactions between protein binding partners wherein the interactions are strengthened relative to the wild-type interaction by modification of one or both of the protein binding partners.

Figure 7:
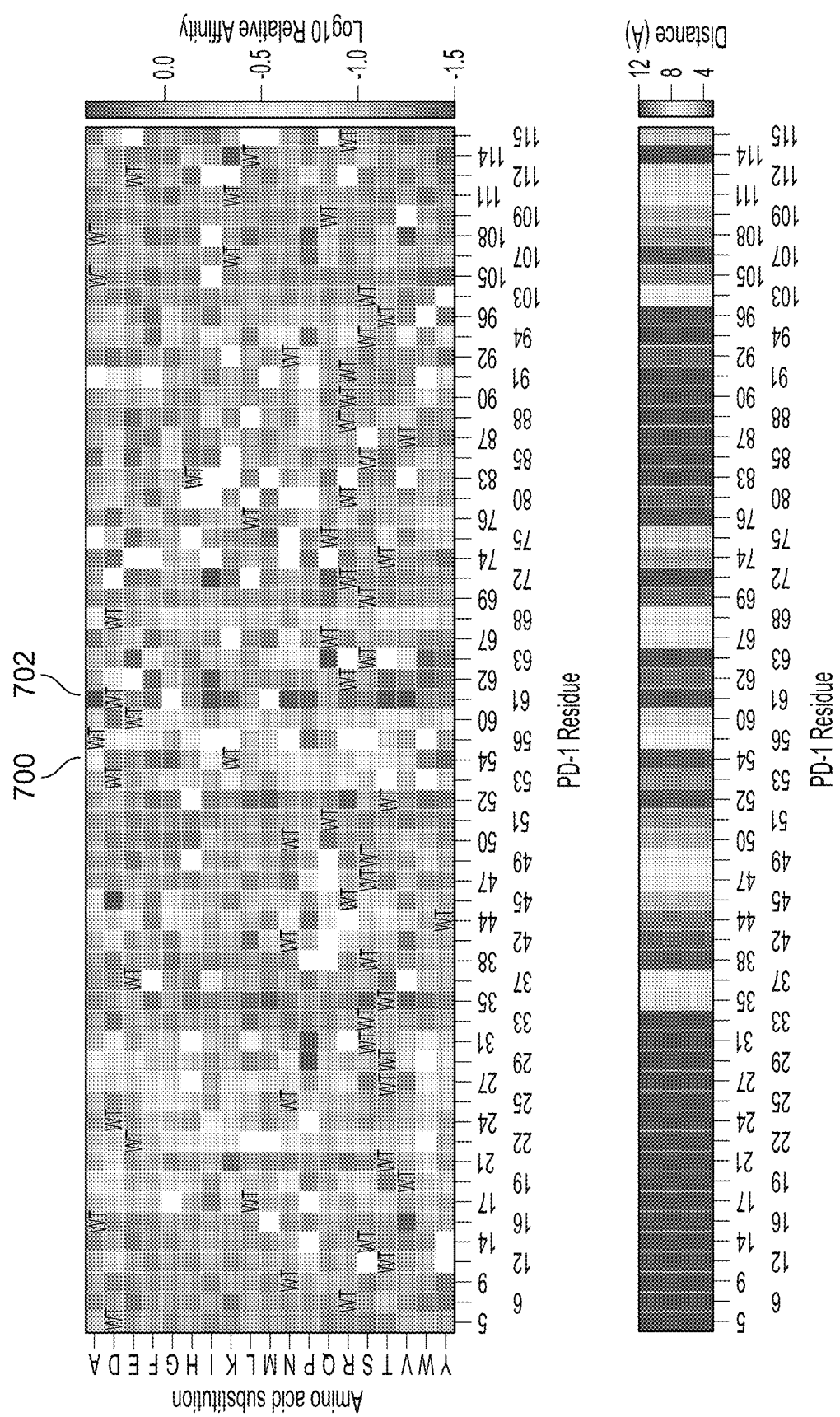
FIG. 7 is a heatmap representing results of a screen of a PD-1 site-saturation mutagenesis library against wild-type pembro scFv (antibody). The residue distance between the given PD-1 residue and the nearest pembro residue is also shown.

FIG. 7 is a heatmap representing results of a screen of 60 PD-1 variants (antigen variants) against wild-type pembro scFv (antibody). 60 PD-1 surface residues were chosen for mutagenesis and the resulting SSM library was subjected to the AlphaSeq workflow. AlphaSeq signals are displayed in a heatmap format, with the darkly shaded squares of varied patterns indicating high and low mating frequencies. The bar at the bottom of the figure represents the shortest distance between the residue to any atom within the antibody. Residues 700 and 702, corresponding to PD-1 residues 54 and 61, are particularly intolerant to substitution and are spatially close to the antibody based on the known x-ray structure. A color version of the heat map(s) included in, e.g., FIG. 7 is available via USPTO PAIR (access 63/033, 176, Supplemental Content tab).

Figure 8:
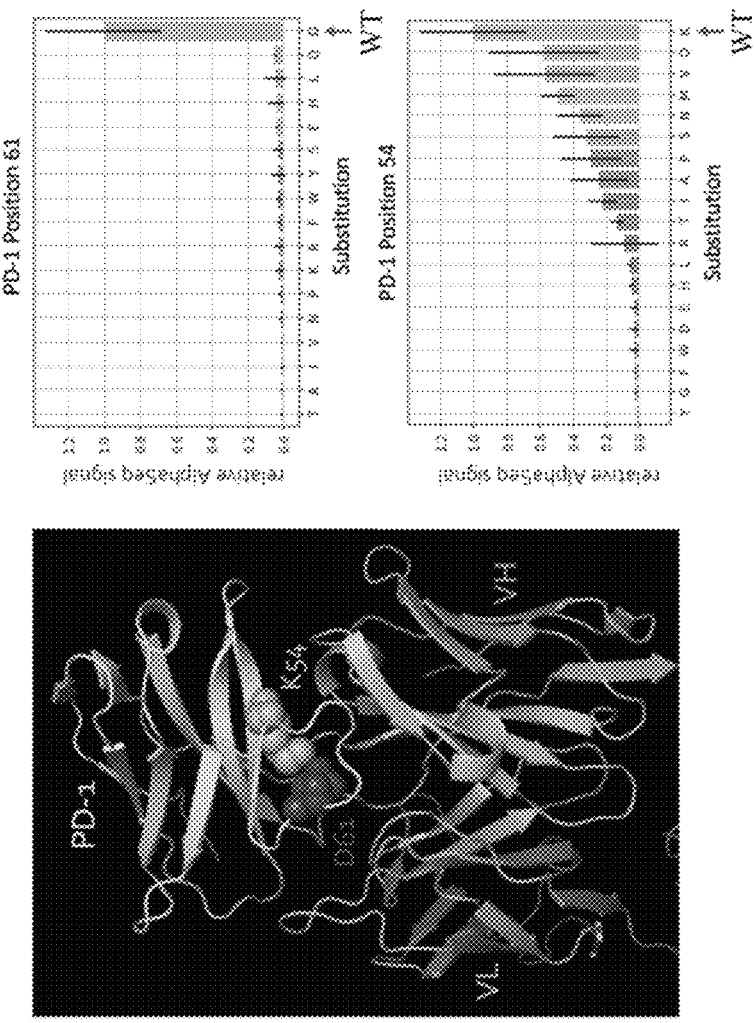
FIG. 8 is an illustration highlighting certain residues within the crystal structure of the PD-1/pembrolizumab interface.

FIG. 8 is an illustration highlighting certain residues within the crystal structure of the PD-1/pembrolizumab interface, which were identified by the data presented in FIG. 7. PD-1 residues K54 and D61 are particularly intolerant to substitution and are spatially close within the antibody-antigen interface.

Figure 9:
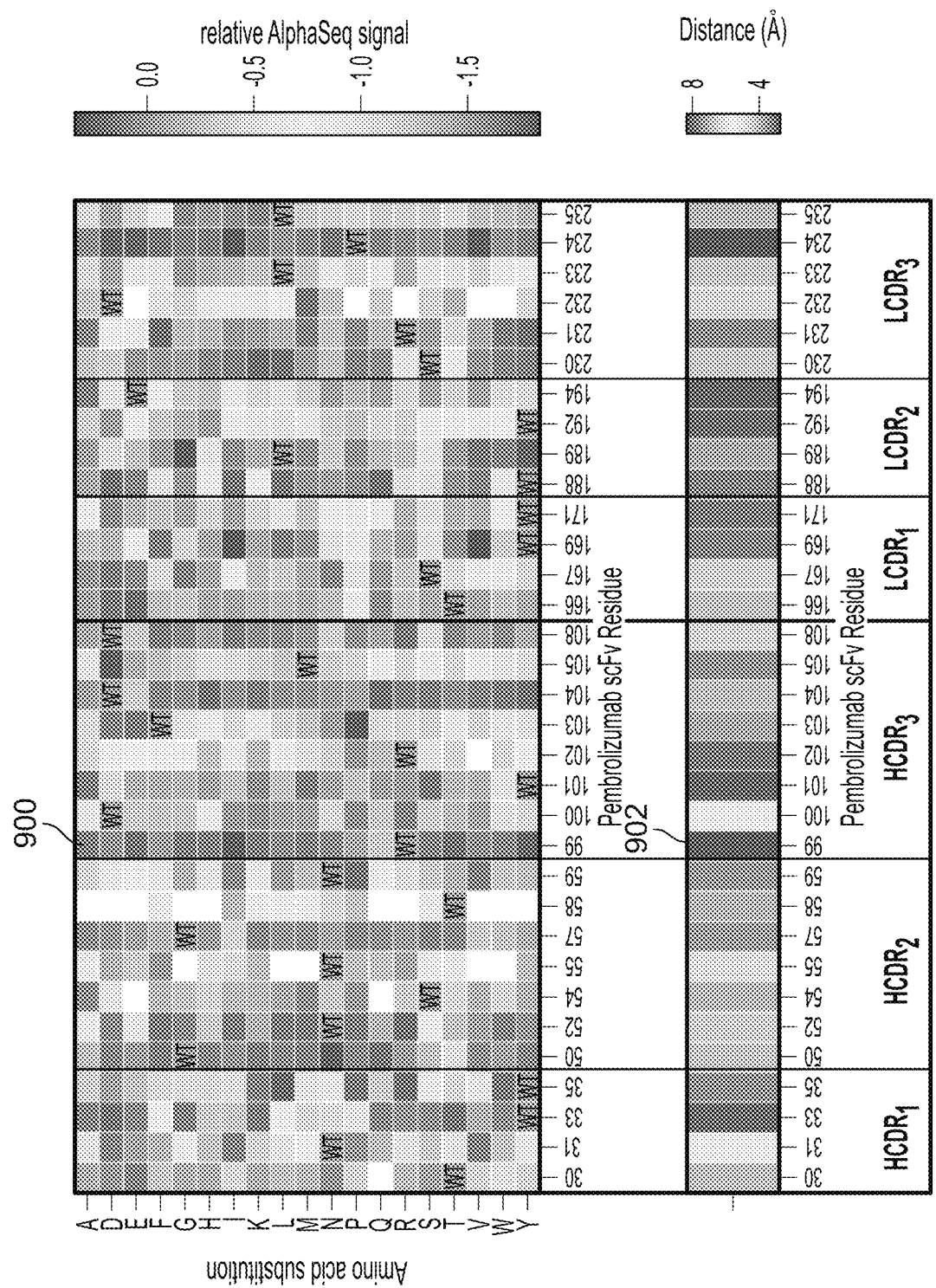
FIG. 9 is a heatmap representing results of a screen of a pembro sc

FIG. 9 is a heatmap representing results of a screen of 33 pembro scFv variants (antibody variants) against wild-type PD-1 (antigen). 33 positions within pembrolizumab scFv were mutagenized using SSM and the resulting library was subjected to the AlphaSeq workflow against wild-type PD-1. AlphaSeq signals are displayed in a heatmap format, with the darkly shaded squares of varied patterns representing high and low mating frequencies. The bar at the bottom of the figure represents the shortest distance between the residue to any atom within the antibody. Pembrolizumab scFv residue 99 is particularly intolerant to substitution and is spatially close within the antibody-antigen interface, as indicated by shaded column 900 and shaded box 902. A color version of the heat map(s) included in, e.g., FIG. 9 is available via USPTO PAIR (access 63/033,176, Supplemental Content tab).

Figure 10:
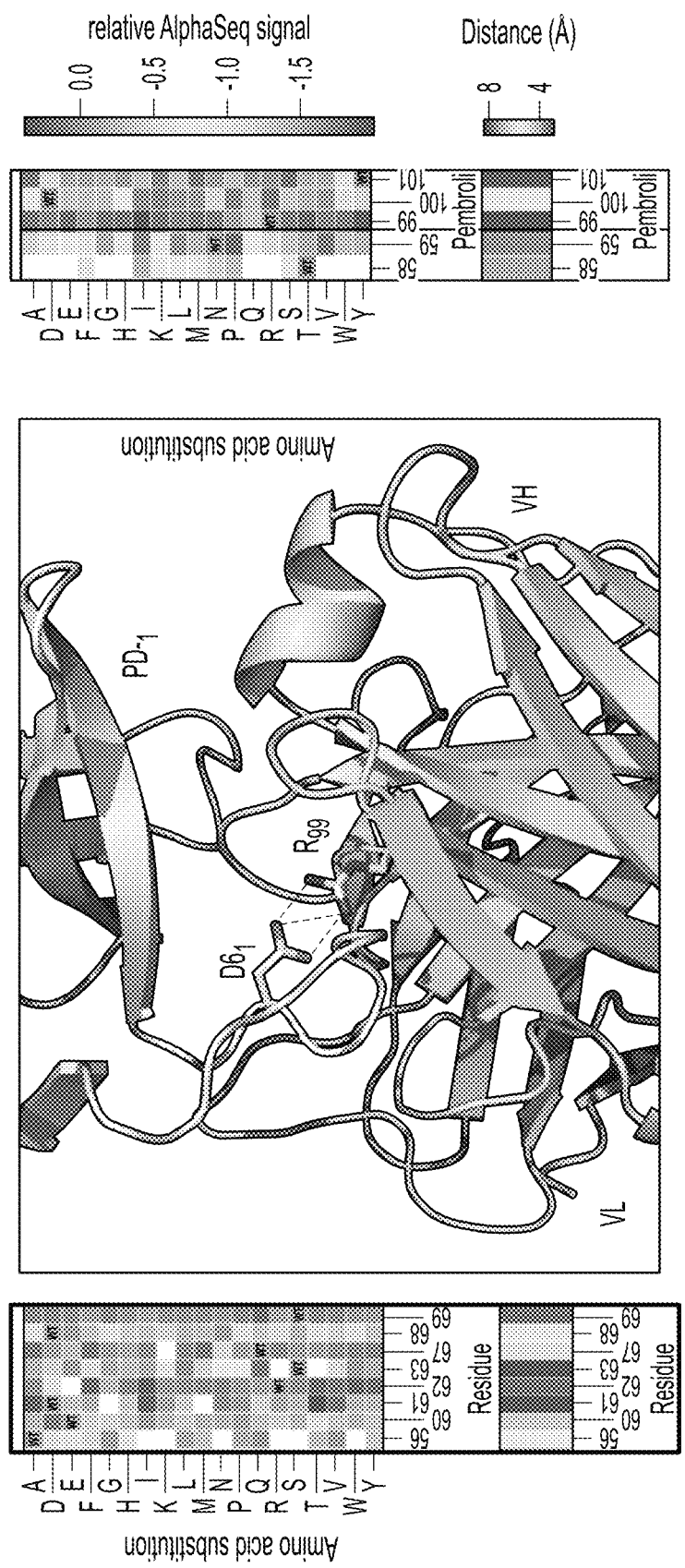

FIG. 10 is a graphical representation of the crystal structure of the PD-1/pembrolizumab scFv interface, highlighting certain residues at the antibody-antigen interface. PD-1 D61 and pembro scFv R99 are shown to be functionally important to the formation of a productive antigen-antibody complex, in certain embodiments, and substitutions at either site greatly diminish mating frequencies in the AlphaSeq assay. A color version of the heat map(s) included in, e.g., FIG. 10 is available via USPTO PAIR (access 63/033,176, Supplemental Content tab).

Figure 11:
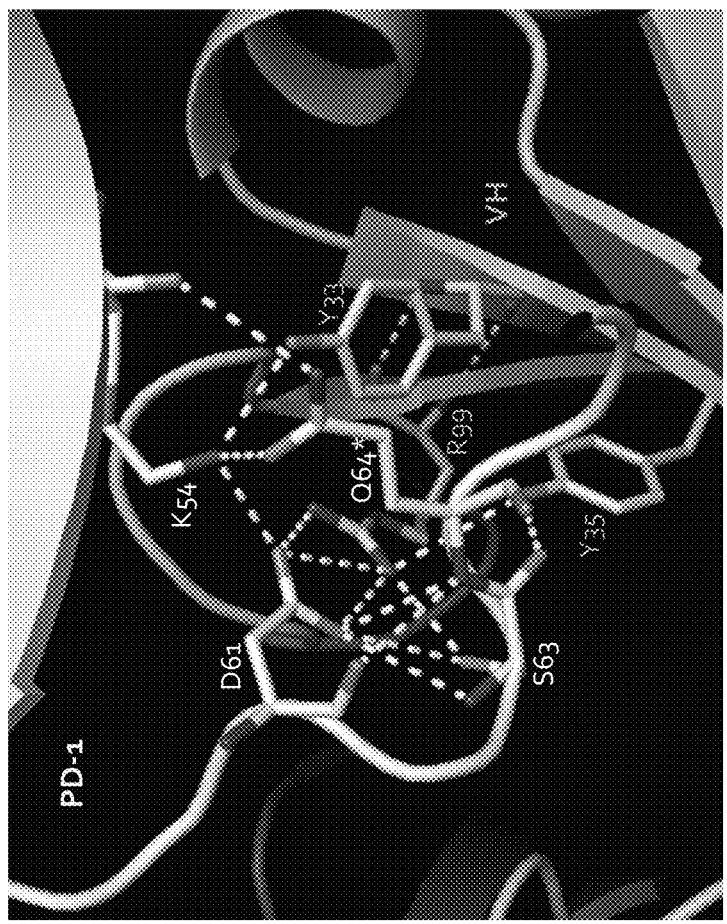

FIG. 11 is an illustration of the structure of the PD-1/pembrolizumab interface, highlighting a dense interaction network around the previously highlighted D61-R99 pair of residues. Mutationally-intolerant residues of PD-1 and pembrolizumab scFv are shown.

Figure 12A:
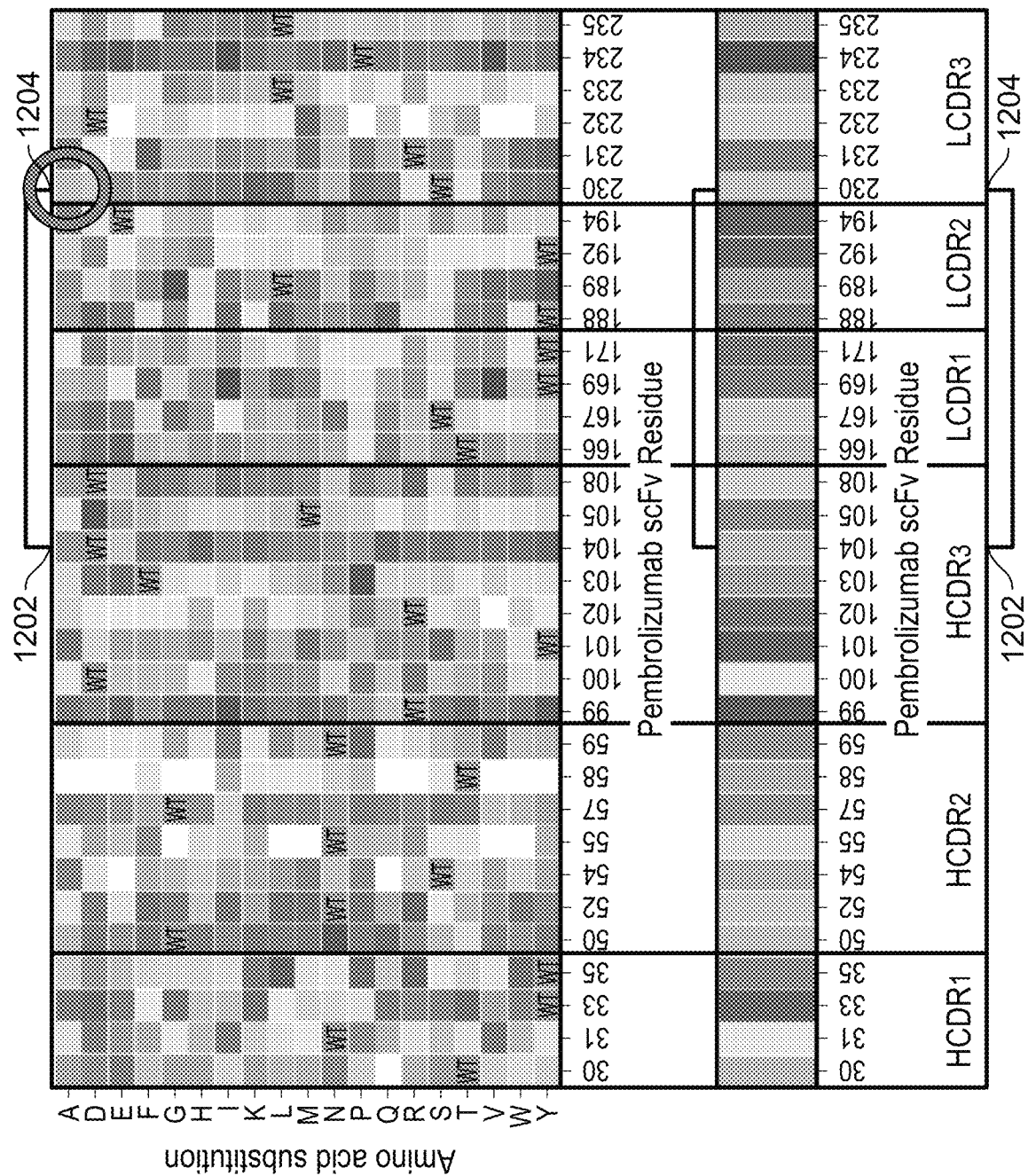
Figure 12B:
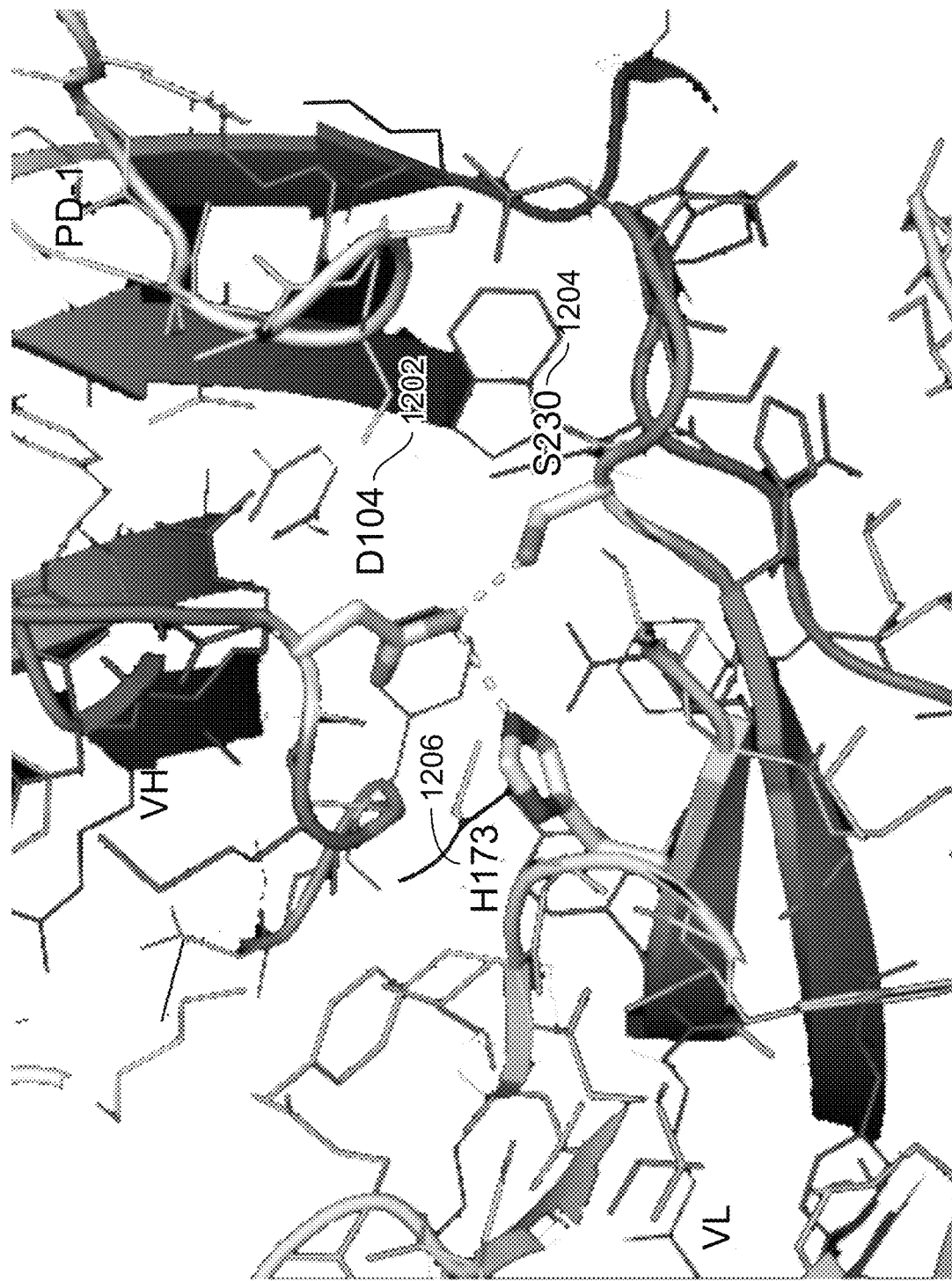

FIGS. 12A-12B are representations of the same dataset that is presented in FIG. 9. Pembrolizumab scFv residues D104 and S230 are highlighted as particularly intolerant to amino acid substitution. These residues are interacting with each other across the VH-VL interface, forming an interaction that stabilizes the relative positioning of the VH and VL domains within the antibody structure. Disruption of this specific interaction by mutation causes loss of binding, as read out by a lowering of the mating frequency scores generated by AlphaSeq. It is notable that substitution of alanine at pembrolizumab scFv residue 230 is tolerated, while most other substitutions are not. Alanine scanning alone would not have identified this site as being mutationally sensitive, highlighting the advantage of utilizing the full mutational spectrum generated by site-saturation mutagenesis and the AlphaSeq platform. A color version of the heat map(s) included in, e.g., FIG. 12A is available via USPTO PAIR (access 63/033,176, Supplemental Content tab).

FIG. 13 is a table of pairs of compensatory mutations identified by AlphaSeq relative intensity data based on yeast mating efficiencies measured in a library-by-library screen between pembro scFv (antibody) and PD-1 (antigen). Column 1300 describes PD-1 mutant protein binding partners, column 1302 describes the paired pembro scFv mutant protein binding partners, and column 1304 describes the minimum distance in angstroms between the paired mutant residues of columns 1300 and 1302. Pairs of residues harboring compensatory mutations are spatially close within the antibody-antigen interface. Rows highlighted in gray point to pairs of mutant protein binding partners for which relative intensity is plotted in FIGS. 16-17, described below.

Figure 14:
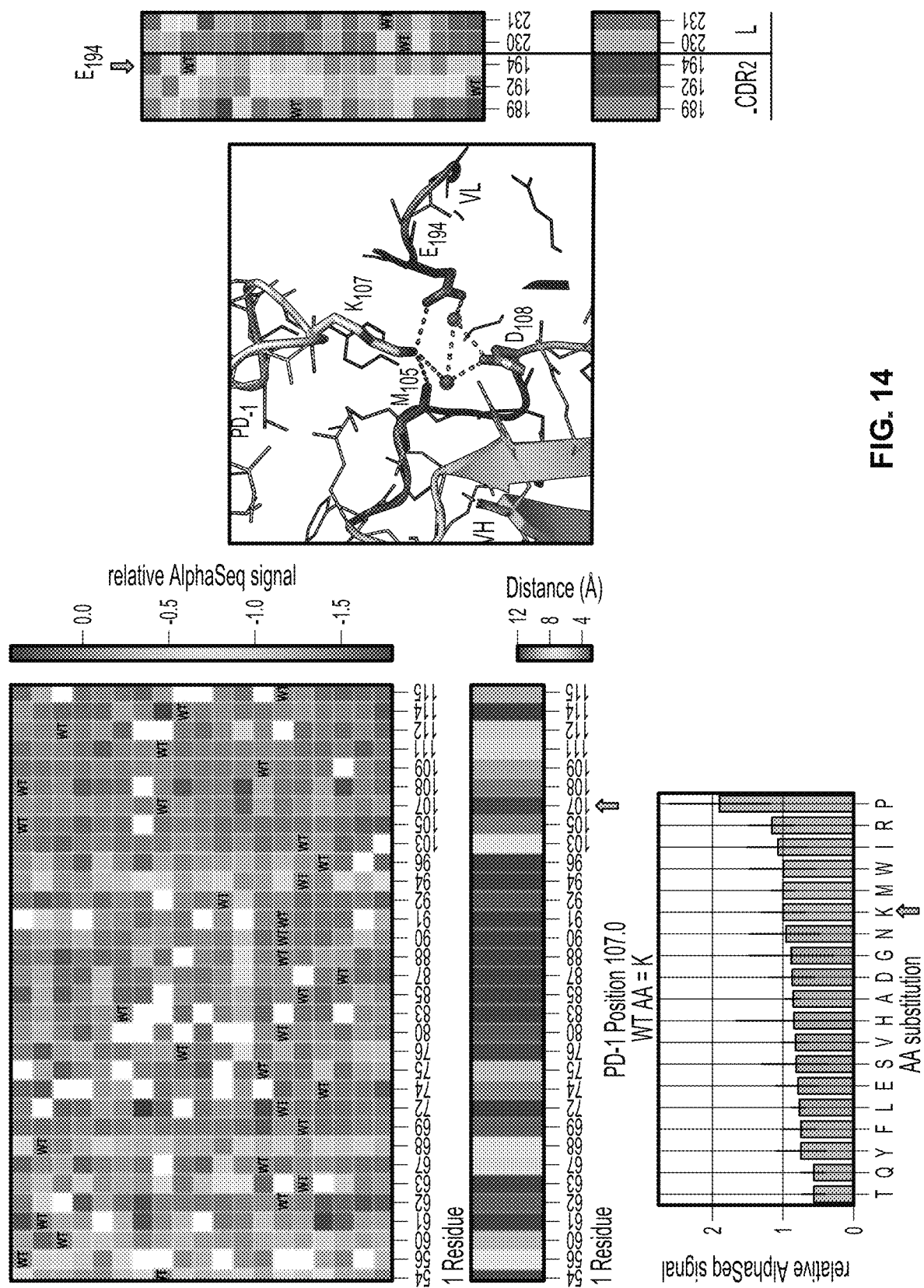

FIG. 14 is a representation of the same dataset presented in the heatmap of FIG. 7, with a graphical representation of the crystal structure of the antibody-antigen interface. These data indicate that spatial epitope mapping alone may give a false positive signal. For example, the lysine residue at PD-1 position 107 is spatially close to the antibody as revealed by the distance heatmap and is making a well-defined set of interactions with antibody residues, including μl 94 in the VL domain. However, both residues can be mutated without effect, so this interaction as revealed by spatial epitope mapping may be considered a false positive due to its functional insignificance, as demonstrated by the AlphaSeq mutational analysis. A color version of the heat map(s) included in, e.g., FIG. 14 is available via USPTO PAIR (access 63/033,176, Supplemental Content tab).

FIG. 15 is a diagram illustrating the potential for the AlphaSeq platform to detect compensatory mutations by measuring relative AlphaSeq signal in a library-by-library screen between pembro scFv (antibody) and PD-1 (antigen). The library-by-library analysis is capable of identifying the relatively rare subset of interactions that show the AlphaSeq signal signature plotted. Compensatory mutations showing this signature allow wild-type-like mating frequencies to be observed for mutant pairs in which at least one, or both, of the mutants have weakened interactions with the cognate wild-type form. By examining the x-ray structure of the wild-type complex, residues harboring these compensatory mutations have been found to be spatially close.

FIG. 16 shows plots of three pairs of mutant protein binding partners that exhibit the signature of compensatory mutations, along with a graphical representation of the crystal structure of the antibody-antigen interface with the relevant residues highlighted.

FIG. 17 shows plots of two pairs of mutant protein binding partners that exhibit the signature of compensatory mutations, along with a graphical representation of the crystal structure of the antibody-antigen interface with the relevant residues highlighted.

FIG. 18 is a graphical representation highlighting pairs of compensatory mutations that were detected by measuring relative AlphaSeq signal in a library-by-library screen between a library of pembro scFv (antibody) mutants and PD-1 (antigen) mutants. A total of ten unique residue-to-residue interactions involving seven antibody residues and six antigen residues are shown, with all compensatory pairs spatially close at the antigen/antibody interface. These compensatory mutations yield unique information about the protein-protein interface that are not available when using one-sided binding-based methods.

Figure 19:
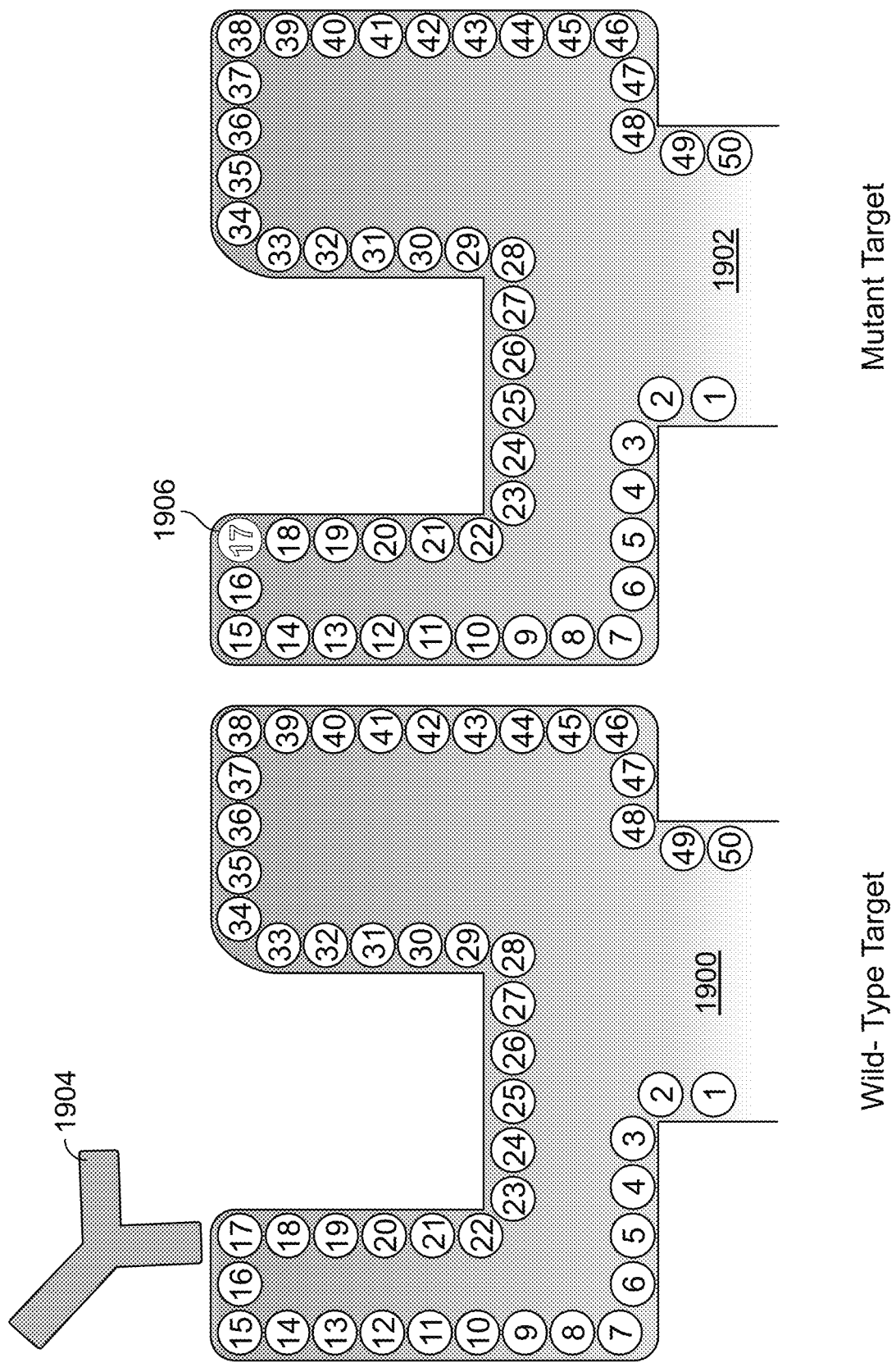

FIG. 19 depicts previous methods for epitope mapping by targeted mutagenesis. In previously known conventional methods for epitope mapping, surface residues on the targets protein were mutated one-by-one on an individual basis to alanine (alanine scanning) or another amino acid, and binding of the target by the antibody was evaluated. Mutations that disrupted binding of the antibody to the target were inferred to be important, in certain embodiments, for binding and inferred to comprise the epitope. This approach was slow and expensive because each antibody-target mutant interaction was evaluated separately, or targets mutants were batched and one antibody was epitope-mapped at a time. For example, target protein 1900 may be subjected to alanine scanning mutagenesis to map the epitope for antibody 1904. Mutant target 1902 comprises a mutation 1906 of an amino acid residue at position 17 of the protein. Mutation 1906 disrupts binding between mutant target 1902 and antibody 1904, indicating that the epitope of the target is in the vicinity of the amino acid residue at position 17.

Figure 20:
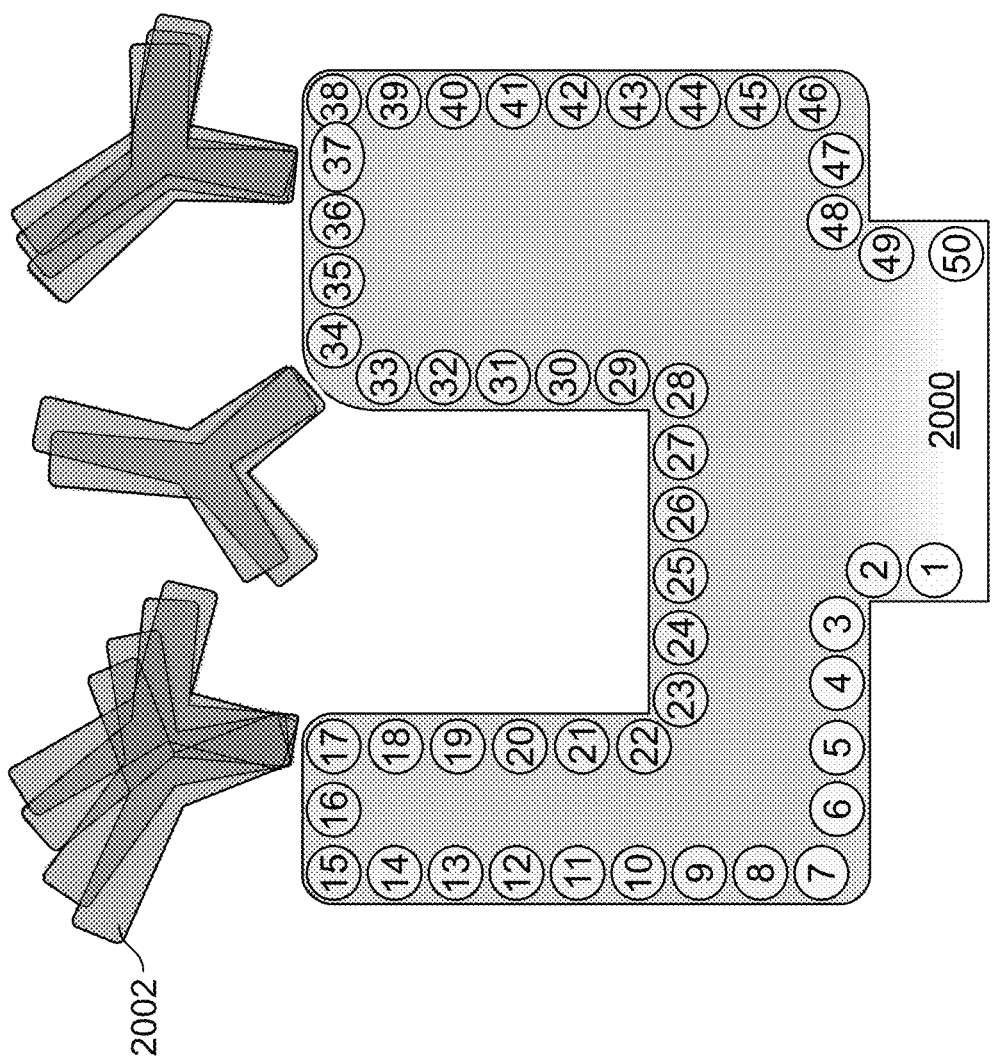

FIG. 20 depicts a library-by-library screen for epitope mapping using the methods disclosed herein. In some implementations, target protein 2000 may be subjected to alanine scanning mutagenesis across all amino acid positions of the protein. In other implementations, target protein 2000 may be subjected to full site-saturation mutagenesis wherein each amino acid position of the protein is mutated to every available amino acid variants to produce a library of mutant target proteins. A library of antibodies, for example antibody 2002, are provided and screened against the mutagenized library of target proteins according to the methods disclosed herein to evaluate all binding interactions between the target protein library and the antibody library. For each antibody of the antibody library, binding interactions are evaluated and target protein epitopes may be inferred from the locations of mutations that disrupt binding relative to wild-type binding.

Figure 21:
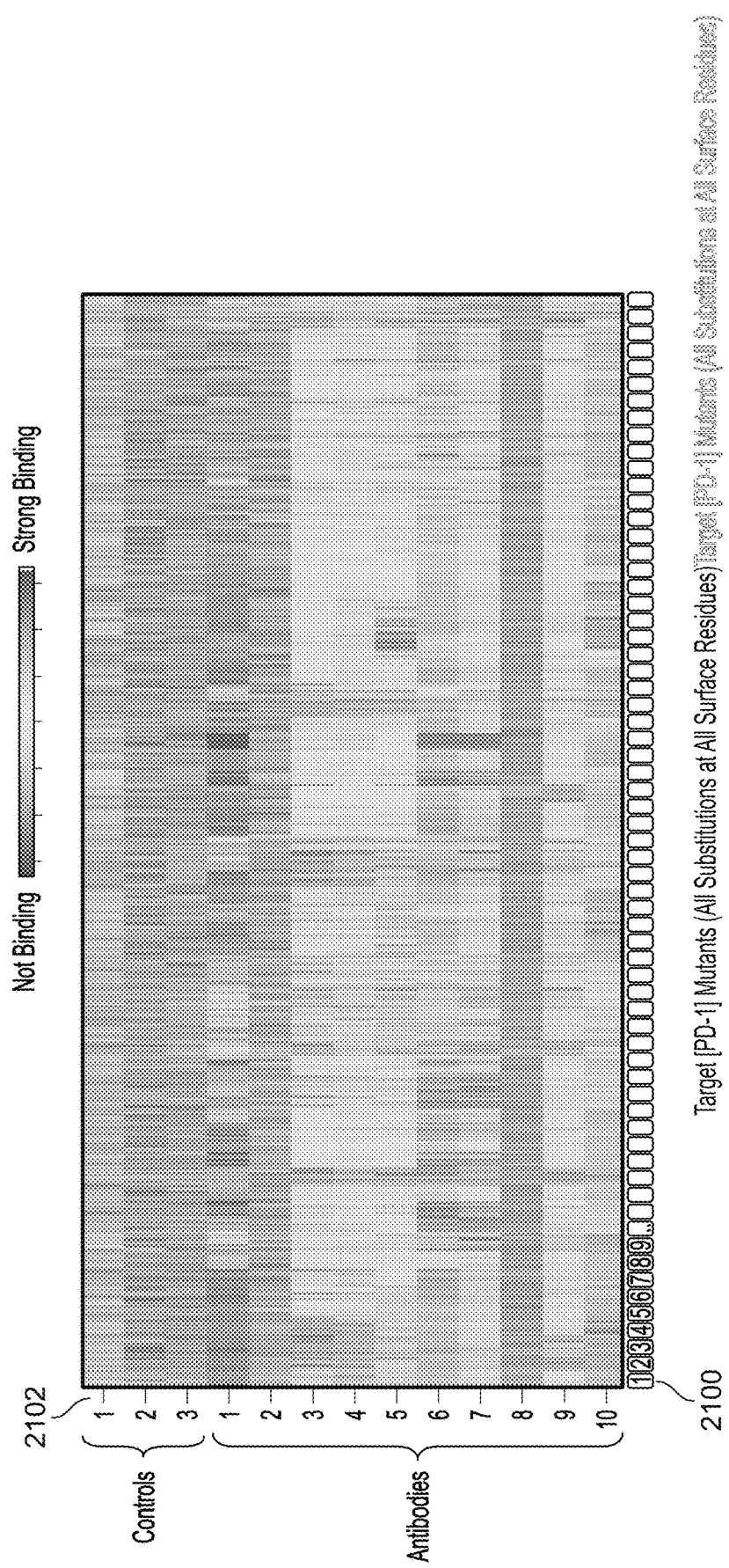

FIG. 21 is a graphical representation of data generated by the library-by-library screen depicted in FIG. 20. The data are presented as a heatmap representing results of the screen of PD-1 variants (antigen variants) against the library of antibodies (antibody). All PD-1 surface residues were chosen for mutagenesis and the resulting SSM library was subjected to the AlphaSeq workflow. AlphaSeq signals are displayed in a heatmap format, with the darkly shaded squares of varied patterns indicating high and low mating frequencies. Ten antibodies were screened against the site-saturation mutagenesis library of PD-1 surface positions. PD-1 surface positions are depicted left to right along axis 2100 and test antibodies and controls are depicted along axis 2102. A color version of the heat map(s) included in, e.g., FIG. 21 is available via USPTO PAIR (access 63/033,176, Supplemental Content tab).

Figure 22:
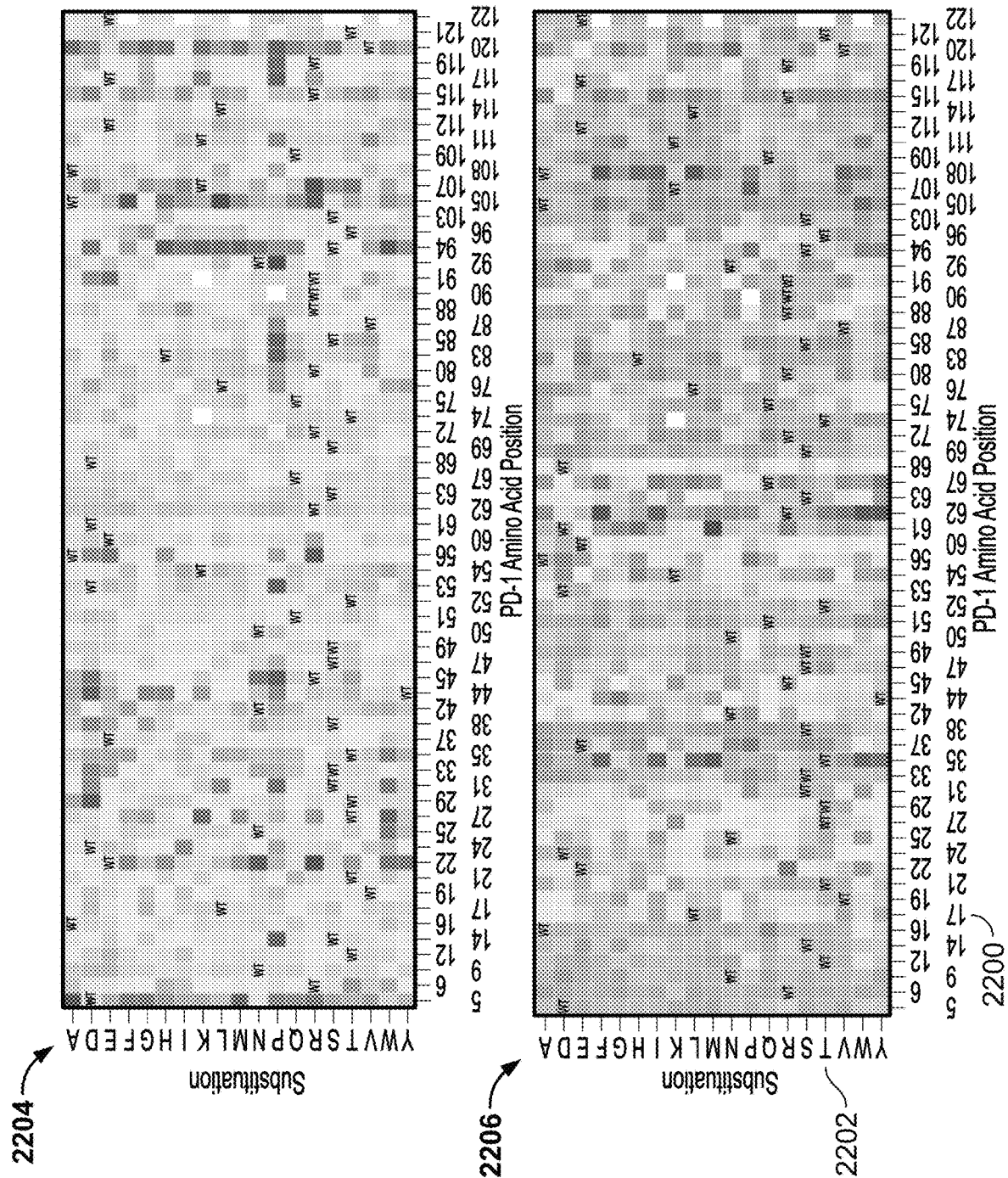
Figure 23:
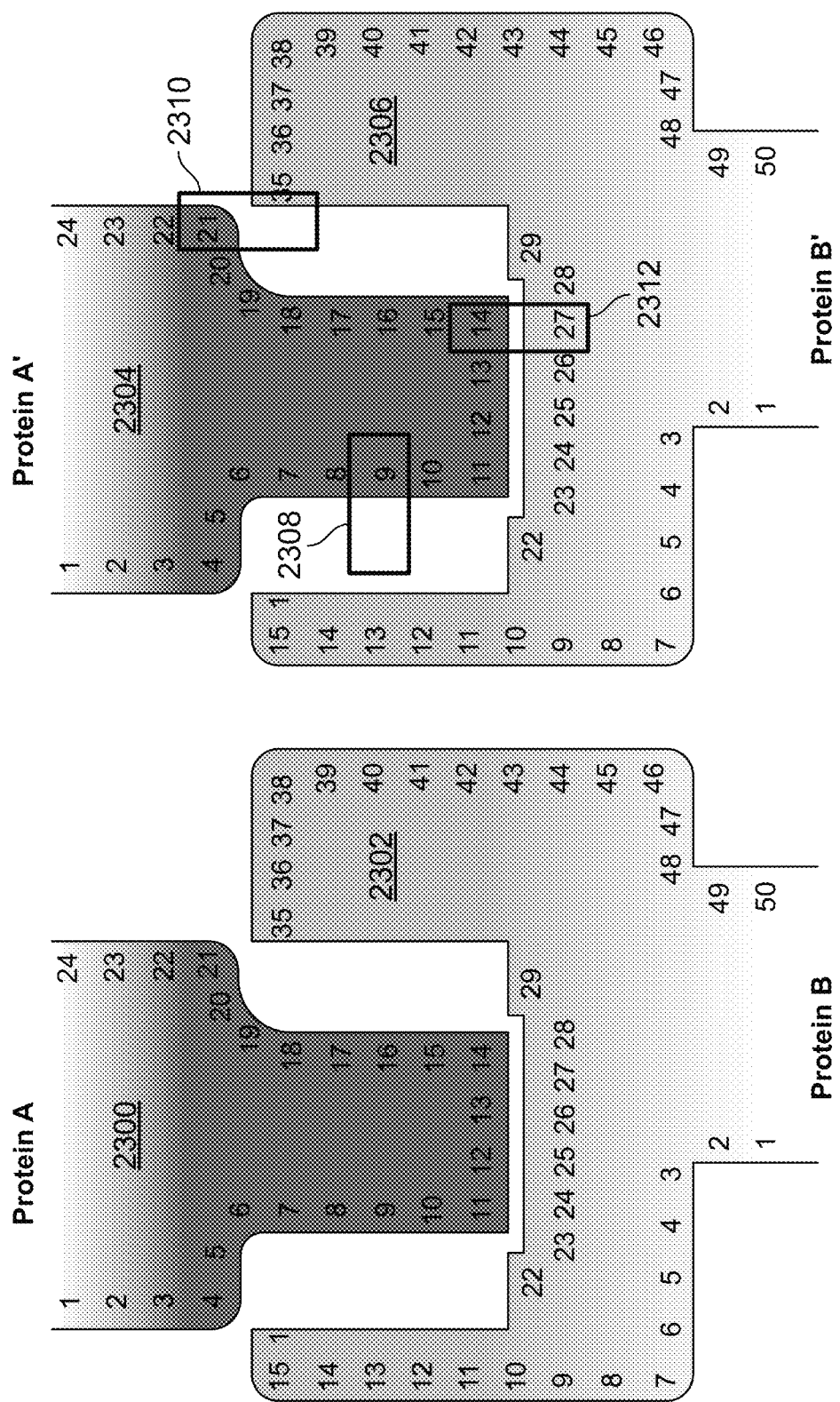
Figure 24A:
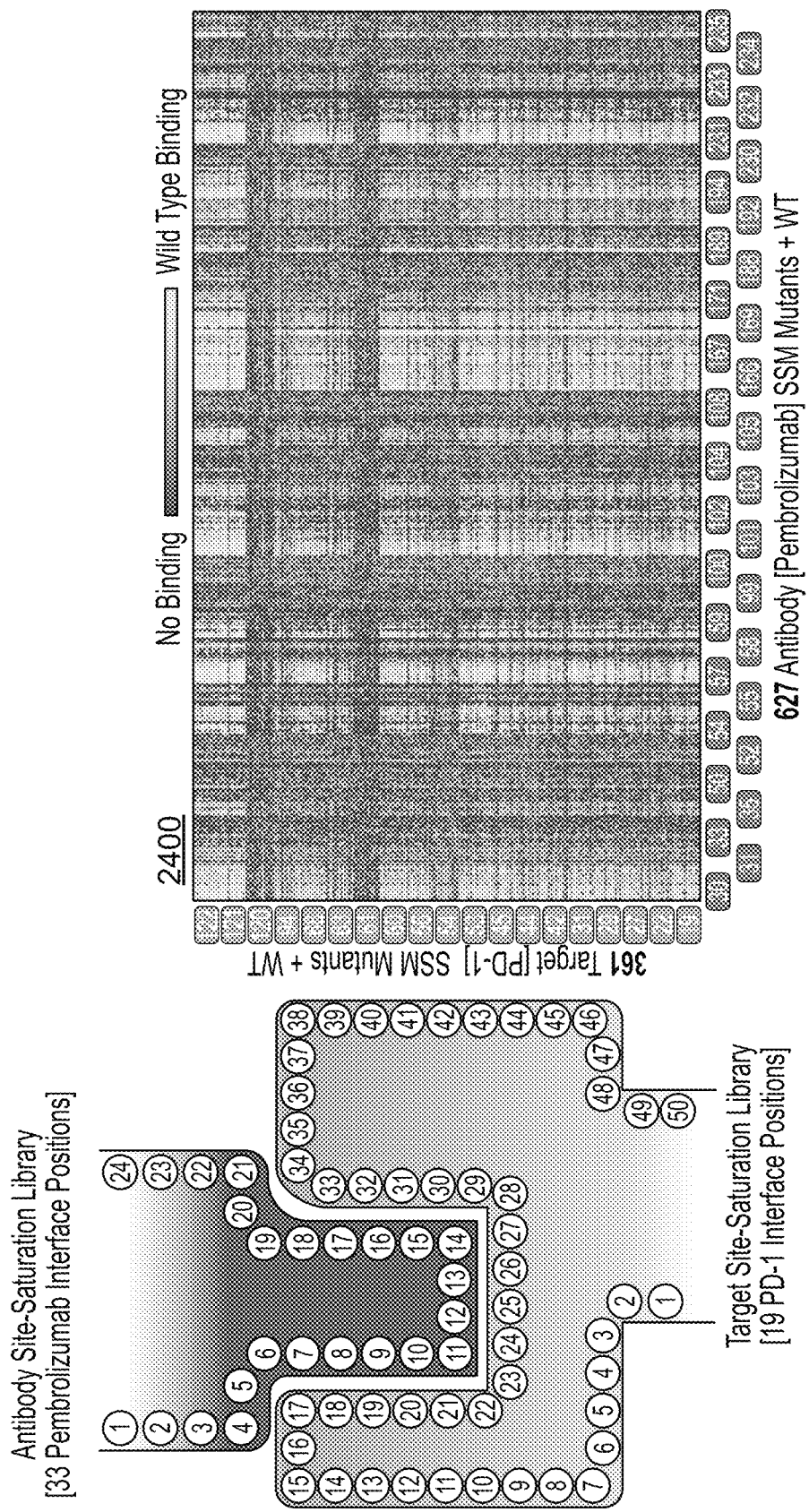
Figure 24B:
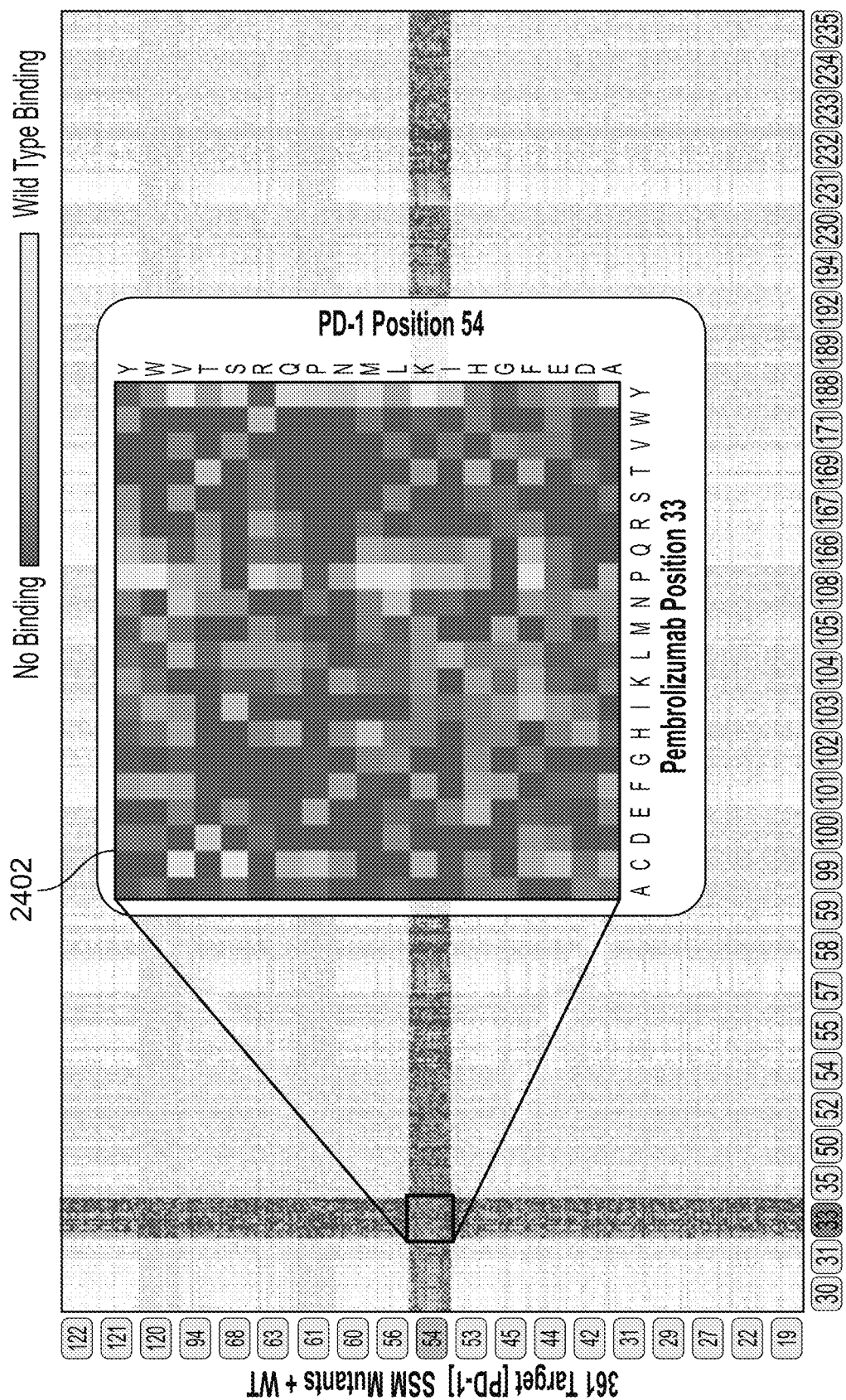
Figure 24C:
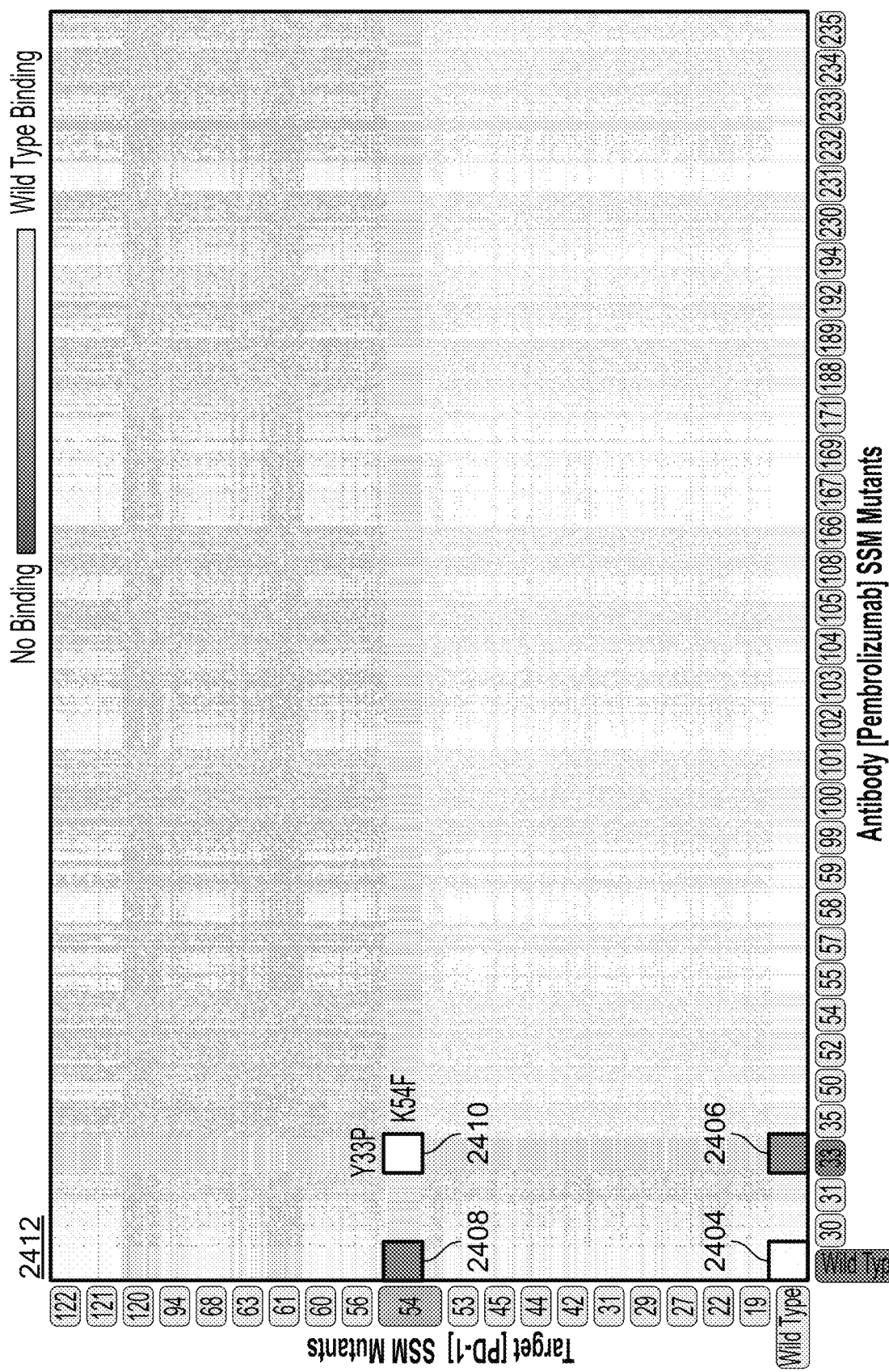
Figure 24D:
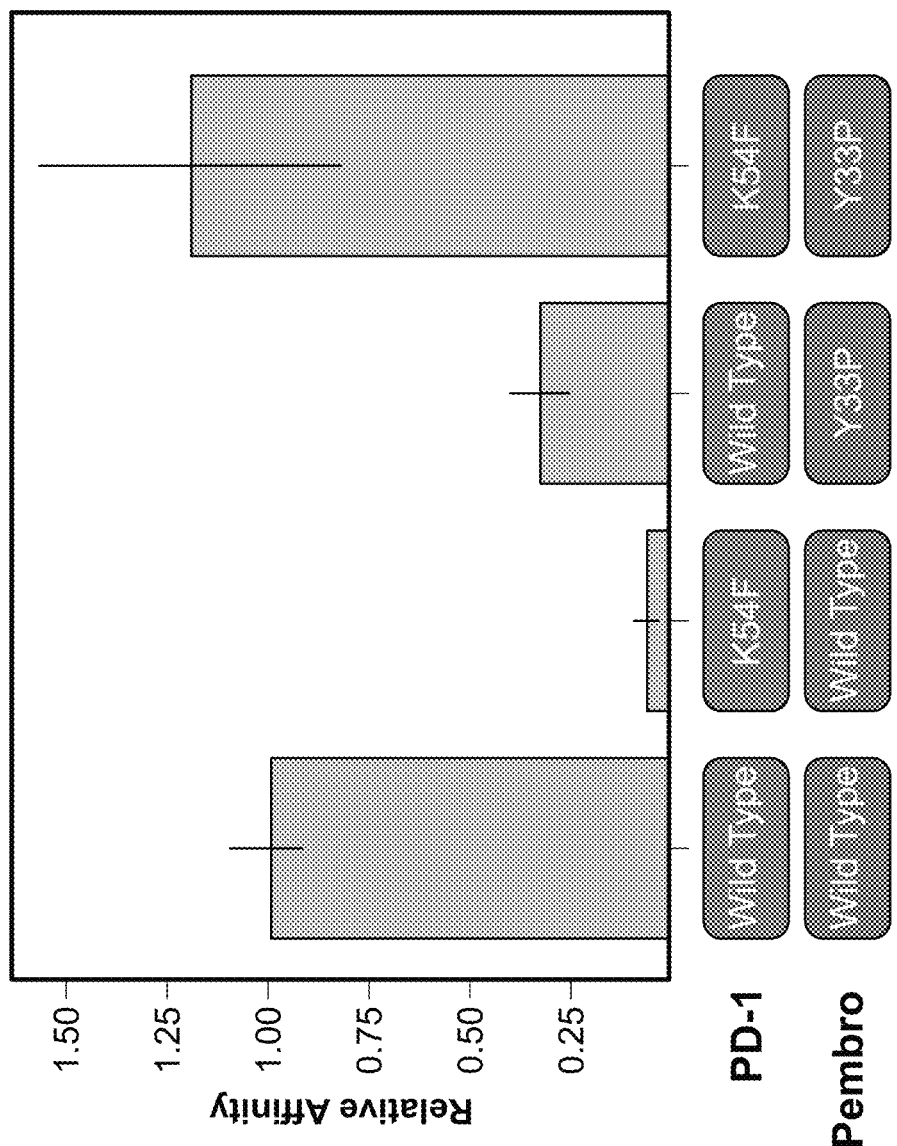

FIG. 22 is a further representation of two of the antibodies depicted in FIG. 21. Data for antibodies 9 and 10 from FIG. 21 have been reconfigured in FIG. 22 as a enrichment/depletion heatmap to show results of the library-by-library screen. Heatmap 2204 represents data for the screen of pembrolizumab (antibody) against the library of PD-1 surface residue variants (antigen variants), and heatmap 2206 represents data for the screen of nivolumab (antibody) against the library of PD-1 surface residue variants (antigen variants). AlphaSeq signals are displayed in a heatmap format, with the darkly shaded squares of varied patterns indicating high and low mating frequencies. PD-1 surface positions are depicted left to right along axis 2200 and individual amino acid variants for each PD-1 surface position are depicted along axis 2202. A color version of the heat map(s) included in, e.g., FIG. 22 is available via USPTO PAIR (access 63/033,176, Supplemental Content tab).

FIG. 23 depicts a possible output of the methods disclosed herein, wherein compensatory mutations are identified between a first protein binding partner and a second protein binding partner. Wild-type protein 2300 and wild-type protein 2302 interact as first and second protein binding partners. A library-by-library full site-saturation mutagenesis screen according to the methods disclosed herein identified mutations of the first and second protein binding partners as positions 2308, 2310, and 2312, such that for each mutation, the mutated protein binding partners interact in a manner similar to the wild-type interaction but that mutated protein binding partners do not interact with the wild-type protein binding partners. For example, mutant protein binding partner 2304 interacts strongly with mutant protein binding partner 2306 but does not interaction with wild-type protein binding partner 2302 due to the mutations at positions 2308, 2310, and 2312. Identifying and designing such orthogonal protein binding interactions may be useful for applications including engineered antibodies, engineering synthetic receptor/ligand pairs, or for synthetic biology tools such as engineered enzyme scaffolds.

FIG. 24A depicts a library-by-library screen for epitope mapping using the methods disclosed herein. A library-by-library screen was performed between a site-saturation mutagenesis library of PD-1 (antigen) surface residue mutants and a site-saturation mutagenesis library of pembrolizumab (antibody) mutants. 19 amino acid positions of PD-1 were selected for mutagenesis and 33 amino acid positions of pembrolizumab were selected for mutagenesis. Amino acid residues of the antigen and the antibody were selected in the vicinity of the protein-protein binding interface. The AlphaSeq platform was used to measure all pairwise interactions between the site-saturation mutagenesis libraries of the antigen and antibody protein binding partners, comprising greater than 220,000 pairwise interactions. Heatmap 2400 illustrates the pairwise library-by-library intensity measurements by AlphaSeq of the interactions between the library of PD-1 mutants and the library of pembrolizumab mutants relative to the binding affinity between wild-type PD-1 and wild-type pembrolizumab, with lighter shading representing wild-type binding affinity and darker shading representing reduced binding affinity.

FIG. 24B depicts an increasingly detailed view of a subset of the data presented in heatmap 2400 of FIG. 24A. Heatmap inset 2402 represents that data for pairwise interaction between 20 PD-1 variants carrying mutations at position 54 and 20 pembrolizumab variants carrying mutations at position 54, or 400 total protein-protein interactions measured by the methods disclosed herein. In a single AlphaSeq assay, binding affinity data are measured for all pairwise combinations of the 33 selected pembrolizumab positions and the 19 selected PD-1 positions and evaluated relative to wild-type binding affinity between the two protein binding partners.

FIG. 24C highlights a particular pair-wise interaction between a single PD-1 mutant and a single pembrolizumab variant. Heatmap 2412 illustrates the pairwise library-by-library intensity measurements by AlphaSeq of the interactions between the library of PD-1 mutants and the library of pembrolizumab mutants relative to the binding affinity between wild-type PD-1 and wild-type pembrolizumab, with lighter shading representing wild-type binding affinity and darker shading representing reduced binding affinity, and two particular mutations are highlighted: PD-1 K54F and pembrolizumab Y33P. Square 2404 represents the binding affinity for wild-type PD-1 and wild-type pembrolizumab and is white according to the shading of the heatmap. Square 2406 represents the binding affinity between wild-type PD-1 and pembrolizumab Y33P and is darkly shaded, indicating significantly reduced binding affinity relative to wild-type. Square 2408 represents the binding affinity between PD-1 K54F and wild-type pembrolizumab and is darkly shaded, indicating significantly reduced binding affinity relative to wild-type. Square 2410 represents the binding affinity between PD-1 K54F and pembrolizumab Y33P and is shaded white, indicating binding affinity that is similar to wild-type. I.e., for these individual mutations, each mutation on its own significantly reduced binding affinity between the first and second protein binding partners, but when the mutations are present simultaneously binding affinity is restored to a level similar to wild-type binding affinity. The mutation of the first protein binding partner compensates for the binding deficiency cause by the mutation of the second protein binding partner and promotes a binding affinity that is similar to wild-type binding affinity A color version of the heat map(s) included in, e.g., FIG. 24A-24C is available via USPTO PAIR (access 63/033,176, Supplemental Content tab).

FIG. 24D is a graphical representation of the data presented in heatmap 2412 of FIG. 24C. Four pairwise interactions between combinations of wild-type and mutant PD-1 and pembrolizumab are shown. The graph is normalized such that the binding affinity between wild-type PD-1 and wild-type pembrolizumab is set to 1.0 and pairwise interactions of that mutant protein binding partners are quantified relative to 1.0. As described in relation to FIG. 24C, these mutations exhibit a unique and unexpected property of compensating for the detrimental effect on binding affinity that each mutation exerts on its own, such that PD-1 K54F and pembrolizumab Y33P show binding that is similar to the binding affinity between the wild-type protein binding partners.

Figure 25:
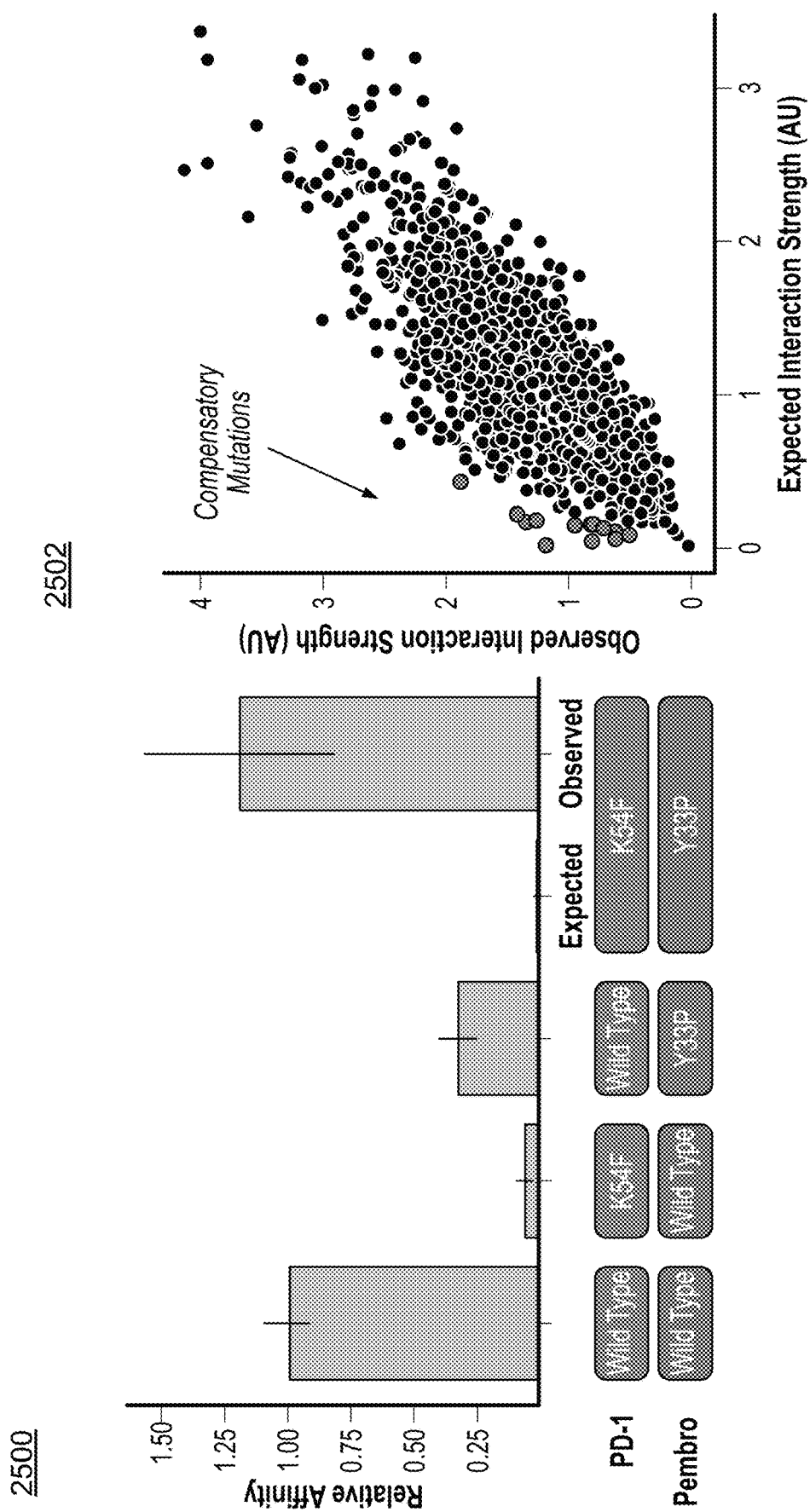
Figure 26:
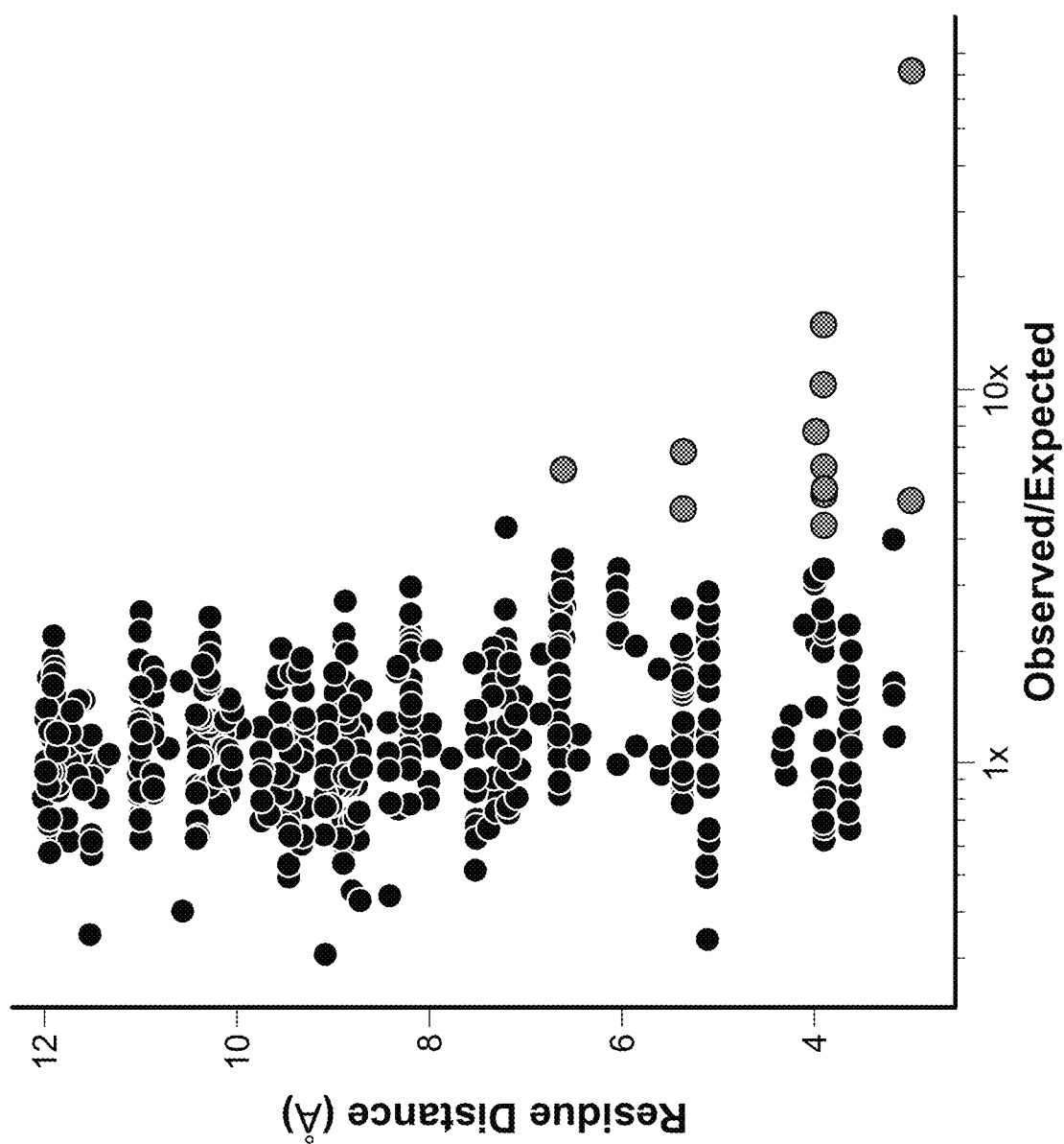
FIG. 26 is a plot of the ratio of observed interaction strength to expected interaction strength against distance between amino acid residues between the protein binding partners.
Figure 27:
FIG. 27 is a three-dimensional model based on the x-ray crystal structure of the interface between PD-1 (antigen) and pembrolizumab (antibody).

FIG. 25 depicts a first plot of expected and observed interaction strengths between two protein binding partners and a second plot of expected vs. observed interaction strength between antibody-antigen protein binding partners evaluated using the methods disclosed herein. Expected interaction strength may be defined by multiplying the relative binding affinity of a mutated first protein binding partner with wild-type by the relative binding affinity of a mutated second protein binding partner with wild-type. I.e., the expected interaction strength of an interaction between PD-1 K54F and pembrolizumab Y33P may be defined by multiplying the relative affinity between PD-1 K54F and wild-type pembrolizumab by the relative affinity between pembrolizumab Y33P and wild-type PD-1. As shown in plot 2500, the expected interaction strength between PD-1 K54F and pembrolizumab Y33P is nearly zero, due to the substantially reduced binding affinity of each individual mutation with its corresponding wild-type protein binding partner. However, the observed interaction strength between PD-1 K54F and pembrolizumab Y33P is nearly identical to the interaction strength between wild-type PD-1 and wild-type pembrolizumab due to the unexpected compensatory effect of these mutations. Plot 2502 depicts expected interaction strengths plotted against observed interactions strengths and points to and highlights compensatory mutations in light gray. These compensatory mutations are pairs of mutant protein binding partners for which the observed interaction strength significantly exceeds the expected interaction strength due to the unexpected compensatory effect of the mutations.

FIG. 26 is a plot of the ratio of observed interaction strength to expected interaction strength against distance between amino acid residues between the protein binding partners. Compensatory mutations, for which the observed interaction strength is significantly higher than the expected interaction strength, are highlighted in light gray. The plot demonstrates that pairs of amino acid residues that were identified to be compensatory mutations are within close physical proximity to each other at the protein-protein interface. All the compensatory mutations identified by the methods disclosed herein were less than 7 angstroms apart at the protein-protein interface according to a known x-ray crystal structure.

FIG. 27 is a three-dimensional model based on the x-ray crystal structure of the interface between PD-1 (antigen) and pembrolizumab (antibody) Amino acid residues for which compensatory mutations were identified are highlighted in light gray. The model demonstrates that amino acid residues that were identified to be compensatory mutations are all within close physical proximity to each other at the protein-protein interface.

In some implementations, the present invention provides a novel A method for identifying compensatory mutations between two protein binding partners, the method comprising:

providing a library of first protein binding partners, the library of first protein binding partner, comprising: a first wild-type polypeptide and a first plurality of mutant polypeptides;

providing a library of second protein binding partners, the library of second protein binding partners, comprising: a second wild-type polypeptide and a second plurality of mutant polypeptides;

measuring an observed affinity value between each protein binding partner of the library of first protein binding partners and each protein binding partner of the library of second protein binding partners; and identifying, based on the respective observed affinity value between each protein binding partner of the library of first protein binding partners and each protein binding partner of the library of second protein binding partners, one or more pairs of protein binding partners, comprising:

(i) one polypeptide of the first plurality of mutant polypeptides, and (ii) one polypeptide of the second plurality of mutant polypeptides, wherein the observed affinity value of each pair of the one or more pairs of protein binding partners is substantially different than a respective expected affinity value between the respective pair of protein binding partners, wherein the expected affinity value, for a given pair of protein binding partners is calculated based on a) the observed affinity value between the first wild-type polypeptide of the given pair and the one polypeptide of the second plurality of mutant polypeptides of the given pair, and b) the observed affinity value between the one polypeptide of the first plurality of mutant polypeptides of the given pair and the second wild-type polypeptide of the given pair.

In some implementations, each protein binding partner of the library of first protein binding partners is expressed on the surface of one of a first plurality of yeast cells and each protein binding partner of the library of second protein binding partners is expressed on the surface of one of a second plurality of yeast cells.

In some implementations, the observed affinity value between each protein binding partner of the library of first protein binding partners and each protein binding partner of the library of second protein binding partners is measured by synthetic agglutination between the first plurality of yeast cells and the second plurality of yeast cells.

In some implementations, each protein binding partner of the first library of protein binding partners is an antibody, scFv, Fab, or VHH species.

In some implementations, each protein binding partner of the second library of protein binding partners is an antigen species.

In some implementations, each protein binding partner of the first library of protein binding partners is a receptor species.

In some implementations, each protein binding partner of the second library of protein binding partners is a ligand species.

In some implementations, each of the first plurality of mutant polypeptides and each of the second plurality of mutant polypeptides are produced by user-directed mutagenesis.

In some implementations, the observed affinity value, for each pair of the one or more pairs of protein binding partners, is substantially higher than an expected affinity value of the pair of protein binding partners.

In some implementations, the observed affinity value, for each pair of the one or more pairs of protein binding partners, is higher than the expected affinity value of the pair of protein binding partners by a factor of greater than two.

In some implementations, the observed affinity value, for each pair of the one or more pairs of protein binding partners, is substantially lower than an expected affinity value of the pair of protein binding partners.

In some implementations, the observed affinity value, for each pair of the one or more pairs of protein binding partners, is lower than the expected affinity value of the pair of protein binding partners by a factor of greater than two.

In some implementations, the present invention provides a novel method for identifying compensatory mutations between two protein binding partners, the method comprising:
- providing a first library of protein binding partners, the first library of protein binding partners, comprising: a first wild-type polypeptide and a first plurality of mutant polypeptides;
- providing a second library of protein binding partners, the second library of protein binding partners, comprising: a second wild-type polypeptide and a second plurality of mutant polypeptides;
- measuring an observed affinity value between each protein binding partner of the first library of protein binding partners and each protein binding partner of the second library of protein binding partners;
- identifying, based on the observed affinity value between each protein binding partner of the first library of protein binding partners and each protein binding partner of the second library of protein binding partners, one or more pairs of protein binding partners that have a respective observed affinity value that is substantially different than the observed affinity value between the first wild-type polypeptide and the second wild-type polypeptide.

In some implementations, the one or more pairs of protein binding partners meets the following conditions:
a. the observed affinity value between one polypeptide of the first plurality of mutant polypeptides and the second wild-type polypeptide is substantially lower than the observed affinity value between the first wild-type polypeptide and the second wild-type polypeptide;
b. the observed affinity value between the first wild-type polypeptide and one polypeptide of the second plurality of mutant polypeptides is substantially lower than the observed affinity value between the first wild-type polypeptide and the second wild-type polypeptide; and
c. the observed affinity value between one polypeptide of the first plurality of mutant polypeptides and one polypeptide of the second plurality of mutant polypeptides is substantially the same or substantially higher than the observed affinity value between the first wild-type polypeptide and the second wild-type polypeptide.

In some implementations, the one or more pairs of protein binding partners meet the following conditions:
a. the observed affinity value between one polypeptide of the first plurality of mutant polypeptides and the second wild-type polypeptide is substantially the same or substantially higher than the observed affinity value between the first wild-type polypeptide and the second wild-type polypeptide;
b. the observed affinity value between the first wild-type polypeptide and one polypeptide of the second plurality of mutant polypeptides is substantially lower than the observed affinity value between the first wild-type polypeptide and the second wild-type polypeptide; and
c. the observed affinity value between one polypeptide of the first plurality of mutant polypeptides and one polypeptide of the second plurality of mutant polypeptides is substantially the same as the observed affinity value between the first wild-type polypeptide and the second wild-type polypeptide.

In some implementations, the one or more pairs of protein binding partners meet the following conditions:
a. the observed affinity value between one polypeptide of the first plurality of mutant polypeptides and the second wild-type polypeptide is substantially lower than the observed affinity value between the first wild-type polypeptide and the second wild-type polypeptide;
b. the observed affinity value between the first wild-type polypeptide and one polypeptide of the second plurality of mutant polypeptides is substantially the same or substantially higher than the observed affinity value between the first wild-type polypeptide and the second wild-type polypeptide; and
c. the observed affinity value between one polypeptide of the first plurality of mutant polypeptides and one polypeptide of the second plurality of mutant polypeptides is substantially the same or substantially higher than the observed affinity value between the first wild-type polypeptide and the second wild-type polypeptide.

In some implementations, the one or more pairs of protein binding partners meet the following conditions:
a. the observed affinity value between one polypeptide of the first plurality of mutant polypeptides and the second wild-type polypeptide is substantially the same or substantially higher than the observed affinity value between the first wild-type polypeptide and the second wild-type polypeptide;
b. the observed affinity value between the first wild-type polypeptide and one polypeptide of the second plurality of mutant polypeptides is substantially the same or substantially higher than the observed affinity value between the first wild-type polypeptide and the second wild-type polypeptide; and
c. the observed affinity value between one polypeptide of the first plurality of mutant polypeptides and one polypeptide of the second plurality of polypeptides is substantially lower than the observed affinity value between the first wild-type polypeptide and the second wild-type polypeptide.

In some implementations, the one or more pairs of protein binding partners meet the following conditions:
a. the observed affinity value between one polypeptide of the first plurality of mutant polypeptides and the second wild-type polypeptide or the observed affinity value between the first wild-type polypeptide and one polypeptide of the second plurality of mutant polypeptides is substantially lower than the observed affinity value between the first wild-type polypeptide and the second wild-type polypeptide;
b. the observed affinity value between one polypeptide of the first plurality of mutant polypeptides and one polypeptide of the second plurality of mutant polypeptides is substantially higher than the observed affinity value between one polypeptide of the first plurality of mutant polypeptides and the second wild-type polypeptide or the observed affinity value between the first wild-type polypeptide and one polypeptide of the second plurality of mutant polypeptides.

In some implementations, a mutation of the one polypeptide of the first plurality of mutant polypeptides defines a paratope of the antibody, scFv, Fab, or VHH species and/or a mutation of the one polypeptide of the second plurality of mutant polypeptides defines an epitope of the antigen species.

In some implementations, a mutation of the one polypeptide of the first plurality of mutant polypeptides and a mutation of the one polypeptide of the second plurality of mutant polypeptides result in an orthogonal binding relationship between the one polypeptide of the first plurality of mutant polypeptides and the one polypeptide of the second plurality of mutant polypeptides such that,
 a. the one polypeptide of the first plurality of mutant polypeptides binds the second wild-type polypeptide and the one polypeptide of the second plurality of mutant polypeptides, and
 b. the one polypeptide of the second plurality of mutant polypeptides binds the one polypeptide of the first plurality of mutant polypeptides and does not bind the second wild-type polypeptide.

In some implementations, a mutation of the one polypeptide of the first plurality of mutant polypeptides and a mutation of the one polypeptide of the second plurality of mutant polypeptides result in an orthogonal binding relationship between the one polypeptide of the first plurality of mutant polypeptides and the one polypeptide of the second plurality of mutant polypeptides such that,
 a. the one polypeptide of the first plurality of mutant polypeptides binds the one polypeptide of the second plurality of mutant polypeptides and does not bind the second wild-type polypeptide, and
 b. the one polypeptide of the second plurality of mutant polypeptides binds the one polypeptide of the first plurality of mutant polypeptides and does not bind the first wild-type polypeptide.

In some implementations, affinity binding data measured by the methods disclosed herein may be outputted to a digital display device. In another implementation, numerical and graphical representations of affinity binding data for wild-type and mutant protein binding partners measured by the methods disclosed herein may be represented on a display device, with notation indicating pairs of mutant protein binding partners bearing mutations that have been identified as compensatory mutations.

In some implementations, for mutant protein binding partners bearing one or more mutations that have been identified as compensatory mutations by the methods disclosed herein, the mutations may be used to engineer protein interactions having the orthogonal binding affinity properties discussed in detail above. For example, in some implementations compensatory mutations identified by the methods disclosed herein may be used for constructing engineered metabolic pathways comprising enzymes heterologous to a production host organism, e.g. for the production of useful secondary metabolites, where the interactions and titers of pathway component enzymes may be fine-tuned by the use of compensatory mutations. Further, the heterologous metabolic pathway components may be engineered using compensatory mutations identified by the methods disclosed herein to not interact with proteins and enzymes within the host organism that may otherwise impair or reduce the activity of the heterologous metabolic pathway.

In another implementation, compensatory mutations to receptors may be identified by the methods disclosed herein allowing for the engineering of the CAR-T cells to express customized cell-surface receptors bearing compensatory mutations. Likewise, a soluble growth factor or cytokine may be engineered to express compensatory mutations identified by the methods disclosed herein, such that the CAR-T cell surface receptor and soluble growth factor or cytokine exhibit a one-sided orthogonal affinity relationship. By introducing possibly only a small number of highly impactful compensatory mutations to each of the cell-surface receptor and the soluble growth factor or cytokine, the CAR-T cell surface receptor may bind and be activated by both the engineered growth factor or cytokine and the wild-type growth factors or cytokines native to the patient's physiological milieu. Conversely, the engineered soluble growth factor or cytokine bearing compensatory mutations identified by the methods disclosed herein will bind and activate only the engineered CAR-T cell surface receptor and not affect the plurality or wild-type cell-surface receptors native to the patient's physiology. This pattern of customized orthogonal protein-protein interactions utilizing the methods disclosed herein will be useful for engineering cell therapies, immunotherapies, and biologics to treat a multitude of diseases and disorders.

In another implementation, compensatory mutations identified by the methods disclosed herein may be useful for the rational design of antibody-based immunotherapies. In an implementation, an antibody, scFv, Fab, or VHH species may be engineered to carry compensatory mutations identified by the methods disclosed herein such that its affinity and specificity for its antigen is tunable and customizable. In another implementation, an antibody, scFv, Fab, or VHH species may be engineered to carry compensatory mutations identified by the methods disclosed herein such that the antibody, scFv, Fab, or VHH species specifically binds a novel epitope distinct from the epitope of the wild-type antibody, scFv, Fab, or VHH species.

EXAMPLE 1

The AlphaSeq platform (e.g., see Example 2 and also US 2017-0205421 A1) and the methods disclosed herein were used to screen a library of mutants of Programmed cell death protein 1 (PD-1), a cell surface receptor expressed on T cells and pro-B cells, against a library of mutants of a short-chain variable fragment (scFv) of the monoclonal antibody pembrolizumab (pembro), a humanized antibody used in cancer immunotherapy, e.g., for the treatment of melanoma, lung cancer, Hodgkin lymphoma, among other cancers. The library of pembro scFv mutants comprised a comprehensive site-saturation mutagenesis library of 33 amino acid residues spanning several domains from position 30 to position 235 of the polypeptide. The library of PD-1 mutants comprised a comprehensive site-saturation mutagenesis library of 60 amino acid residues spanning several domains from position 5 to position 115 of the polypeptide. The library-by-library AlphaSeq screen allowed the interrogation of affinity between each PD-1 mutant and each pembro scFv mutant in a pairwise manner.

A previous experiment screening the PD-1 mutant library against wild-type pembro scFv, results shown in FIG. 7, had identified PD-1 residue K54 as particularly intolerant of amino acid substitution, reflected by low mating frequencies across a wide range of amino acid substitutions at the position. The library-by-library screen of PD-1 and pembro scFv mutants identified a subset of pairs of compensatory mutations of the two protein binding partners. Results for a subset of the compensatory mutations are plotted in FIG. 16. For example, the affinity of the PD-1 mutant K54F with wild-type pembro scFv was 0.05 relative to the wild-type by wild-type interaction of the two protein binding partners (n=3; standard deviation=0.03). The affinity of the pembro scFv mutant Y33P with wild-type PD-1 was 0.33 relative to the wild-type by wild-type interaction of the two protein binding partners (n=3; standard deviation=0.08). However, the affinity of the PD-1 mutant K54F with the pembro scFv mutant Y33P was 1.19 relative to the wild-type by wild-type interaction of the two protein binding partners (n=3; standard deviation=0.38), i.e., the interaction of these two mutants of the protein binding partners was about equivalent to the wild-type by wild-type interaction indicating a pair of compensatory mutations of the two protein binding partners. An analogous signature of affinities between the two binding partners was observed for the PD-1 mutant K54M and the pembro scFv mutant Y33P. For a third pair of mutant protein binding partners, the affinity of the PD-1 mutant K54I with wild-type pembro scFv was 0.40 relative to the wild-type by wild-type interaction of the two protein binding partners (n=3; standard deviation=0.22) and the affinity of the pembro scFv mutant Y101K with wild-type PD-1 was 1.06 relative to the wild-type by wild-type interaction of the two protein binding partners (n=3; standard deviation=0.18), indicating that pembro scFv mutant Y101K had no impact on affinity. However, the affinity of the PD-1 mutant K54I with the pembro scFv mutant Y101K was 1.87 relative to the wild-type by wild-type interaction of the two protein binding partners (n=3; standard deviation=0.35), i.e., the interaction of these two mutants of the protein binding partners had a significantly higher affinity than the wild-type by wild-type interaction indicating a pair of compensatory mutations of the two protein binding partners. The compensatory mutations identified by these experiments correspond to amino acid residues of the antigen and antibody that are spatially close at the antigen/antibody interface.

EXAMPLE 2

Construction of a Yeast-Mating Assay for Screening and/or Determining Protein-Protein Interactions and Protein Interaction Networks (AlphaSeq).

A flow-cytometry assay can be used to differentiate between MATa, MATalpha, and diploid cells. The native yeast sexual agglutinins have been replaced with surface displayed binders (SAPs), and mating efficiency was measured using flow-cytometry. A diploid chromosomal translocation system was developed to combine the genes for both binders onto a single chromosome such that next generation sequencing can be used to evaluate the mating frequency of a particular pair of binders in a large library.

While there are numerous cell-based assays to analyze extracellular binding between a library of proteins and a single target, only cell-free approaches have been developed for characterizing whole protein interaction networks in a single assay. This has meant time consuming and costly library preparation steps involving the purification and labeling of each protein constituent in the network. This example demonstrates a pairwise yeast surface display (PYSD) assay for library-on-library characterization of protein interactions that combines yeast surface display and sexual agglutination to link protein binding to the mating of *S. cerevisiae*. In particular, this example demonstrates that sexual agglutination is highly engineerable by knocking out the native agglutination proteins and instead displaying complementary binding proteins (synthetic agglutination proteins, SAPs) on the surface of MATa and MATalpha yeast cells. This example shows that mating efficiency is highly dependent on the binding affinity and expression level of the surface expressed proteins. A chromosomal translocation scheme can allow protein-protein interaction networks to be analyzed with next generation sequencing and applied to the analysis of two engineered protein interaction networks.

The characterization of protein interaction networks for both binding affinity and specificity is crucial for understanding cellular functions, screening therapeutic candidates, and evaluating engineered protein networks. For example, protein "interactome" mapping has expanded the understanding of biological systems and disease states and can be used to evaluate therapeutic drug candidates for the proper mediation or disruption of specific protein interactions. Additionally, the construction of synthetic systems often requires highly specific and orthogonal protein interactions to properly control cellular behavior. Engineered protein binding domains that allow for the construction of arbitrary protein interaction networks require careful characterization in the context of a highly complex biological system.

Many approaches exist for the analysis of binding between a library of proteins and a single protein target. Yeast surface display (YSD) has been widely used, in part due to the ease of library construction. In order to analyze protein networks, however, it is necessary to screen for binding between all possible protein pairs. Since YSD measures binding with cell fluorescence following incubation with soluble fluorescently tagged target, this approach does not allow for screening against a library of target proteins. A recently developed approach uses DNA barcoded proteins for one-pot library-on-library characterization, but requires the purification of each constituent protein in the network, making the analysis of large networks enormously time consuming and expensive. This disclosure presents a novel method that combines the ease of YSD library generation with a high throughput assay capable of characterizing entire protein interaction networks in a single pot.

A pairwise yeast surface display (PYSD) platform is used for one-to-one, many-to-one, or many-to-many protein interaction characterization. For a one-to-one screen, two isogenic displayer strains, one MATa constitutively expressing a fluorescent marker (e.g., mCherry) and one MATalpha constitutively expressing a second fluorescent marker (e.g., mTurquoise), each express a synthetic adhesion protein (SAP) on their surface as a fusion to Aga2 (Aga2-myc). A mating assay is then used to determine the effect of displaying those particular SAPs on mating efficiency, which is reported as the percent of diploid cells after 17 hours. Haploids and diploids are distinguished based on their expression of mCherry and mTurquoise in a flow cytometry assay. The surface expression strength of each SAP is determined by incubating the mixed culture with FITC conjugated anti-myc antibody prior to flow cytometry.

For a many-to-one or many-to-many screen, one or both of the isogenic displayer strains are replaced with a display library, or a library of displayer cells each expressing a unique SAP. After a short mating period, cells are transferred to media lacking lysine and leucine, which is used to select for diploid cells only. For a many-to-many screen, β-Estradiol (βE) is also added to induce CRE recombinase expression in mated diploids. Recombinase expression results in translocation at lox66/lox71 sites, which flank the SAP integrations, resulting in the juxtaposition of the SAP genes onto one copy of chromosome III. Because of the biased nature of the lox66/71 recombinase site pair, the majority of the population now consists of translocated diploids. Following translocation, cell lysis no longer uncouples the SAP pair from a particular diploid cell. For both the many-to-one and many-to-many screens, a colony PCR of the diploid population is analyzed with next generation sequencing to determine the mating frequency of each SAP pair compared to all other possible SAP pairs included in the assay.

Materials and Methods:

PLASMID CONSTRUCTION: The plasmids used for a first example (Example A) are listed in Table 1. For each construct, backbone and insert fragments were amplified with PCR, gel extracted, and assembled into plasmids using a Gibson reaction. Standard linkers between all parts increased the efficiency and consistency of cloning. All backbones, consisting of a high copy origin of replication and ampicillin resistance, were flanked with PmeI restriction sites for easy linearization and integration into the yeast chromosome. All plasmids contain approximately 500 bases of chromosomal homology upstream and downstream of the target locus. Knockout (KO) plasmids contain upstream and downstream chromosomal homology, but no gene cassette. The sequence of each promoter, open reading frame, terminator, and chromosomal homology were verified with Sanger sequencing.

TABLE 1

Plasmids used in Example A.

| Plasmid Name | Gene Cassette | Marker | Integration Locus |
|---|---|---|---|
| pPYSD1 | Ura3KO | [5-FOA] | AGA1 |
| pPYSD2 | pGPD-mCherry | BleoMX | LTR2 |
| pPYSD3 | pGPD-mTurquoise | BleoMX | LTR2 |
| pPYSD4 | Aga2KO | URA | AGA2 |
| pPYSD5 | Sag1KO | URA | SAG1 |
| pPYSD6 | pGPD-Aga1 | NatMX | HIS3 |
| pPYSD7 | pGAL1-HygMX/pACT1-Zev4 | KanMX | YCR043 |
| pPYSD8 | pZ4-CRE/pGPD-GAVN | KanMX | YCR043 |
| pPYSD9 | pGPD-Aga2_Bfl1/ lox66/mCherry | Trp1 | ARS314 |
| pPYSD10 | pGPD-Aga2_BclB/ lox66/mCherry | Trp1 | ARS314 |

TABLE 1-continued

Plasmids used in Example A.

| Plasmid Name | Gene Cassette | Marker | Integration Locus |
|---|---|---|---|
| pPYSD11 | pGPD-Aga2_Bcl2/ lox66/mCherry | Trp1 | ARS314 |
| pPYSD12 | pGPD-Aga2_BHRF1/ lox66/mCherry | Trp1 | ARS314 |
| pPYSD13 | pGPD-Aga2_Bim-BH3/ lox71/mTurquoise | Trp1 | ARS314 |
| pPYSD14 | pGPD-Aga2_BINDI-F21/ lox71/mTurquoise | Trp1 | ARS314 |
| PPYSD15 | pGPD-Aga2_BINDI-B+/ lox71/mTurquoise | Trp1 | ARS314 |
| pPYSD16 | pGPD-Aga2_BINDI-2+/ lox71/mTurquoise | Trp1 | ARS314 |
| pPYSD17 | pGPD-Aga2_BINDI-N62S/ lox71/mTurquoise | Trp1 | ARS314 |

Yeast Strain Construction and Growth Conditions: The *S. cerevisiae* strains used in a second example (Example B) are listed in Table 2. EBY100a and W303α MOD were used as initial parent strains. EBY100α was generated through the mating of these two parent strains followed by sporulation and tetrad screening for the appropriate selectable markers. All other strains were constructed with chromosomal integrations by linearizing a given plasmid with a PmeI restriction digest and conducting a standard LiAc transformation procedure. Selection of transformants was accomplished using media deficient in a given auxotrophic marker or with media supplemented with a eukaryotic antibiotic. Diagnostic colony PCRs were conducted following each transformation to verify integration into the proper locus. All yeast assays use standard yeast culture media and growth at 30° C. All liquid culture growth is performed in 3 mL of YPD liquid media and shaking at 275 RPM.

TABLE 2

Yeast strains used in Example B.

| Strain Name | Description | Parent | Transformant |
|---|---|---|---|
| EBY100a | Yeast surface display strain | | |
| W303αMOD | MATα for generation of EBY100α | | |
| EBY100α | MATα version of yeast surface display strain | Mating of EBY100a and W303αMOD | |
| EBY101a | URA knockout with 5-FOA selection | EBY100a | |
| EBY101α | URA knockout with 5-FOA selection | EBY100α | |
| EBY102a | Constitutive expression of Aga1 | EBY101a | pMOD_NatMX_HIS_pGPD-Aga1 |
| EBY102α | Constitutive expression of Aga1 | EBY101α | pMOD_NatMX_HIS_pGPD-Aga1 |
| WTa_mCher | MATa, Consttutive mCherry expression with WT SAG1 | EBY102a | pMOD_BleoMX_LTR2_pGPD-mChe |
| WTα_mTur | MATα, Consttutive mTurquoise expression with WT SAG1 | EBY102α | pMOD_BleoMX_LTR2_pGPD-mTur |
| EBY103a | MATa, Sag1 knockout | EBY102a | pYMOD_URA_KO_SAG1 |
| EBY103α | MATα, Sag1 knockout | EBY102α | pYMOD_URA_KO_SAG1 |
| Δsag1α_mTur | MATα, Consttutive mTurquoise expression with SAG1 KO | EBY103α | pMOD_BleoMX_LTR2_pGPD_mTur |
| EBY104a | MATa, CRE recombinase part A | EBY103a | pYMOD_KanMX_YCR043_pZ4-CRE |
| EBY104α | MATα, CRE recombinase part B | EBY103α | pYMOD_KanMX_YCR043_pACT1-ZEV4 |
| yNGYSDa | Final MATa parent strain, with Sce1 landing pad | EBY104a | pYMOD_BleoMX_ARS314_pGAL-Sce1 |
| yNGYSDα | Final MATα parent strain, with Sce1 landing pad | EBY104α | pYMOD_BleoMX_ARS314_pGAL-Sce1 |
| yNGYSDa_Bfl1 | MATa haploids used in pairwise and batched mating assays | yNGYSDa | pNGYSDa_Bfl1 |
| yNGYSDa_BclB | | yNGYSDa | pNGYSDa_BclB |
| yNGYSDa_Bcl2 | | yNGYSDa | pNGYSDa_Bcl2 |
| yNGYSDa_BclW | | yNGYSDa | pNGYSDa_BclW |
| yNGYSDa_BclXL | | yNGYSDa | pNGYSDa_BclXL |
| yNGYSDa_Mcl1[151-321] | | yNGYSDa | pNGYSDa_Mcl1[151-321] |
| yNGYSDα_Bim.BH3 | MATα haploids used in pairwise and batched mating assays | yNGYSDα | pNGYSDα_Bim.BH3 |
| yNGYSDα_Noxa.BH3 | | yNGYSDα | pNGYSDα_Noxa.BH3 |

TABLE 2-continued

Yeast strains used in Example B.

| Strain Name | Description | Parent | Transformant |
|---|---|---|---|
| yNGYSDα_Puma.MH3 | | yNGYSDα | pNGYSDα_Puma.BH3 |
| yNGYSDα_Bad.BH3 | | yNGYSDα | pNGYSDα_Bad.BH3 |
| yNGYSDα_Bik.BH3 | | yNGYSDα | pNGYSDα_Bik.BH3 |
| yNGYSDα_Hrk.BH3 | | yNGYSDα | pNGYSDα_Hrk.BH3 |
| yNGYSDα_Bmf.BH3 | | yNGYSDα | pNGYSDα_Bmf.BH3 |
| yNGYSDα_FINDI-F21 | | yNGYSDα | pNGYSDα_FINDI-F21 |
| yNGYSDα_FINDI-F30D | | yNGYSDα | pNGYSDα_FINDI-F30D |
| yNGYSDα_BINDI-B+ | | yNGYSDα | pNGYSDα_BINDI-B+ |
| yNGYSDα_BINDI-BCDP01 | | yNGYSDα | pNGYSDα_BINDI-BCDP01 |
| yNGYSDα_BINDI-B40A | | yNGYSDα | pNGYSDα_BINDI-B40A |
| yNGYSDα_2INDI-2+ | | yNGYSDα | pNGYSDα_2INDI-2+ |
| yNGYSDα_2INDI-4LVT | | yNGYSDα | pNGYSDα_2INDI-4LVT |
| yNGYSDα_WINDI-aBclW | | yNGYSDα | pNGYSDα_WINDI-aBclW |
| yNGYSDα_XINDI-XCDP07 | | yNGYSDα | pNGYSDα_XINDI-XCDP07 |
| yNGYSDα_MINDI | | yNGYSDα | pNGYSDα_MINDI |

Mating Assays: To evaluate the mating efficiency between any two yeast strains in liquid culture, haploid strains were initially grown to saturation, or for approximately 18 hours, from an isogenic colony on a fresh YPD plate. Each haploid was then combined in a fresh 3 mL YPD liquid culture such that the MATa strain was at a density of 100 cells/μL and the MATα strain was at a density of 600 cells/μL. This difference in starting concentration was an adjustment for an observed uneven growth response to mating factor. The cells were also each grown separately in fresh YPD in order to individually assess their surface expression strength. Following 17 hours of growth, 2.5 μL of mating culture was added to 1 mL of molecular grade water and read on a flow cytometer. MATa, MATalpha, and diploid cells were distinguished based on fluorescent intensity of mCherry and mTurquoise. For the experiments described here, a Miltenyi MACSQUANT® VYB was used. The Y2 channel (561 nm excitation laser and 615 nm emission filter) was used to measure mCherry expression and the V1 channel (405 nm excitation laser and 450 nm emission filter) was used to measure mTurquoise expression. The diploid cell population as a percent of total cell population after 17 hours was used as a measure of mating efficiency. Surface expression strength was measured by incubating 10 μL of each individually grown cell strain for 15 minutes with FITC conjugated anti-myc antibody in PBSF following a wash in 1 mL of water. Cells were then washed again and resuspended in 1 mL of water. Flow cytometry was then performed. For the determination of surface expression strength, an ACCURI™ C6 cytometer was used. The FL1.A channel (488 nm excitation laser and 533 nm emission filter) was used to measure FITC binding to the cell. FLOWJO™ is used for all cytometry analysis.

For a one-to-many batched mating assay, a recombinant MATa yeast strain expressing a single SAP fused to Aga2 is combined in a fresh 3 mL YPD culture with multiple recombinant MATalpha yeast strains expressing distinct SAPs fused to Aga2. The MATa strain is added at a density of 100 cells/μL and the MATalpha strains are added in equal concentrations for a total density of 600 cells/μL. After 6 hours of growth, hygromycin is added at 100 ng/μL. 20 hours after the initial culture inoculation, 1 mL of cells are pelleted. 2 μL of cells are removed from the pellet, lysed with 0.2% SDS, spun down to remove all cellular debris, and diluted in water. The lysate is then used as a template for a PCR with standard primers containing overhangs for next generation sequencing and the PCR product, expected to be approximately 350 bases, is purified from a gel slice. Single-read next generation sequencing is then performed. The frequency that a particular barcode is observed relative to the total number of reads provides a relative measure for the number of matings that were caused by the SAP associated with that particular barcode.

For a many-to-many (also see Example 6) batched mating assay, multiple haploid yeast strains of each mating type are combined in a fresh 3 mL YPD culture. The recombinant MATa yeast strains are added in equal concentrations for a total density of 100 cells/μL and the recombinant MATalpha yeast strains are added in equal concentrations for a total density of 600 cells/μL. After 6 hours of growth, hygromycin is added at 100 ng/μL and β-estradiol (βE) is added at 200 ng/μL. 20 hours after the initial culture inoculation, 1 mL of cells are pelleted. 2 μL of cells are removed from the pellet, lysed with 0.2% SDS, spun down to remove all cellular debris, and diluted in water. The lysate is then used as a template for a PCR with standard primers containing overhangs for next generation sequencing and the PCR product, expected to be 650 bases, is purified from a gel slice. Paired-end next generation sequencing is then performed. The frequency that a particular pair of barcodes is observed relative to the total number of reads provides a relative measure for the number of matings that were caused by the SAP pair associated with those two particular barcodes.

Results

For S. cerevisiae haploid cells lacking an essential sexual agglutinin protein, binding is sufficient for the recovery of agglutination and mating in liquid culture. Sag2, the primary MATalpha sexual agglutinin protein, is essential for agglutination. When Sag1 is knocked out, MATalpha cells are unable to mate with wild-type MATa cells in a turbulent liquid culture. However, when complementary SAPs are expressed on a display pair, mating is recovered. Non-complementary SAPs are unable to recover mating.

The frequency of mating events between any two display cells is dependent on the binding affinity between their SAP pair and the surface expression strength of each SAP. The results demonstrate that binding affinity and observed mating efficiency are positively correlated. However, it is possible to improve the correlation by adjusting the mating efficiency for the expression level of each SAP.

Seven SAP pairs with known affinities were evaluated for mating efficiency (see Table 3). The mating efficiency for each pair was tested four times, and an average and standard deviation were calculated. The surface expression strength (SES) of each haploid display strain was also measured, as described in the materials and methods. A "mating score," which adjusts the mating efficiency for differences in surface expression strength, was calculated by dividing the mean mating efficiency by the product of the surface expression strengths of both haploid displayer strains.

TABLE 3

Results of SAP pairs with known affinities evaluated for mating efficiency.

| | F21 | F30D | B+ | B-CDP01 | B40A | 2+ | 4LVT | X-CDP07 | MINDI |
|---|---|---|---|---|---|---|---|---|---|
| AFFINITY (nM) | | | | | | | | | |
| Bfl1 | 1.00 | 1.14 | NA | 517.83 | 2379.33 | NA | NA | 7047.00 | 182444.33 |
| BclB | 31020.00 | 3829.67 | 24.67 | 8.33 | 76.86 | NA | 14730.00 | 106.83 | 21806.67 |
| Bcl2 | 320.97 | 100.21 | NA | 17.31 | 12460.00 | 0.84 | 8.93 | 3.81 | 15620.00 |
| BclXL | 891.33 | 537.27 | NA | 20.20 | 7777.00 | 3539.33 | 12120.00 | 0.59 | 342333.33 |
| BclW | 7402.00 | 3770.00 | NA | 2014.00 | 18963.33 | 1846.33 | 1668.67 | 14.89 | 224916.67 |
| Mcl1 | 1690.30 | 254.91 | NA | 0.46 | 3650.33 | NA | 38860.00 | 17.42 | 0.14 |
| AFFINITY (SD+) | | | | | | | | | |
| Bfl1 | 0.61 | 0.34 | NA | 28.85 | 853.78 | NA | NA | 564.30 | 289587.58 |
| BclB | 7900.93 | 1438.04 | 5.68 | 1.16 | 50.91 | NA | 3713.00 | 8.60 | 11570.10 |
| Bcl2 | 40.77 | 0.57 | NA | 3.46 | 385.88 | 0.56 | 1.32 | 1.03 | 2338.61 |
| BclXL | 216.45 | 20.96 | NA | 4.19 | 314.09 | 250.64 | 1278.01 | 0.07 | 11249.15 |
| BclW | 603.13 | 127.36 | NA | 504.92 | 2051.15 | 318.57 | 128.81 | 0.47 | 196399.98 |
| Mcl1 | 808.64 | 8.40 | NA | 0.09 | 122.07 | NA | 40474.79 | 1.29 | 0.06 |

From a batched mating, it is possible to determine the relative interaction strengths between many proteins in a single assay. By barcoding each SAP, a many-to-one screen can evaluate the relative mating frequencies between a particular SAP and a SAP library using single-read next generation sequencing. A CRE recombinase-based translocation scheme can be used to juxtapose the barcodes from each mating type onto the same chromosome. With the addition of this chromosomal translocation procedure, it is possible to evaluate relative mating frequencies between two SAP libraries using paired-end next generation sequencing. This approach allows for the analysis of arbitrary protein interaction topologies.

Performing additional mating assays with more SAP pairs and using all measured affinities of the SAP pairs can provide the surface expression strength of each SAP and the mating efficiency. A statistical analysis can be performed to determine the relationship between binding affinity, surface expression strength of each SAP, and mating efficiency. The result could be used to determine a predictive relationship between these four variables so that measuring mating efficiency and surface expression strengths could be used to provide an estimation of binding affinity and to determine a threshold for a detectable recovery of mating efficiency.

Example 2 demonstrates a pairwise yeast surface display assay that allows for library-on-library characterization of protein interactions in a single assay. By replacing native *S. cerevisiae* sexual agglutinin proteins with synthetic adhesion proteins, it is possible to couple mating efficiency and protein binding strength. This approach can then be used to evaluate binding between two specific proteins or to determine the relative interactions strengths between a library of proteins.

While certain embodiments have been described, these embodiments have been presented by way of example only and are not intended to limit the scope of the present disclosures. Indeed, the novel methods, apparatuses and systems described herein can be embodied in a variety of other forms; furthermore, various omissions, substitutions and changes in the form of the methods, apparatuses and systems described herein can be made without departing from the spirit of the present disclosures. The accompanying claims and their equivalents are intended to cover such forms or modifications as would fall within the scope and spirit of the present disclosures.

What is claimed is:

1. A method for identifying compensatory mutations between two mutant protein binding partners, the method comprising:

providing a first library of first protein binding partners expressed on a surface of a first plurality of haploid yeast cells, the first library of the first protein binding partners comprising a first wild-type polypeptide and a first plurality of mutant polypeptides of the first wild-type polypeptide;

providing a second library of second protein binding partners expressed on a surface of a second plurality of haploid yeast cells, the second library of the second protein binding partners comprising a second wild-type polypeptide and a second plurality of mutant polypeptides of the second wild-type polypeptide;

culturing the first and second populations of the haploid yeast cells such that diploid yeast cells are produced if the first and second protein binding partners interact;

measuring an observed affinity value between each protein binding partner of the first library of the first protein binding partners and each protein binding partner of the second library of the second protein binding partners; and, identifying the compensatory mutations, based on the observed affinity value between each first protein binding partner and each second protein binding partner, one or more pairs of the first and second protein binding partners having an observed affinity value substantially different than the observed affinity value between the first wild-type polypeptide and the second wild-type polypeptide.

2. The method of claim 1, wherein:

a. the observed affinity value between one polypeptide of the first plurality of mutant polypeptides and the second wild-type polypeptide is substantially lower than the observed affinity value between the first wild-type polypeptide and the second wild-type polypeptide;

b. the observed affinity value between the first wild-type polypeptide and one polypeptide of the second plurality of mutant polypeptides is substantially the same or substantially lower than the observed affinity value between the first wild-type polypeptide and the second wild-type polypeptide; and, c. the observed affinity value between the one polypeptide of the first plurality of mutant polypeptides and the one polypeptide of the second plurality of mutant polypeptides is substantially the same or substantially higher than the observed affinity value between the first wild-type polypeptide and the second wild-type polypeptide.

3. The method of claim 1, wherein:
a. the observed affinity value between one polypeptide of the first plurality of mutant polypeptides and the second wild-type polypeptide is substantially higher than the observed affinity value between the first wild-type polypeptide and the second wild-type polypeptide;
b. the observed affinity value between the first wild-type polypeptide and one polypeptide of the second plurality of mutant polypeptides is substantially the same or substantially higher than the observed affinity value between the first wild-type polypeptide and the second wild-type polypeptide; and,
c. the observed affinity value between the one polypeptide of the first plurality of mutant polypeptides and the one polypeptide of the second plurality of mutant polypeptides is substantially the same or substantially lower than the observed affinity value between the first wild-type polypeptide and the second wild-type polypeptide.

4. The method of claim 1, wherein:
a. the observed affinity value between one polypeptide of the first plurality of mutant polypeptides and the second wild-type polypeptide is substantially the same than the observed affinity value between the first wild-type polypeptide and the second wild-type polypeptide;
b. the observed affinity value between the first wild-type polypeptide and one polypeptide of the second plurality of mutant polypeptides is substantially the same than the observed affinity value between the first wild-type polypeptide and the second wild-type polypeptide; and,
c. the observed affinity value between the one polypeptide of the first plurality of mutant polypeptides and the one polypeptide of the second plurality of mutant polypeptides is substantially higher or substantially lower than the observed affinity value between the first wild-type polypeptide and the second wild-type polypeptide.

5. The method of claim 1, wherein the compensatory mutations result in an observed affinity value substantially and directionally different than the observed affinity value between the first wild-type polypeptide and the second wild-type polypeptide.

6. The method of claim 1, wherein a mutation of one polypeptide of the first plurality of mutant polypeptides defines a paratope of an antibody, scFv, Fab, or VHH species.

7. The method of claim 5, wherein each protein binding partner of the second library of the second protein binding partners is an antigen species.

8. The method of claim 1, wherein each protein binding partner of the first library of the first protein binding partners is a receptor species.

9. The method of claim 7, wherein each protein binding partner of the second library of the second protein binding partners is a ligand species.

10. The method of claim 1, wherein each of the first plurality of mutant polypeptides and each of the second plurality of mutant polypeptides are produced by user-directed mutagenesis.

11. The method of claim 1, wherein three or more compensatory mutations are identified.

* * * * *